United States Patent
Short et al.

(10) Patent No.: US 11,834,472 B2
(45) Date of Patent: Dec. 5, 2023

(54) ANTI-IL-22 ANTIBODIES, ANTIBODY FRAGMENTS, THEIR IMMUNOCONJUGATES AND USES THEREOF

(71) Applicant: BioAtla, Inc., San Diego, CA (US)

(72) Inventors: Jay M. Short, Jackson, WY (US); Gerhard Frey, San Diego, CA (US); Hwai Wen Chang, San Marcos, CA (US); William Boyle, Malibu, CA (US)

(73) Assignee: BIOATLA, INC., San Diego, CA (US)

( * ) Notice: Subject to any disclaimer, the term of this patent is extended or adjusted under 35 U.S.C. 154(b) by 128 days.

(21) Appl. No.: 16/972,357

(22) PCT Filed: Jun. 4, 2019

(86) PCT No.: PCT/US2019/035395
§ 371 (c)(1),
(2) Date: Dec. 4, 2020

(87) PCT Pub. No.: WO2019/236585
PCT Pub. Date: Dec. 12, 2019

(65) Prior Publication Data
US 2021/0230263 A1    Jul. 29, 2021

Related U.S. Application Data

(60) Provisional application No. 62/752,567, filed on Oct. 30, 2018, provisional application No. 62/680,698, filed on Jun. 5, 2018.

(51) Int. Cl.
*A61K 39/395* (2006.01)
*C07K 16/24* (2006.01)
*A61K 47/68* (2017.01)
*A61P 37/00* (2006.01)
*A61P 17/06* (2006.01)
*A61K 39/00* (2006.01)

(52) U.S. Cl.
CPC ........ *C07K 16/244* (2013.01); *A61K 47/6803* (2017.08); *A61K 47/6845* (2017.08); *A61P 17/06* (2018.01); *A61P 37/00* (2018.01); *A61K 2039/505* (2013.01); *C07K 2317/24* (2013.01); *C07K 2317/92* (2013.01); *C07K 2317/94* (2013.01)

(58) Field of Classification Search
CPC .......... A61K 47/6845; A61K 2039/505; C07K 2317/565
See application file for complete search history.

(56) References Cited

U.S. PATENT DOCUMENTS

| | | | |
|---|---|---|---|
| 6,274,710 B1 | 8/2001 | Dumoutier et al. | |
| 6,359,117 B1 | 3/2002 | Dumoutier et al. | |
| 6,551,799 B2 | 4/2003 | Gurney et al. | |
| 7,279,559 B2 | 10/2007 | Jacobs et al. | |
| 7,537,761 B2 | 5/2009 | Xu et al. | |
| 7,737,259 B2 | 6/2010 | Chen et al. | |
| 7,811,567 B2 | 10/2010 | Fouser et al. | |
| 7,901,684 B2 | 3/2011 | Gill et al. | |
| 7,951,372 B1 | 5/2011 | Jacobs et al. | |
| 9,352,024 B2 | 5/2016 | Wu et al. | |
| 9,815,880 B2 | 11/2017 | Scheer et al. | |
| 2003/0099649 A1 | 5/2003 | Jacobs et al. | |
| 2007/0212356 A1 | 9/2007 | Chen et al. | |
| 2007/0243589 A1 | 10/2007 | Gill et al. | |
| 2007/0258982 A1 | 11/2007 | Fouser et al. | |
| 2010/0015086 A1 | 1/2010 | Huang et al. | |
| 2013/0303399 A1 | 11/2013 | Short | |
| 2019/0024078 A1 | 1/2019 | Short et al. | |

FOREIGN PATENT DOCUMENTS

| | | |
|---|---|---|
| AU | 2013200914 A1 | 3/2013 |
| CN | 1679918 A | 10/2005 |
| CN | 105602960 A | 5/2016 |
| CN | 107580603 A | 1/2018 |
| EP | 2327423 A3 | 6/2011 |
| JP | 2005-510451 A | 4/2005 |
| WO | 02068476 A2 | 9/2002 |
| WO | 03083062 A2 | 10/2003 |
| WO | WO2005000897 A2 | 1/2005 |
| WO | WO2006073508 A1 | 7/2006 |
| WO | 2007100643 A2 | 9/2007 |
| WO | WO2018011420 A1 | 1/2018 |

OTHER PUBLICATIONS

International Search Report and Written Opinion for corresponding International application No. PCT/US2019/035395; dated Oct. 18, 2019 (16 pages).
Dumoutier, Laure, et al. "Cloning and characterization of IL-10-related T cell-derived inducible factor (IL-TIF), a novel cytokine structurally related to IL-10 and inducible by IL-9." The Journal of Immunology 164.4 (2000): 1814-1819.
Fukui, H., et al. "IL-22 produced by cancer-associated fibroblasts promotes gastric cancer cell invasion via STAT3 and ERK signaling." British Journal of Cancer 111.4 (2014): 763-771.
Harrison, Charlotte. "IL-22: linking inflammation and cancer." Nature Reviews Drug Discovery 12.7 (2013): 505-505.
Kobold, Sebastian, et al. "Interleukin-22 Is Frequently Expressed in Small- and Large-Cell Lung Cancer and Promotes Growth in Chemotherapy-Resistant Cancer Cells." Journal of Thoracic Oncology 8.8 (2013): 1032-1042.

(Continued)

*Primary Examiner* — Dong Jiang
(74) *Attorney, Agent, or Firm* — Mendelsohn Dunleavy, P.C.

(57) ABSTRACT

An anti-IL-22 antibody or antibody fragment that binds to both human IL-22 and a mammalian IL-22 as well as modified anti-IL-22 antibodies and antibody fragments. Pharmaceutical compositions and kits comprising the antibody or antibody fragment are also provided. Also provided are methods for treatment of various IL-22 mediated conditions and diseases.

29 Claims, 18 Drawing Sheets
Specification includes a Sequence Listing.

(56) References Cited

OTHER PUBLICATIONS

Kumar, Pawan, et al. "IL-22: An Evolutionary Missing-Link Authenticating the Role of the Immune System in Tissue Regeneration." Journal of Cancer 4.1 (2013): 57-65.
Lim, Chrissie, et al. "The role of the IL-22/IL-22R1 axis in cancer." Cytokine & Growth Factor Reviews 25.3 (2014): 257-271.
Zheng, Yan, et al. "Interleukin-22 mediates early host defense against attaching and effacing bacterial pathogens." Nature Medicine 14.3 (2008): 282-289.
Extended European Search Report for corresponding European application No. 19816016.0; dated Jun. 15, 2022 (13 pages).
Hao, Ji-Qing. "Targeting Interleukin-22 in Psoriasis." Inflammation 37.1 (2014): 94-99.
Ouyang, Wenjun. "Distinct roles of IL-22 in human psoriasis and inflammatory bowel disease." Cytokine & Growth Factor Reviews 21.6 (2010): 435-441.
Ma, Hak-Ling, et al. "IL-22 is required for Th17 cell-mediated pathology in a mouse model of psoriasis-like skin inflammation." The Journal of Clinical Investigation 118.2 (2008): 597-607.
Written Opinion for corresponding Singaporean application No. 11202012014U; dated Aug. 2, 2022 (7 pages).
Notice of Examinaton for corresponding Taiwanese application No. 108119613; dated Feb. 10, 2023 (16 pages) Machine Translation.
Office Action for corresponding Canadian application No. 3,102,391; dated May 3, 2023 (7 pages).
Notice of Reasons for Rejection for corresponding Japanese application No. 2021-518032; dated May 30, 2023 (8 pages) Machine Translation.
First Office Action for corresponding Chinese application No. 201980038826.8; dated Aug. 5, 2023 (16 pages) Machine Translation.

```
              10        20        30        40        50
         ....|....|....|....|....|....|....|....|....|....|.
hum10-LC AIQLTQSPSSLSASVGDRVTITCSASSSVSYMHWYLQKPGQSPQLLIYETSI LC-CPS-03 ..................................................K..
LC-CPS-04 ...................................................R
LC-CPS-05 ......................................................
LC-CPS-06 ..................................................K.R
LC-CPS-07 ..................................................K..
LC-CPS-11 ..........................K........................R
```

FIG. 2A

SEQ ID NO:

```
    50        60        70        80        90       100
    |....|....|....|....|....|....|....|....|....|....|....|...
    TSKLASGVPSRFSGSGSGTDFTFTISSLEAEDAATYYCQQWSSNPYITFGQGTKVEIKR   19

```
              10        20        30        40        50        60
         ....|....|....|....|....|....|....|....|....|....|....|....|.
hum10-HC QVQLVQSGAEVKKPGASVKVSCKASGYIFTSYWIHWIRQPPGKGLEWIGRIYPGTGNTYYN
HC-CPS-08 ..............................R............................R....
HC-CPS-09 ..............................R..................................
HC-CPS-25 ..............................R............................R....
HC-CPS-31 .............................................................R....
HC-CPS-49 ..............................R..................................
HC-CPS-50 ..............................R..................................
```

FIG. 3A

```
     60        70        80        90        100       110          SEQ ID
     |....|....|....|....|....|....|....|....|....|....|....|....|..  NO:
     YNEKFKGRVTISADKSISTAYLQWSSLKASDTAMYYCARSYDSSCAYWGQGTLVTVSS         20
     .......................................................V.........   13
     ..R....................................................V.........   14
     .....................................................Y.V.........   15
     ..R..................................................Y.V.........   16
     ..R.................................................MY.V.........   17
     ..R..................................................M..VG........   18
```

FIG. 3B

ANTI-IL-22 ANTIBODIES, ANTIBODY FRAGMENTS, THEIR IMMUNOCONJUGATES AND USES THEREOF

FIELD OF THE DISCLOSURE

This disclosure relates anti-IL-22 antibodies, antibody fragments, variants and immunoconjugates of such antibodies and antibody fragments and uses of the antibodies, antibody fragments, variants and immunoconjugates in diagnostic and therapeutic methods.

BACKGROUND OF THE DISCLOSURE

Interleukin-22 (IL-22), also known as interleukin-10 related T cell-derived inducible factor (IL-TIF), is a glycoprotein. IL-22 is mainly expressed in the thymus, the brain, activated T cells and mast cells, lectin-stimulated spleen cells, interleukin-2/interleukin-12-stimulated NK cells, and in a number of organs and tissues upon lipopolysaccharide (LPS) stimulation, including the gut, liver, stomach, kidney, lung, heart, thymus, and spleen. T cells are the main source of human IL-22 because human IL-22 mRNA is highly expressed in peripheral T cells and T cells activated by an anti-CD3 antibody or ConA. Activated T cells are mostly CD4+ cells.

The IL-22 precursor has 179 amino acid residues and the mature IL-22 protein has 146 amino acid residues. Dumoutier et al. cloned IL-22 genes of mouse and human (Dumoutier, et al., *J Immunol.*, vol. 164, pp. 1814-1819, 2000), and obtained two patents related to IL-22, U.S. Pat. Nos. 6,359,117 and 6,274,710. IL-22 accomplishes its biological function by binding to an IL-22R1 receptor and an IL-10R2 receptor. IL-22R1 is a receptor specific to IL-22 and is expressed in the skin, the kidney, the digestive system (pancreas, small intestine, liver, large intestine and colon), and the respiratory system (lungs and bronchi).

IL-22 plays an important role in mucosal immunity, mediating early host defense against attacking and effacing bacterial pathogens. See Zheng et al., *Nat. Med.*, vol. 14, pp. 282-289, 2008. IL-22 promotes the production of antimicrobial peptides and proinflammatory cytokines from epithelial cells. It also stimulates proliferation and migration of colonic epithelial cells in the gut. See Kumar et al., *J. Cancer*, vol. 4, pp. 57-65, 2013. Upon bacterial infection, IL-22 knock-out mice displayed impaired gut epithelial regeneration, high bacterial load and increased mortality. Kumar et al., supra. Similarly, infection of IL-22 knock-out mice with influenza virus resulted in severe weight loss and impaired regeneration of tracheal and bronchial epithelial cells. Thus, IL-22 plays a proinflammatory role in suppressing microbial infection as well as an anti-inflammatory protective role in epithelial regeneration in inflammatory responses.

In addition to its role in inflammatory responses, IL-22 has also been linked to cancers (Harrison, "IL-22: linking inflammation and cancer," *Nature Reviews Drug Discovery*, vol. 12, pp. 504-505, 2013). Specifically, Lim and Savan ("The role of the IL-22/IL-22R1 axis in cancer," *Cytokine Growth Factor Rev.*, vol. 25, pp. 257-271, 2014) discloses that the IL-22 signaling pathway orchestrates mucosal immune defense and tissue regeneration through pleiotropic effects including pro-survival signaling, cell migration, dysplasia and angiogenesis. These functions can be hijacked by aggressive cancers to enhance tumor growth and metastasis. Thus, the role of the IL-22 in cancer is complex and context-specific, as evidenced by dysregulation of IL-22 expression and signaling in patients with many common cancers including those of the gut, skin, lungs and liver.

Lanfranca et al. ("IL-22 promotes pancreatic cancer tumorigenesis through induction of stemness and epithelial to mesenchymal transition," *J Immunol.*, vol. 198, 1 Supplement, 66.22, 2017) discloses that IL-22 is integral in the initiation, progression and establishment of pancreatic cancer. Fukui et al. (*British Journal of Cancer*, vol. 111, pp. 763-771, 2014) finds that IL-22 produced by cancer-associated fibroblasts promotes gastric cancer cell invasion via STAT3 and ERK signaling. Kobold et al. (*J Thoracic Oncology*, vol. 8, pp. 1032-1042, 2013) discovered that IL-22 is preferentially expressed in small- and large-cell lung cancers. Enhanced IL-22-R1 expression and signaling in chemotherapy-refractory lung cancer cell lines are indicative of a protumorigenic function of IL-22 and may contribute to a more aggressive cancer phenotype.

IL-22 has been reported for treatment of human pancreatic disease. See e.g. U.S. Pat. No. 6,551,799). The use of IL-22 in reducing triglycerides in serum and treating obesity has also been reported. See e.g. WO 2006/073 508 and CN1679918. Anti-IL-22 antibodies have been developed for treatment of inflammatory related diseases. U.S. Pat. No. 7,901,684 discloses human antibodies and antigen binding fragments thereof that specifically bind to human IL-22. The antibodies are defined by the specific amino acid sequences of their $V_H$ and $V_L$ domains. The antibodies are said to act as antagonists of IL-22 activity, thereby modulating immune responses for treating inflammatory disorders, autoimmune diseases, allergies, septic shock, infectious disorders, transplant rejection, cancer, and other immune system disorders.

U.S. Pat. No. 7,811,567 discloses a method of treating IL-22-associated disorder by administering an antibody or its antigen-binding fragment that specifically binds to human IL-22. The antibody has a $V_H$ domain comprising three complementarity determining regions (CDRs) with specific amino acid sequences of SEQ ID NOS: 602, 603, and 604, and a $V_L$ domain comprising three CDRs with specific amino acid sequences of SEQ ID NOS: 605, 606, and 607.

U.S. Pat. No. 7,737,259 discloses compositions for the diagnosis and treatment of inflammatory disorders and autoimmune disorders. The compositions comprise an antibody that specifically binds to human IL-22. The antibody is (a) an antibody produced by a hybridoma selected from 3F11.3 (ATCC Accession No. PTA-7312), hybridoma 11H4.4 (ATCC Accession No. PTA-7315), and hybridoma 8E11.9 (ATCC Accession No. PTA-7319); (b) an affinity matured form of the antibody of (a); (c) an antigen-binding fragment of the antibody of (a) or (b); or (d) a humanized form of the antibody of (a), (b), or (c).

WO 2005/000897 discloses an isolated antibody and its antigen-binding fragment that specifically binds to IL-22. The antibody or fragment can reduce the binding of IL-22 to a complex comprising an IL-22 receptor (IL-22R) and interleukin-10 receptor 2 (IL-10R2). The antibody or its antigen-binding fragment may also reduce the direct interaction between IL-22 and an IL-22 receptor.

These antibodies were developed for binding to human IL-22 for treatment of diseases or disorders in humans. However, their binding to non-human mammalian IL-22, such as murine IL-22, was not measured or studied. An antibody intended to be used in humans to bind to human IL-22 must first be tested in animals for assessment of its safety and efficacy. To ensure that the animal testing is predictive of the safety and efficacy in humans, the antibody should ideally have a similar high binding affinity to both human IL-22 and at least the IL-22 of the test animal.

The present invention provides anti-IL-22 antibodies and their fragments that can bind to both human and mouse IL-22 with a high binding affinity, and which may be used to cause the same downstream biologic effects in both human and murine biologic systems.

SUMMARY OF THE DISCLOSURE

In one aspect, the present invention provides an anti-IL-22 antibody or antibody fragment comprising:
a light chain variable region including a light chain CDR1 having an amino acid sequence selected from SASSSVSX$_1$MH (SEQ ID NO:1), a light chain CDR2 having an amino acid sequence selected from X$_2$TX$_3$KLX$_4$S (SEQ ID NO:2), and a light chain CDR3 having an amino acid sequence of QQWSSNPYIT (SEQ ID NO:3); and
a heavy chain variable region including a heavy chain CDR1 having an amino acid sequence selected from GYIFX$_5$SYWIH (SEQ ID NO:4), a heavy chain CDR2 having an amino acid sequence selected from RIYPGTGX$_6$TYYNX$_7$KFKG (SEQ ID NO:5), and a heavy chain CDR3 having an amino acid sequence selected from SYX$_8$X$_9$SVX$_{10}$Y (SEQ ID NO:6),
wherein X$_1$ is Y or K, X$_2$ is E or K, X$_3$ is S or R, X$_4$ is A or L, X$_5$ is T or R, X$_6$ is N or R, X$_7$ is E or R, X$_8$ is D or M, X$_9$ is S or Y, and X$_{10}$ is A or G.

In the previous embodiment, the light chain variable region may have an amino acid sequence selected from SEQ ID NOS: 7-12, and the heavy chain variable region has an amino acid sequence selected from SEQ ID NOS: 13-18.

In any one of the previous embodiments, the antibody or antibody fragment may be selected from:
an antibody or antibody fragment comprising a light chain variable region having an amino acid sequence of SEQ ID NO: 7 and a heavy chain variable region having an amino acid sequence of SEQ ID NO: 13;
an antibody or antibody fragment comprising a light chain variable region having an amino acid sequence of SEQ ID NO: 10 and a heavy chain variable region having an amino acid sequence of SEQ ID NO: 13;
an antibody or antibody fragment comprising a light chain variable region having an amino acid sequence of SEQ ID NO: 11 and a heavy chain variable region having an amino acid sequence of SEQ ID NO: 14;
an antibody or antibody fragment comprising a light chain variable region having an amino acid sequence of SEQ ID NO: 8 and a heavy chain variable region having an amino acid sequence of SEQ ID NO: 15;
an antibody or antibody fragment comprising a light chain variable region having an amino acid sequence of SEQ ID NO: 9 and a heavy chain variable region having an amino acid sequence of SEQ ID NO: 15;
an antibody or antibody fragment comprising a light chain variable region having an amino acid sequence of SEQ ID NO: 10 and a heavy chain variable region having an amino acid sequence of SEQ ID NO: 15;
an antibody or antibody fragment comprising a light chain variable region having an amino acid sequence of SEQ ID NO: 8 and a heavy chain variable region having an amino acid sequence of SEQ ID NO: 16;
an antibody or antibody fragment comprising a light chain variable region having an amino acid sequence of SEQ ID NO: 7 and a heavy chain variable region having an amino acid sequence of SEQ ID NO: 17;
an antibody or antibody fragment comprising a light chain variable region having an amino acid sequence of SEQ ID NO: 8 and a heavy chain variable region having an amino acid sequence of SEQ ID NO: 17; and
an antibody or antibody fragment comprising a light chain variable region having an amino acid sequence of SEQ ID NO: 12 and a heavy chain variable region having an amino acid sequence of SEQ ID NO: 18.

In any one of the previous embodiments, the antibody or antibody fragment may bind to human IL-22 and a mammalian non-human IL-22.

In the previous embodiment, the mammalian IL-22 may be mouse IL-22.

In any one of the previous two embodiments, the antibody or antibody fragment may bind to the human IL-22 and the mammalian IL-22 with affinities within ±20%, ±15%, ±10% or ±5% of each other.

In any one of the previous embodiments, the antibody or antibody fragment may be capable of inhibiting phosphorylation of Stat3.

In any one of the previous embodiments, the antibody or antibody fragment may be capable of inhibiting IL-22-induced cytokine production.

In any one of the previous embodiments, the antibody or antibody fragment may be capable of inhibiting an immune response in at least one animal or human.

In the previous embodiment, the at least one animal may comprise a mammal.

In any one of the previous two embodiments, mammal may be a mouse.

In any one of the previous embodiments, the anti-IL-22 antibody or antibody fragment may be humanized.

In any one of the previous embodiments, the anti-IL-22 antibody or antibody fragment may comprise a modified Fc region.

In another aspect, the present invention provides a modified anti-IL-22 antibody or antibody fragment comprising the anti-IL-22 antibody or antibody fragment of any one of the previous embodiments and at least one moiety selected from oligosaccharides, non-proteinaceous moieties, a therapeutic agent, a prophylactic agent and a diagnostic agent.

In the previous embodiment, the at least one moiety may be an oligosaccharide, at least one non-proteinaceous moiety, or selected from a therapeutic agent, a prophylactic agent and a diagnostic agent.

In the previous embodiment, the at least one non-proteinaceous moiety may be selected from soluble polymers.

In any one of the previous two embodiments, the modified anti-IL-22 antibody or antibody fragment may comprise two agents selected from therapeutic agents, prophylactic agents and diagnostic agents.

In any one of the previous three embodiments, the antibody or antibody fragment and the therapeutic, prophylactic agent or diagnostic agent may be covalently bonded to a linker molecule.

In another aspect, the present invention provides pharmaceutical composition comprising the antibody or antibody fragment or the modified anti-IL-22 antibody or antibody fragment of any one of previous embodiments, and a pharmaceutically acceptable carrier.

In the previous embodiment, the pharmaceutical composition may comprise at least one additional excipient.

In any one of previous two embodiments, the pharmaceutical composition may further comprise at least one additional therapeutic agent, and/or a pharmaceutically acceptable preservative.

In another aspect, the present invention provides a method of treating an immune-related disease or cancer comprising a step of administering the antibody or antibody fragment, the modified anti-IL-22 antibody or antibody fragment, or the pharmaceutical composition of any one of the previous embodiments, to a subject.

In another aspect, the present invention provides a kit for diagnosis or treatment, said kit comprising the antibody or antibody fragment, the modified anti-IL-22 antibody or antibody fragment, or the pharmaceutical composition of any one of previous embodiments; and instructions for using the antibody or antibody fragment, the modified the antibody or antibody fragment, or the pharmaceutical composition for diagnosis or treatment.

In another aspect, the present invention provides an antibody or antibody fragment comprising a light chain variable region having an amino acid sequence that has at least 90% sequence identity to one of amino acid sequences with SEQ ID NOS: 7-12; and a heavy chain variable region having an amino acid sequence that has at least 90% sequence identity to one of amino acid sequences with SEQ ID NOS: 13-18.

In the previous embodiment, the light chain variable region may have three complementarity determining regions that are identical to complementarity determining regions of a light chain variable region having an amino acid sequence selected from SEQ ID NOS: 7-12.

In any one of the previous two embodiments, the heavy chain variable region may be three complementarity determining regions that are identical to complementarity determining regions of a heavy chain variable region having an amino acid sequence selected from SEQ ID NOS: 13-18.

In any one of the previous three embodiments, the light and heavy chains may have at least 95% sequence identity, at least 98% sequence identity, or at least 99% sequence identity.

BRIEF DESCRIPTION OF THE DRAWINGS

FIGS. 2A-2B show sequence alignments of the light chains of hum10 and antibodies of the present invention.

FIGS. 3A-3B show sequence alignments of the heavy chains of hum10 and antibodies of the present invention.

DEFINITIONS

Figure 1:
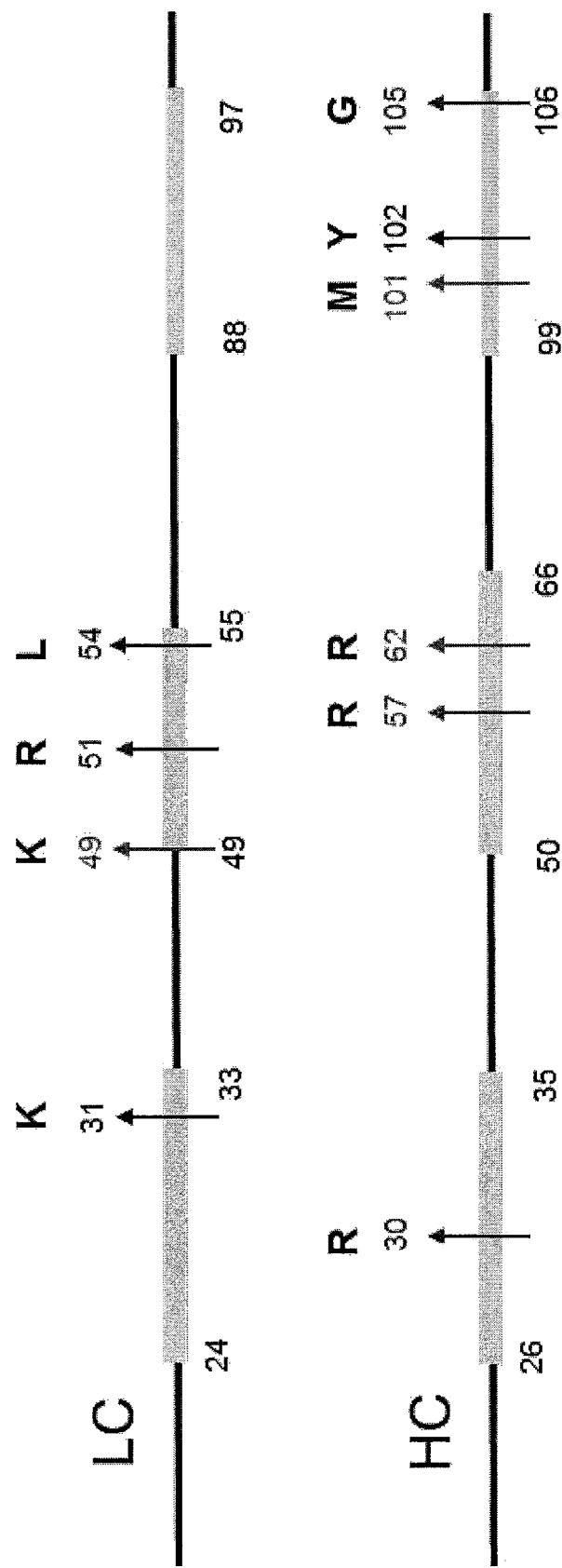
FIG. 1 shows the structure of the light and heavy chains of a humanized monoclonal antibody against human IL-22 (hum10) that was used as the parent antibody to evolve the antibodies of the present invention. The CDRs are shown as thicker portions in the diagrams with their starting and ending positions in the light and heavy chains labelled. Some of the mutations and their positions in the CDRs that were made to the parent antibody to provide antibodies of the present invention are labeled within the CDRs.

In order to facilitate understanding of the examples provided herein, certain frequently occurring terms are defined herein.

In connection with a measured quantity, the term "about" as used herein refers to the normal variation in that measured quantity that would be expected by a skilled person making the measurement and exercising a level of care commensurate with the objective of the measurement and the precision of the measuring equipment used. Unless otherwise indicated, "about" refers to a variation of +/−10% of the value provided.

The term "affinity" or "binding affinity" as used herein refers to the strength of the sum total of noncovalent interactions between a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

The term "amino acid" as used herein refers to any organic compound that contains an amino group (—$NH_2$) and a carboxyl group (—COOH), may either as free groups or alternatively after condensation as part of peptide bonds. The "twenty naturally occurred amino acids" are understood in the art and refer to: alanine (ala or A), arginine (arg or R), asparagine (asn or N), aspartic acid (asp or D), cysteine (cys or C), glutamic acid (glu or E), glutamine (gln or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V), which are building blocks of natural proteins.

The term "antibody" as used herein refers to intact immunoglobulin molecules, as well as fragments of immunoglobulin molecules, such as Fab, Fab', (Fab')$_2$, Fv, and single chain antibody (SCA or scFv) fragments, that are capable of binding to an epitope of an antigen. These antibody fragments, which retain some ability to selectively bind to an antigen (e.g., a polypeptide antigen) of the antibody from which they are derived, can be made using well known methods in the art, and are described further, as follows. Antibodies useful in the practice of the claimed invention may be IgG1, IgG2, IgG3, IgG4, IgM, IgA1, IgA2, sIgA, IgD or IgE. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like. Chimeric, human-like, humanized or fully human antibodies are particularly useful for administration to human patients.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')$_2$ fragment is a dimer of two Fab' fragments, held together by two disulfide bonds.

An Fv fragment is defined as a genetically engineered fragment containing the variable region of a light chain and the variable region of a heavy chain expressed as two chains.

A single chain antibody ("SCA" or scFv) is a genetically engineered single chain molecule containing the variable region of a light chain and the variable region of a heavy chain, linked by a suitable, flexible polypeptide liner, and which may include additional amino acid sequences at the amino- and/or carboxyl-termini. For example, a single chain antibody may include a tether segment for linking to the encoding polynucleotide. A functional single chain antibody generally contains a sufficient portion of the variable region of a light chain and a sufficient region of the variable region of a heavy chain so as to retain the property of a full-length antibody for binding to a specific target molecule or epitope The term "antibody fragment" as used herein refers to a molecule other than an intact antibody and comprising a portion of an intact antibody that binds the antigen to which the intact antibody binds. Examples of antibody fragments include but are not limited to Fv, Fab, Fab', Fab'-SH, F(ab')$_2$; diabodies; linear antibodies; monovalent antibody, single-chain antibody molecules (e.g. scFv). These antibody fragments, which retain some ability to selectively bind to an antigen (e.g., a polypeptide antigen) of the antibody from which they are derived, can be made using well known methods in the art.

The terms "anti-IL-22 antibody," "anti-IL-22 antibody fragment" and "an antibody or antibody fragment that binds to IL-22" are used interchangeably herein and refer to an antibody or antibody fragment that is capable of binding at least one epitope of IL-22 protein with sufficient affinity such that the antibody or antibody fragment is useful as a diagnostic, prophylactic and/or therapeutic agent in targeting IL-22. In one embodiment, the extent of binding of an anti-IL-22 antibody or antibody fragment to an unrelated, non-IL-22 protein is less than about 5%, or less than about 10%, or less than about 20% or less than about 50% of the binding of the antibody or antibody fragment to IL-22 as measured by ELISA. In certain embodiments, the antibody or antibody fragment that binds to IL-22 has a dissociation constant (Kd) of ≤1 μM, or ≤100 nM, or ≤10 nM, or ≤1 nM, or ≤0.1 nM, or ≤0.01 nM, or ≤0.001 nM (e.g. $10^{-8}$ M or less, or from $10^{-8}$ M to $10^{-13}$ M, or from $10^{-9}$ M to $10^{-13}$ M). In certain embodiments, an anti-IL-22 antibody or antibody fragment binds to an epitope of IL-22 that is conserved among IL-22 from different species.

The term "arthritis" as used herein refers to inflammation of the joints and includes, but is not limited to, osteoarthritis, gout, infection-associated arthritis, Reiter's syndrome arthritis, and arthritis associated with autoimmune disorders, such as rheumatoid arthritis, psoriatic arthritis, lupus-associated arthritis, spondylarthritis, and scleroderma-associated arthritis. The term "arthritic inflammation" refers to inflammation associated with arthritis.

The term "autoimmune disorder" or "autoimmunity" as used herein refers to any condition in which a humoral or cell-mediated immune response is mounted against a body's own tissue. An "IL-22 mediated autoimmune disorder" is any autoimmune disorder that is caused by, maintained, or exacerbated by IL-22 activity. The term "autoimmune inflammation" refers to inflammation associated with an autoimmune disorder.

The term "binding" as used herein refers to interaction of the variable region or an Fv of an antibody with an antigen with the interaction depending upon the presence of a particular structure (e.g., an antigenic determinant or epitope) on the antigen. For example, an antibody variable region or Fv recognizes and binds to a specific protein structure rather than to proteins generally. As used herein, the term "specifically binding" or "binding specifically" means that an antibody variable region or Fv binds to or associates with more frequently, more rapidly, with greater duration and/or with greater affinity with a particular antigen than with other proteins. For example, an antibody variable region or Fv specifically binds to its antigen with greater affinity, more readily, and/or with greater duration than it binds to other antigens. As another example, an antibody variable region or Fv binds to a cell surface protein (antigen) with materially greater affinity than it does to related proteins or other cell surface proteins or to antigens commonly recognized by polyreactive natural antibodies (i.e., by naturally occurring antibodies known to bind a variety of antigens naturally found in humans). However, "specifically binding" does not necessarily require exclusive binding or non-detectable binding of another antigen, this is meant by the term "selective binding". In one example, "specific binding" of an antibody variable region or Fv (or other binding region) to an antigen, means that the antibody variable region or Fv binds to the antigen with an equilibrium constant (KD) of 100 nM or less, such as 50 nM or less, for example 20 nM or less, 15 nM or less, or 10 nM or less, or 5 nM or less, 2 nM or less, or 1 nM or less.

The terms "cancer" and "cancerous" as used herein refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The terms "cell proliferative disorder" and "proliferative disorder" as used herein refer to disorders that are associated with some degree of abnormal cell proliferation. In one embodiment, the cell proliferative disorder is cancer.

The term "chemotherapeutic agent" as used herein refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolmelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (see, e.g., Nicolaou et al., Angew. Chem. Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylomithine (DMF®); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

The term "chimeric" antibody as used herein refers to an antibody in which a portion of the heavy and/or light chain is derived from a particular source or species, while the remainder of the heavy and/or light chain is derived from a different source or species.

The term "chronic" administration as used herein refers to administration of an agent(s) in a continuous mode as opposed to an acute mode, so as to maintain the initial therapeutic effect for an extended period of time. "Intermittent" administration is treatment that is not consecutively done without interruption, but rather is cyclic in nature.

The term "chronic inflammation" as used herein refers to inflammation in which the cause of the inflammation persists and is difficult or impossible to remove.

The term "constitutive" as used herein, as for example applied to IL-22 activity, refers to continuous signaling activity that is not dependent on the presence of a ligand or other activating molecules. Some of the IL-22 activity may be constitutive or the activity may be further activated by the binding of other molecules (e.g. ligands). Cellular events that lead to activation of IL-22 activity are well known among those of ordinary skill in the art. For example, activation may include oligomerization, e.g., dimerization, trimerization, etc., into higher order receptor complexes. Complexes may comprise a single species of protein, i.e., a homomeric complex. Alternatively, complexes may comprise at least two different protein species, i.e., a heteromeric complex. Complex formation may be caused by, for example, overexpression of normal or mutant forms of receptor on the surface of a cell. Complex formation may also be caused by a specific mutation or mutations in a receptor.

The term "detectable label" as used herein refers to any substance whose detection or measurement, either directly or indirectly, by physical or chemical means, is indicative of the presence of the IL-22 in a sample. The detectable label may be detectable by itself (e.g. radioisotope labels or fluorescent labels) or, in the case of an enzymatic label, may catalyze chemical alteration of a substrate compound or composition, resulting in a detectable product. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

The term "diabodies" as used herein refers to small antibody fragments with two antigen-binding sites, which fragments comprise a heavy-chain variable region ($V_H$) connected to a light-chain variable region ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/001161; Hudson et al. *Nat. Med.*, vol. 9, pp. 129-134, 2003; and Hollinger et al., *Proc. Natl. Acad. Sci. USA* vol. 90, pp. 6444-6448 1993. Triabodies and tetrabodies are also described in Hudson et al. *Nat. Med.*, vol. 9, pp. 129-134, 2003.

The term "diagnostics" as used herein refers to determination of a subject's susceptibility to a disease or disorder, determination as to whether a subject is presently affected by a disease or disorder, prognosis of a subject affected by a disease or disorder (e. g., identification of pre-metastatic or metastatic cancerous states, stages of cancer, or responsiveness of cancer to therapy), and therametrics (e. g., monitoring a subject's condition to provide information as to the effect or efficacy of therapy). In some embodiments, the diagnostic method of this invention is particularly useful in detecting early stage cancers.

The term "diagnostic agent" as used herein refers to a molecule which can be directly or indirectly detected and is used for diagnostic purposes. The diagnostic agent may be administered to a subject or a sample. The diagnostic agent can be provided per se or may be conjugated to a vehicle such as a conditionally active antibody.

The term "effective amount" of the anti-IL-22 antibody or antibody fragment as used herein means a sufficient amount of the antibody or antibody fragment to treat a disease or illness, at a reasonable benefit/risk ratio applicable to any medical treatment. It will be understood, however, that the total daily usage of the antibodies or antibody fragments and compositions of the present invention will be decided by the attending physician within the scope of sound medical judgment. The specific therapeutically effective dose level for any particular patient will depend upon a variety of factors including the disorder being treated and the severity of the disorder; activity of the specific antibody or antibody fragment employed; the specific composition employed, the age, body weight, general health, sex and diet of the patient; the time of administration, route of administration, and rate of excretion of the specific antibody or antibody fragment employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved.

The term "effector function" as used herein refers to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" as used herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The term "framework region" or "FR" as used herein refers to variable region residues other than the residues in the CDRs. The FR of a variable region generally consists of four FR domains: FR1, FR2, FR3, and FR4. Accordingly, the CDR and FR sequences generally appear in the following sequence in the variable regions: FR1-CDR1-FR2-CDR2-FR3-CDR3-FR4.

The term "full length antibody," "intact antibody," or "whole antibody" refers to an antibody which comprises an antigen-binding variable region ($V_H$ or $V_L$) as well as a light chain constant domain (CL) and heavy chain constant domains, CH1, CH2 and CH3. The constant domains may be native sequence constant domains (e.g. human native sequence constant domains) or amino acid sequence variants thereof. Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

The terms "host cell," "host cell line," and "host cell culture" as used herein are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "humanized" antibody as used herein refers to a chimeric antibody comprising amino acid residues from non-human CDRs and amino acid residues from human framework regions. In certain embodiments, a humanized antibody will comprise substantially all of at least one, and typically two, variable regions, in which all or substantially all of the CDRs correspond to those of a non-human antibody, and all or substantially all of the FRs correspond to those of a human antibody. A humanized antibody optionally may comprise at least a portion of an antibody constant region derived from a human antibody. The term "human consensus framework" as used herein is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable region sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the $V_L$, the subgroup is subgroup kappa I as in Kabat et al., supra. In one embodiment, for the $V_H$, the subgroup is subgroup III as in Kabat et al., supra. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

The term "IL-22" as used herein refers to any native IL-22 from any vertebrate source, including mammals such as primates (e.g. humans) and rodents (e.g., mice and rats), unless otherwise indicated. The term encompasses "full-length," unprocessed precursor IL-22 as well as any form of IL-22 that results from processing in the human or animal body. The term also encompasses naturally occurring variants of IL-22, e.g., splice variants or allelic variants. The amino acid sequence of human IL-22 is well-known in the art and available from public databases such as GenBank.

The term "IL-22 associated activity" as used herein refers to one or more of the biological activities of IL-22, including, but not limited to, (1) interacting with, e.g., binding to, an IL-22 receptor (e.g., an IL-22R or IL-10R2 or a complex thereof, such as a mammalian, e.g., murine or human origin); (2) associating with one or more signal transduction molecules; (3) stimulating phosphorylation and/or activation of a protein kinase, e.g., JAK/STAT3, ERK, and MAPK; (4) modulating, e.g., stimulating or decreasing, proliferation, differentiation, effector cell function, cytolytic activity, cytokine or chemokine secretion, and/or survival of an IL-22 responsive cell, e.g., an epithelial cell from, e.g., kidney, liver, colon, small intestine, thyroid gland, pancreas, skin); (5) modulating at least one parameter of an acute phase response, e.g., a metabolic, hepatic, hematopoietic (e.g., anemia, platelet increase) or neuroendocrine change, or a change (e.g., increase or decrease in an acute phase protein, e.g., an increase in fibrinogen and/or serum amyloid A, or a decrease in albumin); and/or (6) modulating at least one parameter of an inflammatory state, e.g., modulating cytokine-mediated proinflammatory actions (e.g., fever, and/or prostaglandin synthesis, for example PGE2 synthesis), modulating cellular immune responses, modulating cytokine, chemokine (e.g., GRO1), or lymphokine production and/or secretion (e.g., production and/or secretion of a proinflammatory cytokine).

The term "immune related disease" as used herein refers to a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, and neoplasia.

The term "immunoconjugate" as used herein is an antibody conjugated to one or more heterologous molecule(s), including but not limited to a cytotoxic agent.

The term "individual" or "subject" as used herein refers to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "inflammation" as used herein refers to the accumulation of leukocytes and the dilation of blood vessels at a site of injury or infection, typically causing pain, swelling, and redness.

The term "inflammatory bowel disease" or "IBD" as used herein refers to a chronic disorder characterized by inflammation of the gastrointestinal tract. IBD encompasses ulcerative colitis, which affects the large intestine and/or rectum, and Crohn's disease, which may affect the entire gastrointestinal system but more commonly affects the small intestine (ileum) and possibly the large intestine.

The term "inhibiting cell growth or proliferation" as used herein means decreasing a cell's growth or proliferation by at least 10%, or at least 20%, or at least 30%, or at least 40%, or at least 50%, or at least 60%, or at least 70%, or at least 80%, or at least 85%, or at least 90%, or at least 95%, or at least 98%, or at least 99% or 100%, and includes inducing cell death.

The term "isolated" or "purified" antibody as used herein refers to an antibody that has been identified and separated and/or recovered from a component of its natural environment. Contaminant components of its natural environment are materials which would interfere with diagnostic, prophylactic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, or more than 99% by weight, (2) to a degree sufficient to obtain at least 15 residues of an N-terminal or internal amino acid sequence by use of a spinning cup sequenator, or (3) to homogeneity by SDS-PAGE gel under reducing or nonreducing conditions using Coomassie blue or, silver stain. Isolated antibody includes the antibody in situ within recombinant cells since at least one component of the antibody's natural environment will not be present. Ordinarily, however, isolated antibody will be prepared by at least one purification step.

The term "liposome" as used herein is a small vesicle composed of various types of lipids, phospholipids and/or surfactant which is useful for delivery of a drug (such as a nucleic acid, polypeptide, antibody, agonist or antagonist) to a mammal, such as human, primate or mouse. The components of the liposome are commonly arranged in a bilayer formation, similar to the lipid arrangement of biological membranes.

The term "package insert" as used herein is used to refer to instructions customarily included in commercial packages of therapeutic products, that contain information about the indications, usage, dosage, administration, combination therapy, contraindications and/or warnings concerning the use of such therapeutic products.

The term "percent (%) amino acid sequence identity" with respect to a reference polypeptide sequence as used herein is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100*(X/Y)$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical composition" as used herein refers to a preparation which is in such form as to permit the biological activity of the anti-IL-22 antibody contained therein to be effective, and which contains no additional components which are unacceptably toxic to a subject to which the composition would be administered.

The term "pharmaceutically acceptable carrier" as used herein refers to an ingredient in a pharmaceutical composition, other than an active ingredient, which is nontoxic to a subject being exposed thereto at the dosages and concentrations employed. A pharmaceutically acceptable carrier includes, but is not limited to, a buffer, excipient, stabilizer, or preservative.

Examples of pharmaceutically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "psoriasis" as used herein refers to a condition characterized by the eruption of circumscribed, discreet and confluent, reddish, silvery-scaled macropapules preeminently on the elbows, knees, scalp or trunk.

The term "recombinant antibody" as used herein refers to an antibody (e.g. a chimeric, humanized, or human antibody or antigen-binding fragment thereof) that is expressed by a recombinant host cell comprising nucleic acid encoding the antibody. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia coli* cells or *Bacillus subtilis* cells, etc.

The term "single chain Fv" ("scFv") as used herein is a covalently linked $V_H::V_L$ heterodimer which is usually expressed from a gene fusion including $V_H$ and $V_L$ encoding genes linked by a peptide-encoding linker. "dsFv" is a $V_H:V_L$ heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "treatment," "treat," or "treating" as used herein refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or antibody fragments of the invention are used to delay development of a disease or to slow the progression of a disease.

The term "tumor" as used herein refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as ref/erred to herein.

The term "variable region" or "variable domain" of an antibody as used herein interchangeably refers to the amino-terminal domains of the heavy or light chain of the antibody. The variable region of the heavy chain may be referred to as "$V_H$." The variable region of the light chain may be referred to as "$V_L$." These variable regions are generally the most variable parts of an antibody and contain the antigen-binding sites. The variable regions of the heavy chain and light chain generally have similar structures, with each domain comprising four conserved framework regions (FRs) and three CDRs. (See, e.g., Kindt et al. *Kuby Immunology*, 6th ed., W.H. Freeman and Co., page 91 (2007).) A single $V_H$ or $V_L$ region may be sufficient to confer antigen-binding specificity. Furthermore, antibodies or antibody fragments that bind a particular antigen may be isolated using a $V_H$ or $V_L$ region from an antibody that binds the antigen to screen a library of complementary $V_L$ or $V_H$ domains, respectively. See, e.g., Portolano et al., *J. Immunol.*, vol. 150, pp. 880-887, 1993; Clarkson et al., *Nature*, vol. 352, pp. 624-628, 1991.

The term "vector" as used herein refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

DETAILED DESCRIPTION

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component(s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

A. Anti-IL-22 Antibodies or Antibody Fragments

In one aspect, the present invention provides an anti-IL-22 antibody or antibody fragment that includes:

a light chain variable region including LC-CDR1 having an amino acid sequence selected from SASSSVSX$_1$MH (SEQ ID NO:1), LC-CDR2 having an amino acid sequence selected from X$_2$TX$_3$KLX$_4$S (SEQ ID NO:2), and LC-CDR3 having an amino acid sequence of QQWSSNPYIT (SEQ ID NO:3); and a heavy chain variable region including HC-CDR1 having an amino acid sequence selected from GYIFX$_5$SYWIH (SEQ ID NO:4), HC-CDR2 having an amino acid sequence selected from RIYPGTGX$_6$TYYNX$_7$KFKG (SEQ ID NO:5), and HC-CDR3 having an amino acid sequence selected from SYX$_8$X$_9$SVX$_{10}$Y (SEQ ID NO:6), wherein X$_1$ is Y or K, X$_2$ is E or K, X$_3$ is S or R, X$_4$ is A or L, X$_5$ is T or R, X$_6$ is N or R, X$_7$ is E or R, X$_8$ is D or M, X$_9$ is S or Y, and X$_{10}$ is A or G.

In another aspect, the anti-IL-22 antibody or antibody fragment of the invention comprises a light chain variable region having an amino acid sequence selected from SEQ ID NOS: 7-12, and a heavy chain variable region having an amino acid sequence selected from SEQ ID NOS: 13-18.

In yet another aspect, the anti-IL-22 antibody or antibody fragment of the invention is selected from:

(1) an antibody or antibody fragment including a light chain variable region having an amino acid sequence of SEQ ID NO: 7 and a heavy chain variable region having an amino acid sequence of SEQ ID NO: 13;

(2) an antibody or antibody fragment including a light chain variable region having an amino acid sequence of SEQ ID NO: 10 and a heavy chain variable region having an amino acid sequence of SEQ ID NO: 13;

(3) an antibody or antibody fragment including a light chain variable region having an amino acid sequence of SEQ ID NO: 11 and a heavy chain variable region having an amino acid sequence of SEQ ID NO: 14;

(4) an antibody or antibody fragment including a light chain variable region having an amino acid sequence of SEQ ID NO: 8 and a heavy chain variable region having an amino acid sequence of SEQ ID NO: 15;

(5) an antibody or antibody fragment including a light chain variable region having an amino acid sequence of SEQ ID NO: 9 and a heavy chain variable region having an amino acid sequence of SEQ ID NO: 15;

(6) an antibody or antibody fragment including a light chain variable region having an amino acid sequence of SEQ ID NO: 10 and a heavy chain variable region having an amino acid sequence of SEQ ID NO: 15;

(7) an antibody or antibody fragment including a light chain variable region having an amino acid sequence of SEQ ID NO: 8 and a heavy chain variable region having an amino acid sequence of SEQ ID NO: 16;

(8) an antibody or antibody fragment including a light chain variable region having an amino acid sequence of SEQ ID NO: 7 and a heavy chain variable region having an amino acid sequence of SEQ ID NO: 17;

(9) an antibody or antibody fragment including a light chain variable region having an amino acid sequence of SEQ ID NO: 8 and a heavy chain variable region having an amino acid sequence of SEQ ID NO: 17; and

(10) an antibody or antibody fragment including a light chain variable region having an amino acid sequence of SEQ ID NO: 12 and a heavy chain variable region having an amino acid sequence of SEQ ID NO: 18.

The anti-IL-22 antibodies or antibody fragments of the present invention are derived from a parent antibody that binds to human IL-22, referred to herein as hum10, which has a light chain variable region having an amino acid sequence of SEQ ID NO: 19 and a heavy chain variable region having an amino acid sequence of SEQ ID NO:20. The parent antibody hum10 is a humanized monoclonal antibody (mAb) generated from a functional hybridoma clone 3C3 by immunizing mice with human IL-22 (hIL-22). The binding affinity of the murine monoclonal antibody 3C3 to hIL-22 is approximately 100 pM (measured by SPR analysis). However, 3C3 mAb is not able to bind to mouse IL-22 (mIL-22). The 3C3 mAb is able to block the induction of Stat3 phosphorylation by hIL2 in HepG2 cells. The 3C3 mAb was humanized to become the humanized antibody hum10.

The parent antibody hum10 has been mutated to generate mutant antibodies including anti-IL-22 antibodies that are able to bind to both human IL-22 and mouse IL-22 with high affinity. Human and mouse IL-22 have some regions that are completely conserved. A CPE™ library was constructed from the parent antibody hum10 by substituting the amino acid residues at each position in all six CDRs of the hum10 with at least 15 other amino acids. Some examples of substitutions are shown in FIG. 1 where the CDRs are represented by the thicker portions of the diagram. The CPE™ library contains a total of 1068 CPE antibody mutants, 472 mutants with mutation in the light chain CDRs and 596 mutants with mutations in the heavy chain CDRs.

The mutant antibodies were expressed in a eukaryotic cell host, such as CHO cells. The sequence of each mutant antibody was verified and the mutant antibodies were arrayed in 96-well format.

The CPE™ library was screened for mutant antibodies that bind to both mouse IL-22 and human IL-22 with a high affinity. 10 antibodies satisfying the selection criteria were identified and are shown in Table 1 below.

TABLE 1

Top 10 Mutant Antibodies That Bind to Both Human and Mouse IL-22

| Top 10 clones | Light chain | Heavy Chain |
|---|---|---|
| CPS-01 | LC-03 | HC-08 |
| CPS-02 | LC-06 | HC-08 |
| CPS-04 | LC-07 | HC-09 |
| CPS-09 | LC-04 | HC-25 |
| CPS-10 | LC-05 | HC-25 |
| CPS-11 | LC-06 | HC-25 |
| CPS-14 | LC-04 | HC-31 |
| CPS-16 | LC-03 | HC-49 |
| CPS-17 | LC-04 | HC-49 |
| CPS-20 | LC-11 | HC-50 |

Among the 10 mutant antibodies listed in Table 1, there are six different light chains. The alignments of these six different light chains with the light chain of hum10 is shown in FIGS. 2A-2B. Among the 10 mutant antibodies listed in Table 1, there are six different heavy chains. The alignment of these six different heavy chains with the heavy chain of hum10 is shown in FIGS. 3A-3B. It is observed that the amino acid substitutions in the ten mutant antibodies occur in several specific positions in the CDRs.

The 10 antibodies of Table 1 were expressed in the same eukaryotic cell host to produce the antibodies for further testing, clinical trials, and/or therapeutic, prophylactic or diagnostic use. The eukaryotic cell host may be selected from 3T3 mouse fibroblast cells; BHK21 Syrian hamster fibroblast cells; MDCK, dog epithelial cells; HeLa human epithelial cells; PtK1 rat kangaroo epithelial cells; SP2/0 mouse plasma cells; and NS0 mouse plasma cells; HEK 293 human embryonic kidney cells; COS monkey kidney cells; CHO, Chinese hamster ovary cells; R1 mouse embryonic cells; E14.1 mouse embryonic cells; H1 human embryonic cells; H9 human embryonic cells; PER C.6, human embryonic cells; S. cerevisiae yeast cells; or pichia yeast cells. In a particular embodiment, the mammalian system is CHO or HEK293.

Figure 4:
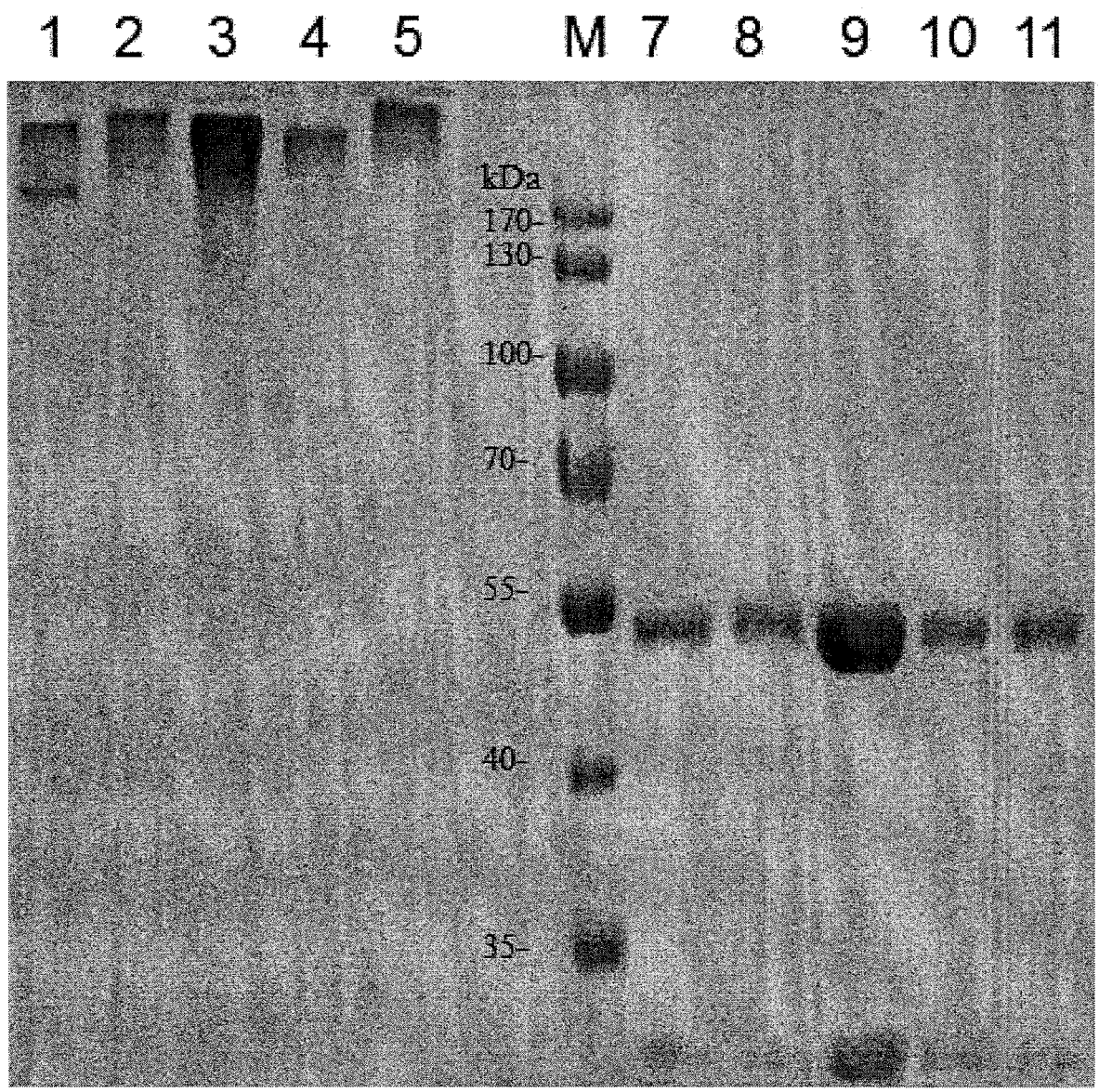
FIG. 4 shows certain purified antibodies on a sodium dodecyl sulfate polyacrylamide gel electrophoresis (SDS-PAGE) gel as single bands under a non-reducing condition (left side) and two bands of heavy and light chains respectively under a reducing condition (right side), demonstrating the purity of the antibodies.
Figure 5A:
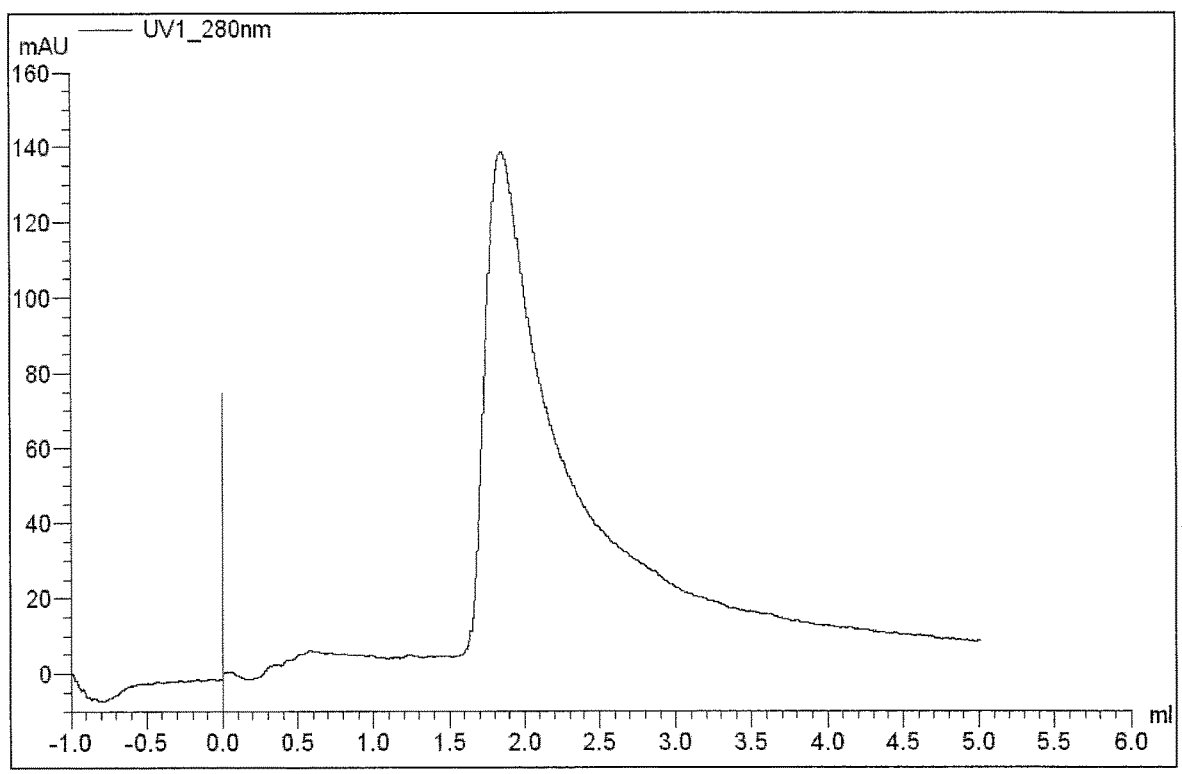
FIGS. 5A-5C show the single peak obtained by size exclusion chromatography (SEC) analyses of the purified antibodies (CPS02 and CPS09) in comparison to the SEC analysis of a control standard human IgG antibody.
Figure 5B:
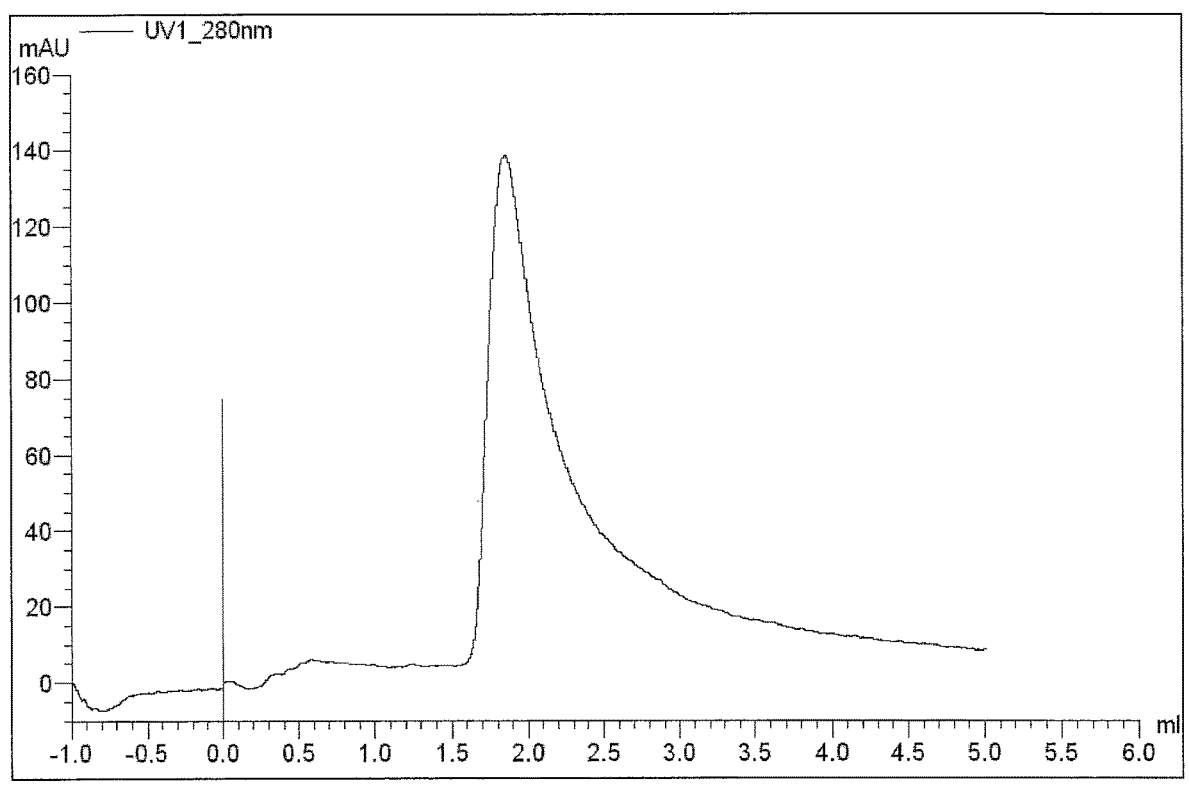
Figure 5C:
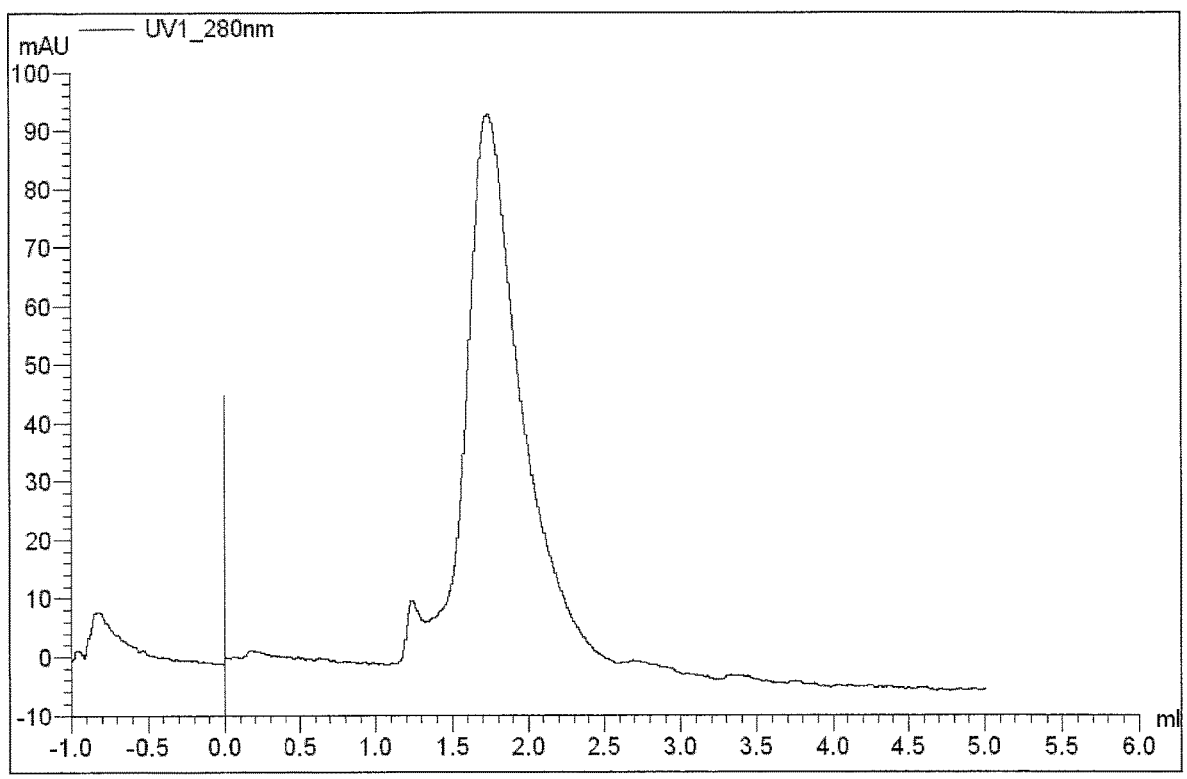

The expressed antibodies were purified from the supernatant of the eukaryotic host cell culture. To verify the purity of the antibodies, the purified mutant antibodies were analyzed using 10% SDS PAGE gel. The antibodies showed a single band under a non-reducing condition (FIG. 4, left half). Under a reducing condition, the antibodies are separated into light chains and heavy chains, which show as two bands in each lane (FIG. 4, right half). The purified antibodies were also analyzed by SEC analysis, which produced a single peak as shown in FIGS. 5A-5C, indicating that the antibodies are obtained at high purity.

The specificity of the 10 antibodies of Table 1 was assayed using both human and mouse IL-22, as well as related antigens (human IL19, human IL20, human IL24, human IL26, INF alpha A, INF-γ, INF-λ1, INF-2 and a non-specific antigen). The 10 mutant antibodies of Table 1 were found to bind to both human and mouse IL-22 with comparable affinity, whereas these mutant antibodies showed very low affinity to the related antigens as can be seen from FIG. 6. This confirms that the 10 mutant antibodies of Table 1 are specific to human and mouse IL-22, due to their low affinity to the other related antigens.

In one embodiment, the antibodies of the present invention have comparable affinities to human and mammalian IL-22 (e.g., mouse IL-22), for example, being within ±20%, ±15%, ±10% or ±5% of each other. In other words, the difference between the two affinities is less than 20%, or less than 15%, of less than 10%, or less than 5% of either affinity.

The affinity of the 10 antibodies of Table 1 was measured by Surface Plasma Resonance (SPR) using a capture assay in PBS buffer to generate binding curves at four different concentrations of each antibody (0.05, 0.1, 0.5, and 1.0 μg/ml). The Ka, Kd and $K_D$ values for the mutant antibodies were calculated from the curves for each of the antibodies.

In one embodiment, the Kd is measured using a BIACORE®-2000 or a BIACORE®-3000 instrument (BIAcore, Inc., Piscataway, N.J.) at 25° C. with antigens immobilized on carboxymethylated dextran biosensor chips (CMS, BIACORE, Inc.). the CMS chips are activated with N-ethyl-N'-(3-dimethylaminopropyl)-carbodiimide hydrochloride (EDC) and N-hydroxysuccinimide (NHS) according to the supplier's instructions. The antigens are diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of the antibody (0.78 nM to 500 nM) are injected in PBS with 0.05% polysorbate 20 (TWEEN-20™) surfactant (PBST) at 25° C. at a flow rate of approximately 25 μl/min.

Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol., vol. 293, pp. 865-881, 1999. If the on-rate exceeds $10^6$ $M^{-1}$ $s^{-1}$ by the surface plasmon resonance assay above, then the on-rate can be determined by using a fluorescence quenching technique that measures the increase or decrease in fluorescence emission intensity (excitation=295 nm; emission=340 nm, 16 nm band-pass) at 25° C. of a 20 nM solution of anti-antibody in PBS with a pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

Some representative antibodies are shown in Table 2. The two antibodies CPS02 and CPS09 have the highest affinity to both human and mouse IL-22. LC-E049K, one of the mutant antibodies in the CPE™ library, is used as a control.

TABLE 2

Affinity of the Antibodies to Human and Mouse IL-22

| clone | human IL-22 | | | mouse IL-22 | | |
|---|---|---|---|---|---|---|
| | ka [M · s] | kd[s$^{-1}$] | $K_D$[M] | ka [M · s] | kd[s$^{-1}$] | $K_D$[M] |
| CPS02 | 1.87E+06 | 4.67E−05 | 2.50E−11 | 1.66E+05 | 5.45E−04 | 3.28E−09 |
| CPS04 | 1.28E+06 | 3.74E−05 | 2.92E−11 | 2.79E+05 | 1.18E−03 | 4.23E−09 |
| CPS09 | 8.60E+05 | 2.18E−05 | 2.53E−11 | 1.94E+05 | 7.68E−04 | 3.96E−09 |
| CPS14 | 1.13E+06 | 3.55E−05 | 3.14E−11 | 2.56E+05 | 1.23E−03 | 4.80E−09 |
| CPS17 | 1.33E+06 | 6.94E−05 | 5.22E−11 | 2.52E+05 | 1.58E−03 | 6.27E−09 |
| LC-E049K | 3.81E+05 | 5.93E−05 | 1.56E−10 | 3.41E+04 | 1.37E−03 | 4.02E−08 |

One of the immediate functions of IL-22 is inducing phosphorylation of Stat3, a protein in the signaling pathway of IL-22. The 10 antibodies of Table 1 were tested in a cell-based assay for blocking IL-22-dependent phosphorylation of Stat3 through human or mouse IL-22 in HepG2 cells. Antibody hum10 and mutant CPE-LC-E049K were used as controls. Four concentrations of each of the antibodies were used: 0.11 μg/mL, 0.33 μg/mL, 1 μg/mL, and 3 μg/mL.

Figure 7A:
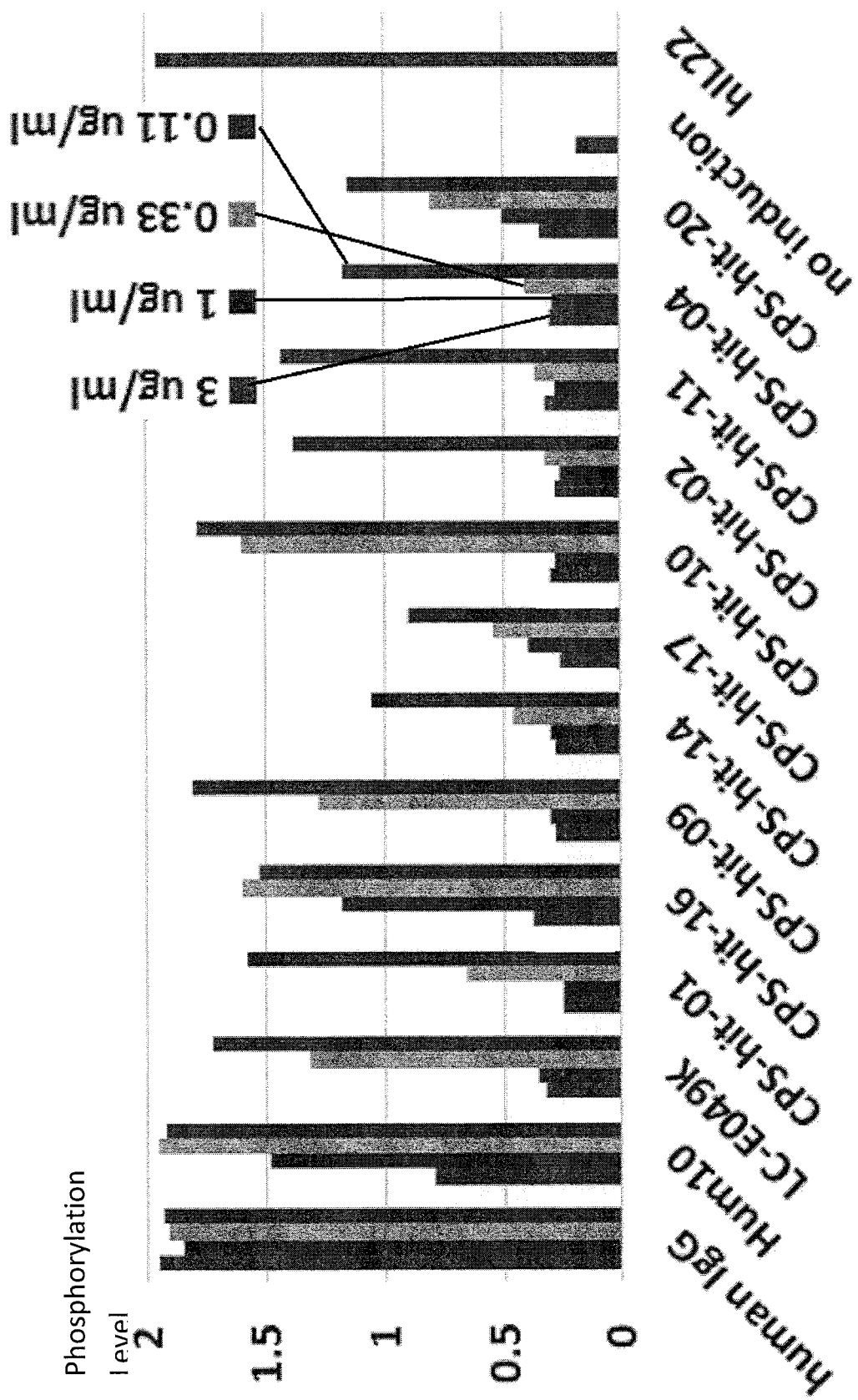
FIG. 7A shows the reduced level phosphorylation of Stat3 protein caused by inhibition of human IL-22 in HepG2 cells using antibodies of the present invention.
Figure 7B:
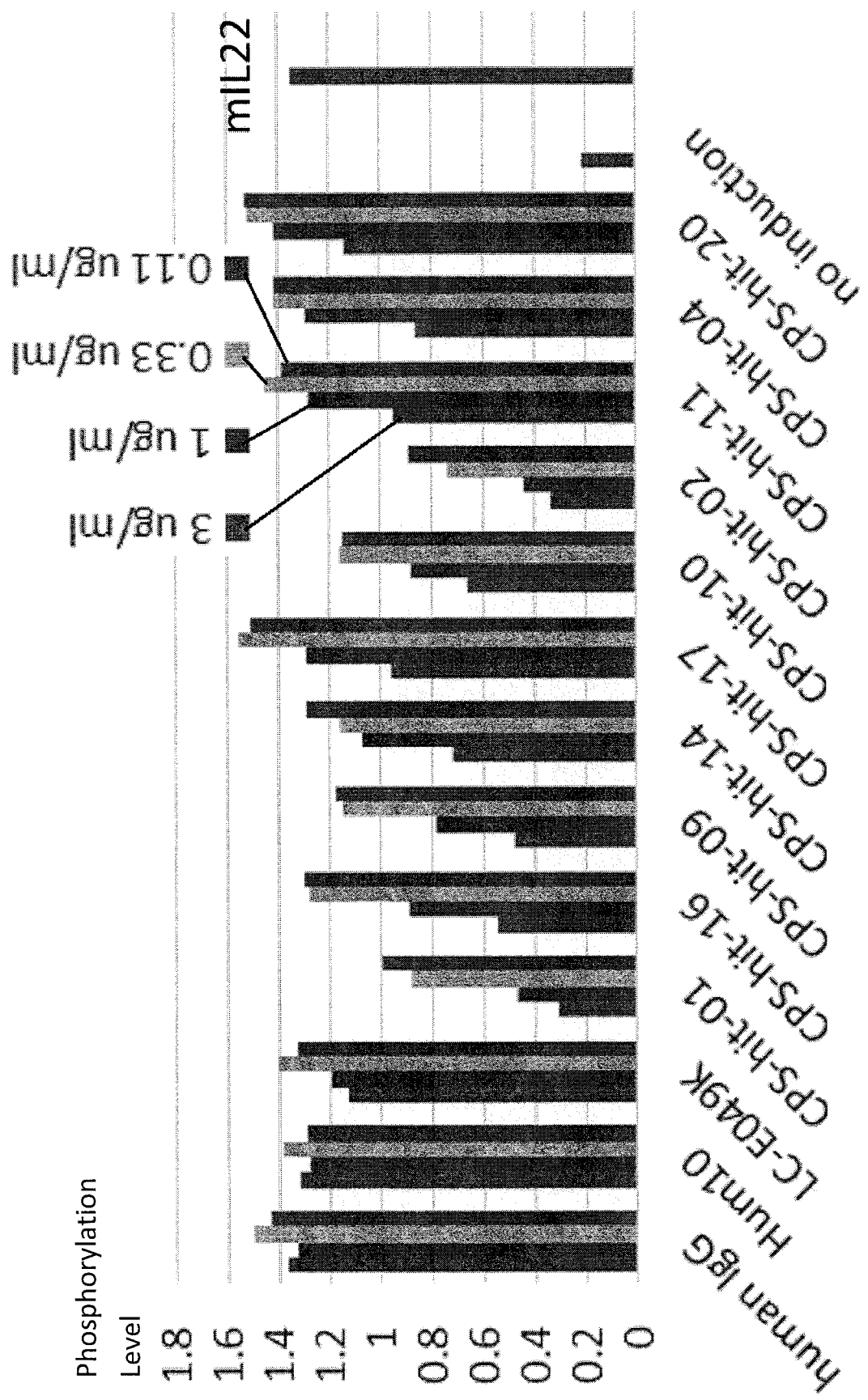
FIG. 7B shows the reduced level phosphorylation of Stat3 protein caused by inhibition of mouse IL-22 in HepG2 cells using antibodies of the present invention.

The inhibition of Stat3 phosphorylation through binding to human IL-22 (hIL-22) is shown in FIG. 7A and the inhibition of Stat3 phosphorylation through binding to mouse IL-22 (mIL-22) is shown in FIG. 7B. The inhibition of Stat3 phosphorylation was found to be dose dependent with higher concentrations of mutant antibodies producing a higher level of inhibition of Stat3 phosphorylation. This indicates that the mutant antibodies of the invention have a causal role in inhibiting IL-22 induced Stat3 phosphorylation in both human and mouse biologic system through binding to human and mouse IL-22.

Figure 8:
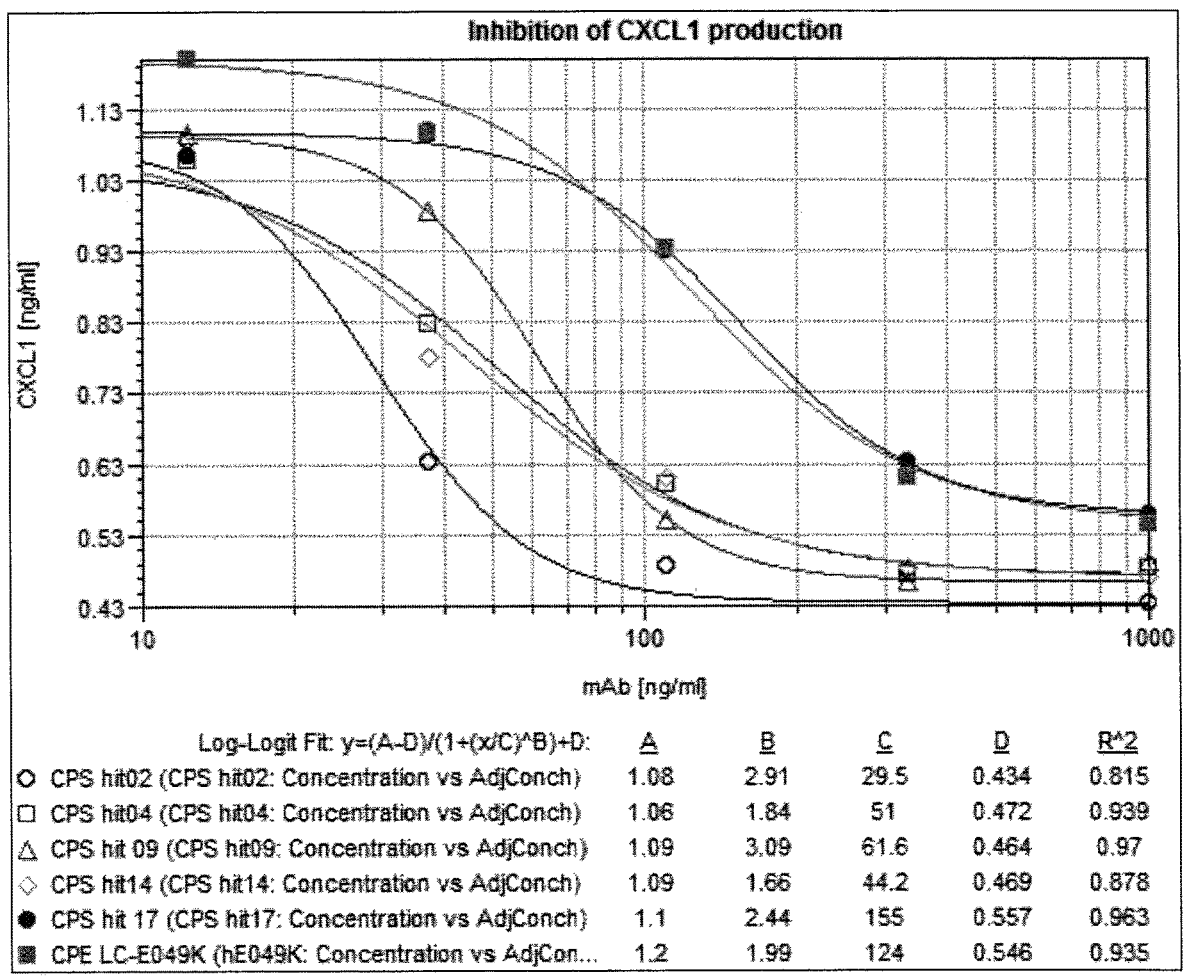
FIG. 8 shows inhibition of CXCL1 protein expression in HT29 cells by antibodies of the present invention.

HT29 cells are a human colorectal adenocarcinoma cell line with epithelial morphology. The cells can express a wide range of cytokines include CXCL10, CXCL11, CCL5, CXCL8, CXCL1, CCL20, and IκB. Cytokine secretion is a sign of immune response and typically causes inflammation in an animal body. The function of anti-IL-22 antibodies in inhibiting IL-22 induced CXCL1 production in HT29 cells is an indicator of the antibodies' ability to suppress immune response and inflammation. The HT29 cells are treated with the anti-IL-22 mutant antibodies at different concentrations and the production of CXCL1 is measured (FIG. 8). The inhibition of CXCL1 production by the mutant antibodies was dose dependent, indicating a causal role of the mutant antibodies in inhibiting IL-22 activities and immune response/inflammation.

The pharmacokinetics of the mutant antibodies of Table 1 were analyzed in mice. The antibodies were injected into mice by IV injection at two doses 0.3 mg/kg and 10 mg/kg. The concentrations of the injected antibodies in the blood plasma were measured by solid phase ELISA. The antibodies were found to have a long half-life in the mice as shown in FIGS. 9A-9B and FIGS. 10A-10B. The half-life for CPS02 in mice was found to be about 18 hours after a 10 mg/kg injection. The half-life for CPS09 was found to be about 16 hours after a 10 mg/kg injection.

Figure 11:
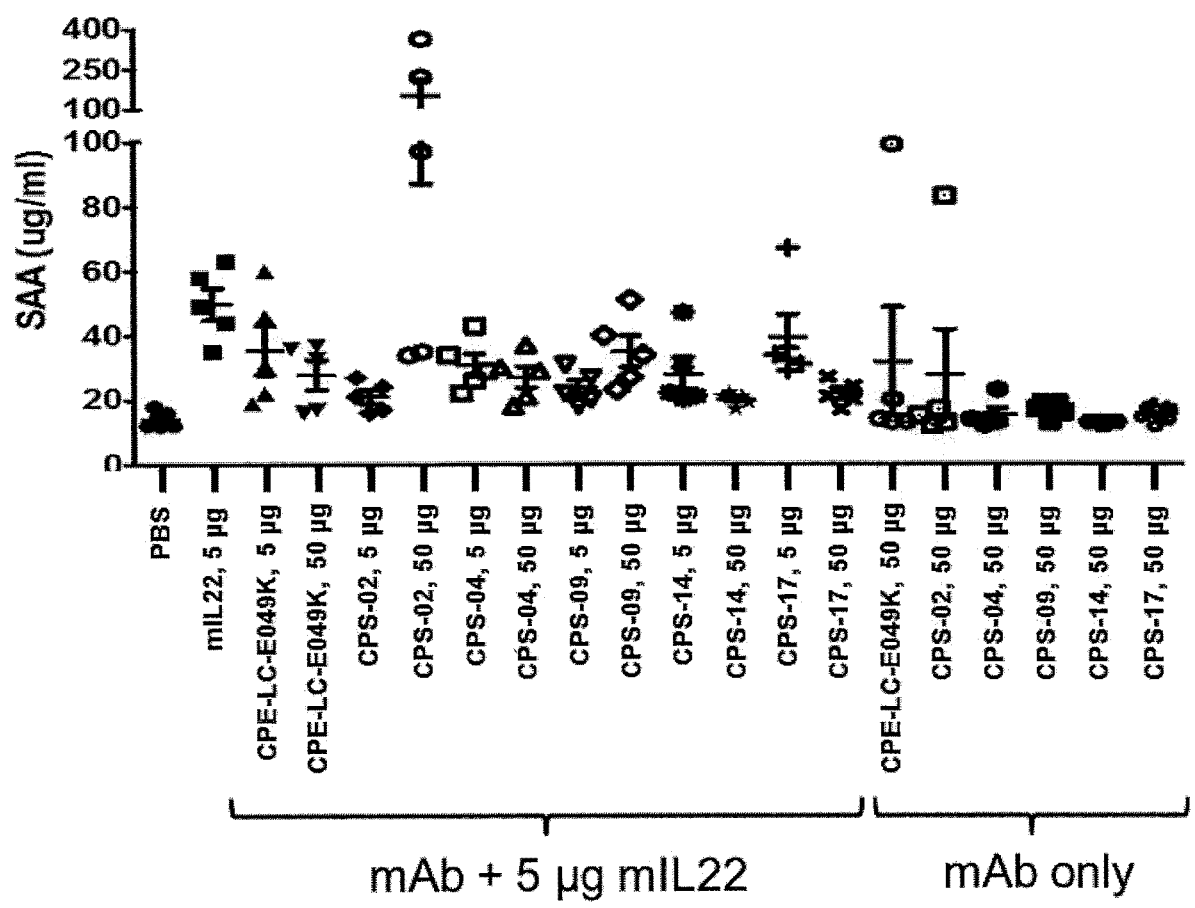
FIG. 11 shows inhibition of IL-22-induced acute phase response in mice by antibodies of the present invention.

IL-22 induces acute phase responses in animals such as mice and humans. The mutant antibodies of the present invention can inhibit the acute phase response induced by IL-22. This acute phase response is indicated by the concentration of serum amyloid (SAA) in the blood of the animal as shown in FIG. 11. The SAA concentrations in the blood of mice were measured 24 hours after treatment of the mice by IL-22 and/or the mutant antibodies. When only IL-22 is used, the SAA concentration was high. With anti-IL-22 antibodies added, the SAA concentrations in the blood of the mice were significantly lower, indicating that the antibodies of the present invention can effectively inhibit the acute phase response in mice.

The properties of the anti-IL-22 antibodies, exemplified by CPS02 and CPS09, are summarized in Table 3.

TABLE 3

| Properties of Anti-IL-22 Antibodies | | | |
|---|---|---|---|
| Properties | hum10 | CPS-hit-02 | CPS-hit-09 |
| Affinity ELISA hIL22 50% max signal mAb (pM] | 2220 | 27 | 81 |
| Affinity ELISA hIL22 50% max signal mAb [pM] | n.d. | 54 | 74 |
| Affinity ELISA mIL22 50% max signal mAb [pM] | no binding | 42 | 141 |
| Affinity ELISA mIL22 50% max signal mAb [pM] | no binding | 19 | 34 |
| STAT3 Phosphorylation; hIL22% inhibition mAb [0.73 nM] | 7.00 | 33.82 | 12.08 |
| STAT3 Phosphorylation; mIL22% inhibition mAb [6.7 nM] | no inhibition | 76.18 | 63.12 |
| CXCL-1 Assay (IC50 [pM]) single data points 02052015 | not tested | 197 | 411 |
| CXCL-1 Assay (IC50 [pM]) double data points 02122015 | not tested | 131 | 204 |
| Productivity (mg/L in transient expression) | n/a | 13 | 57 |
| Aggregate formation at 10 mg/mL in PBS | not tested | no | no |
| Thermostability (% remaining activity 60 min); of duplicate samples | not tested | 104 | 102 |
| Acute Phase response 5 μg mIL22 and 5 μg mAb (% signal reduction) molar ratio mIL22: mAb = 4.5:1 | not tested | 81 | 73 |
| Acute Phase response 5 μg mIL22 and 50 μg mAb (% signal reduction) molar ratio of mIL 22:mAb = 1:2.2 | not tested | signal increase | 42 |
| Acute Phase response 5 μg hIL 22 and 5 ug mAb | | strong increase in repsonse signal | |
| Acute Phase response 5 μg hIL 22 and 50 μg mAb | | | |

The anti-IL-22 antibodies or antibody fragments of the present invention have a high binding affinity for both human and mouse IL-22. Further, the anti-IL-22 antibodies or antibody fragments can cause similar biologic effects in humans and mice, including inhibition of Stat3 phosphorylation and cytokine production (e.g., CXCL1 production), inhibition of acute immune response, and the mutant antibodies were shown to have a reasonably long half-life in mice as well.

The present invention also extends to anti-IL-22 antibodies or antibody fragments including light chain variable regions and heavy chain variable regions from the 10 selected antibodies of Table 1. Particularly, the anti-IL-22 antibodies or antibody fragments of the present invention comprise a light chain variable region selected from light chain variable regions having the amino acid sequences of SEQ ID NOS: 7-12, and a heavy chain variable region selected from heavy chain variable regions having the amino acid sequences of SEQ ID NOS: 13-18.

The present invention also includes anti-IL-22 antibodies or antibody fragments including a light chain variable region having CDRs of the light chain variable regions that have the amino acid sequences of SEQ ID NOS: 7-12, and a heavy chain variable region having CDRs of the heavy chain variable regions that have the amino acid sequences of SEQ ID NOS: 13-18.

Fragments of the antibodies of Table 1, especially these that can bind to both human and mouse IL-22, are also within the scope of the present invention. These antibody fragments may be produced from a full-length antibody via proteolytic digestion (see, e.g., Morimoto et al., *Journal of Biochemical and Biophysical Methods*, vol. 24, pp. 107-117, 1992; and Brennan et al., *Science*, vol. 229, pp. 81, 1985). These antibody fragments can also be produced directly by recombinant host cells. Fab, Fv and scFv antibody fragments can be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')₂ fragments (Carter et al., *Bio/Technology*, vol. 10, pp. 163-167, 1992). According to another approach, F(ab')₂ fragments can be isolated directly from recombinant host cell culture. Fab and F(ab')₂ fragment with increased in vivo half-life comprising salvage receptor binding epitope residues are described in U.S. Pat. No. 5,869,046. Other techniques for the production of antibody fragments will be apparent to the skilled practitioner.

In certain embodiments, an antibody is a single chain Fv fragment (scFv). See WO 93/16185 and U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, Oxford University Press, 1995. The antibody fragment may also be a "linear antibody", e.g., as described in U.S. Pat. No. 5,641,870, for example. Such linear antibodies may be monospecific or bispecific.

In some embodiments, the antibodies of the invention are diabodies. The diabodies may be bivalent or bispecific. See, for example, EP 404,097; WO 1993/01161; Hudson et al., *Nat. Med.*, vol. 9, pp. 129-134, 2003; and Hollinger et al., *Proc. Natl. Acad. Sci. USA*, vol. 90, pp. 6444-6448, 1993 for examples of diabodies. Examples of triabodies and tetrabodies are also described in Hudson et al., *Nat. Med.*, vol. 9, pp. 129-134, 2003.

In some embodiments, the antibodies of the invention are single-domain antibody fragments that comprise all or a portion of the heavy chain variable region or all or a portion of the light chain variable region of an antibody. In certain embodiments, a single-domain antibody is a human single-domain antibody (see, e.g., U.S. Pat. No. 6,248,516).

B. Antibody Variants

In some embodiments, the invention provides variants of the antibodies or antibody fragments as described above. In deriving these variants, a skilled person is guided by the process as described herein. The variants of these antibodies or antibody fragments may be prepared by introducing appropriate modifications into the nucleotide sequence encoding these antibodies or antibody fragments, or by peptide synthesis. Such modifications include, for example, deletions from, and/or insertions into and/or substitutions of residues within the amino acid sequences of the antibody or antibody fragment. Any combination of deletion(s), insertion(s), and substitution(s) can be made to arrive at the variants, provided that the variants possess at least one of the desired characteristics, e.g., binding to both human and mouse IL-22.

1. Sequence Variants

In certain embodiments, the present invention provides antibody or antibody fragment variants having one or more amino acid substitutions, deletions and/or insertions in comparison with the mutant antibodies or antibody fragments described above. Sites of interest for substitutional mutagenesis include the CDRs and framework regions (FRs). Conservative substitutions are shown in Table 4 under the heading of "preferred substitutions." More substantial changes are provided in Table 4 under the heading of "exemplary substitutions," and as further described below in reference to amino acid side chain groups determined by common side-chain properties. Amino acid substitutions may be introduced into an antibody or antibody fragment of interest and the products screened for a desired activity, e.g., binding to both human and mouse IL-22, and/or decreased immunogenicity.

TABLE 4

Amino acid substitutions

| Original Residue | Exemplary Substitutions | Preferred Substitution |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

Non-conservative substitutions will entail exchanging a member of one of these classes for another class.

In making the changes in the amino acid sequences, the hydropathic index of amino acids may be considered. The importance of the hydropathic amino acid index in conferring interactive biologic function on a protein is generally understood in the art. It is accepted that the relative hydropathic character of an amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics. These hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

One type of substitutional variant involves substituting one or more CDR residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., by using phage display-based affinity maturation techniques such as those described herein. For example, one or more CDR residues may be mutated and the variant antibodies displayed on phage and screened for a particular biological activity (e.g. binding affinity).

Sequence modifications (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, *Methods Mol. Biol.*, vol. 207, pp. 179-196, 2008), with the resulting variant $V_H$ or $V_L$ being tested for binding affinity. Affinity maturation by constructing and selecting from libraries has been described, e.g., in Hoogenboom et al. in *Methods in Molecular Biology*, vol. 178, pp. 1-37, 2001). In some embodiments of affinity maturation, diversity is introduced into the variable genes chosen for maturation by any of a variety of methods (e.g., error-prone PCR, chain shuffling, or oligonucleotide-directed mutagenesis). A library with the variants is then created. The library is then screened to identify antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. LC-CDR3 and HC-CDR3, in particular, are often targeted.

In certain embodiments, substitutions, insertions, or deletions may be made within one or more CDRs so long as such alterations do not substantially reduce the ability of the antibody or antibody fragment to bind IL-22. For example, conservative alterations (e.g., conservative substitutions as provided herein) that do not substantially reduce binding affinity may be made in CDRs. Such alterations may be outside of CDR "hotspots". In certain embodiments of the variant $V_H$ and $V_L$ regions, each CDR is unaltered, or contains no more than one, two or three amino acid substitutions.

In some embodiments, the modifications are introduced into the non-CDR regions of the antibodies. In other words, the complementarity determining regions (CDRs) of the light chain variable regions having amino acid sequences of SEQ ID NOS: 7-12 and the heavy chain variable regions having amino acid sequences of SEQ ID NOS: 13-18 remain intact. The modifications may instead be introduced into FRs or constant regions.

A useful method for identification of amino acid residues or regions of an antibody that may be targeted for mutagenesis is "alanine scanning mutagenesis" as described by Cunningham and Wells, *Science*, vol. 244, pp. 1081-1085, 1989. In this method, a residue or group of target residues (e.g., charged residues such as arg, asp, his, lys, and glu) is identified and replaced by a neutral or negatively charged amino acid (e.g., alanine or polyalanine) to determine whether the interaction of the antibody or antibody fragment with antigen is affected. Further substitutions may be introduced at the amino acid locations demonstrating functional sensitivity to the initial substitutions. Alternatively, or additionally, a crystal structure of an antigen-antibody complex may be used to identify contact points between the antibody or antibody fragment and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to a region containing a dozen residues, as well as intrasequence insertions of single or multiple amino acid residues. Examples of terminal insertions include an antibody with an N-terminal methionyl residue. Other insertion variants of the antibody include the fusion at the N- or C-terminus of the antibody to an enzyme (e.g. for ADEPT) or a polypeptide which increases the serum half-life of the antibody.

Amino acid sequence modification(s) of the antibodies described herein may improve the binding affinity and/or other biological properties of the antibody.

A further aspect of the present invention encompasses function-conservative variants of the antibodies or antibody fragments. Function-conservative variants are those in which a given amino acid residue in an antibody has been changed without altering the overall conformation and function of the antibody, including, but not limited to, replacement of an amino acid with an amino acid having similar properties such as, for example, polarity, hydrogen bonding potential, acidic, basic, hydrophobic, aromatic, and the like. Amino acids other than those indicated as conserved may differ in a protein so that the percent protein or amino acid sequence similarity between any two proteins of similar function may vary and may be, for example, from 70% to 99% as determined according to an alignment scheme such as the Cluster Method, wherein similarity is based on the MEGALIGN algorithm. A "function-conservative variant" also includes an antibody which has at least 60% amino acid identity as determined by BLAST or FASTA algorithms, or at least 75%, or at least 85%, or at least 90%, or at least 91%, or at least 92%, or at least 93%, or at least 94%, or at least 95%, or at least 96%, or at least 97%, or least 98% or at least 99% identity to the parent antibody or antibody fragment, and which has the same or substantially similar properties or functions as the antibodies or antibody fragments identified by the present invention, in particular a good binding affinity for both human and mouse IL-22.

2. Humanized Antibodies or Antibody Fragments

In some embodiments, the invention provides humanized antibodies. Typically, a non-human antibody is humanized to reduce immunogenicity to humans, while retaining the specificity and affinity of the parent non-human antibody. Generally, a humanized antibody comprises one or more variable regions in which CDRs (or portions thereof) are derived from a non-human antibody, and FRs (or portions thereof) are derived from a human antibody. A humanized antibody may optionally also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Various methods for humanizing non-human antibodies are known in the art. For example, a humanized antibody can have one or more amino acid residues introduced from a source which is non-human. These non-human amino acid residues are often referred to as "import" residues, which are typically taken from an "import" variable region. Humanization can be essentially performed following the method of Winter and co-workers (Jones et al. (1986) *Nature*, vol. 321, pp. 522-525; Riechmann et al. (1988) *Nature*, vol. 332, pp. 323-327; Verhoeyen et al. (1988) *Science*, vol. 239, pp. 1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable region has been substituted by the corresponding sequence from a non-human species. In practice, humanized antibodies are typically human antibodies in which some CDR residues and possibly some FR residues are substituted by residues from analogous sites in rodent antibodies.

The choice of human variable regions, both light and heavy, to be used in making the humanized antibodies can be important to reduce antigenicity. According to the so-called "best-fit" method, the sequence of the variable region of a rodent antibody is screened against the entire library of known human variable-domain sequences. The human sequence which is closest to that of the rodent is then accepted as the human framework for the humanized antibody (Sims et al. (1993) *J. Immunol.*, vol. 151, pp. 2296; Chothia et al. (1987) *J. Mol. Biol.*, vol. 196, p. 901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA*, vol. 89, p. 4285; Presta et al. (1993) *J. Immunol.*, vol. 151, p. 2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding Humanized antibodies and methods of making them are reviewed, e.g., in Almagro and Fransson, *Front. Biosci.*, vol. 13, pp. 1619-1633, 2008, and are further described, e.g., in Riechmann et al., *Nature*, vol. 332, pp. 323-329, 1988; Queen et al., *Proc. Nat'l Acad. Sci. USA*, vol. 86, pp. 10029-10033, 1989; U.S. Pat. Nos. 5,821,337, 7,527,791, 6,982,321, and 7,087,409; Kashmiri et al., *Methods*, vol. 36, pp. 25-34, 2005 (describing SDR (a-CDR) grafting); Padlan, *Mol. Immunol.*, vol. 28, pp. 489-498, 1991 (describing "resurfacing"); Dall'Acqua et al., *Methods*, vol. 36, pp. 43-60, 2005 (describing "FR shuffling"); and Osbourn et al., *Methods*, vol. 36, pp. 61-68, 2005 and Klimka et al., *Br. J. Cancer*, vol. 83, pp. 252-260, 2000 (describing the "guided selection" approach to FR shuffling).

Human framework regions that may be used for humanization include but are not limited to: framework regions selected using the "best-fit" method (see, e.g., Sims et al. *J. Immunol.*, vol. 151, p. 2296, 1993); framework regions derived from the consensus sequence of human antibodies of a particular subgroup of light or heavy chain variable regions (see, e.g., Carter et al. *Proc. Natl. Acad. Sci. USA*, vol. 89, p. 4285, 1992; and Presta et al. *J. Immunol.*, vol. 151, p. 2623, 1993); human mature (somatically mutated) framework regions or human germline framework regions (see, e.g., Almagro and Fransson, *Front. Biosci.*, vol. 13, pp. 1619-1633, 2008); and framework regions derived from screening FR libraries (see, e.g., Baca et al., *J. Biol. Chem.*, vol. 272, pp. 10678-10684, 1997 and Rosok et al., *J. Biol. Chem.*, vol. 271, pp. 22611-22618, 1996).

It is known that when a humanized antibody is produced by simply grafting only CDRs in $V_H$ and $V_L$ of an antibody derived from a non-human animal in FRs of the $V_H$ and $V_L$ of a human antibody, the antigen binding affinity is reduced in comparison with that of the original antibody derived from a non-human animal. It is considered that several amino acid residues of the $V_H$ and $V_L$ of the non-human antibody, not only in CDRs but also in FRs, are directly or indirectly associated with the antigen binding affinity. Hence, substitution of these amino acid residues with different amino acid residues derived from FRs of the $V_H$ and $V_L$ of the human antibody may reduce the binding affinity. In order to resolve the problem, in antibodies grafted with human FRs, attempts have to be made to identify, among amino acid sequences of the FR of the $V_H$ and $V_L$ of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding affinity could be improved by replacing the identified amino acids with amino acid residues of the original antibody derived from a non-human animal.

3. Glycosylation Variants

In certain embodiments, an antibody or fragment thereof provided herein is altered to increase or decrease the extent to which the antibody is modified by adding one or more oligosaccharides, thus becoming a glycosylated antibody. The modification is accomplished by adding the oligosaccharides at one or more glycosylation sites. Addition or deletion of glycosylation sites to the antibody or fragment may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH*, vol. 15, pp. 26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.*, vol. 336, pp. 1239-1249, 2004; Yamane-Ohnuki et al. *Biotech. Bioeng.*, vol. 87, pp. 614-622, 2004. Examples of cell lines capable of producing defucosylated antibodies include Lec13 CHO cells deficient in protein fucosylation (Ripka et al. *Arch. Biochem. Biophys.*, vol. 249, pp. 533-545, 1986; US Pat Appl No US 2003/0157108 A; and WO 2004/056312 A1, especially at Example 11), and knockout cell lines, such as alpha-1,6-fucosyltransferase gene, FUT8, knockout CHO cells (see, e.g., Yamane-Ohnuki et al. *Biotech. Bioeng.*, vol. 87, pp. 614-622, 2004; Kanda, Y. et al., *Biotechnol. Bioeng.*, vol. 94, pp. 680-688, 2006; and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

4. Fe Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention provides an antibody variant with an Fc region variant that possesses some but not all effector functions, which make it a desirable candidate for applications in which the half life of the antibody in vivo is important and certain effector functions (such as ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 5 on page 464 of Ravetch and Kinet, *Annu. Rev. Immunol.*, vol. 9, pp. 457-492, 1991. Non-limiting examples of in vitro assays to assess ADCC activity of a molecule of interest are described in U.S. Pat. No. 5,500,362 (see also, e.g. Hellstrom et al. *Proc. Nat'l Acad. Sci. USA*, vol. 83, pp. 7059-7063, 1986) and Hellstrom, I et al., *Proc. Nat'l Acad. Sci. USA*, vol. 82, pp. 1499-1502, 1985; U.S. Pat. No. 5,821,337 (see also Bruggemann et al., *J. Exp. Med.*, vol. 166, pp. 1351-1361, 1987). Alternatively, non-radioactive assay methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l. Acad. Sci. USA*, vol. 95, pp. 652-656, 1998. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods*, vol. 202, pp. 163-171, 1996; Cragg, M. S. et al., *Blood*, vol. 101, pp. 1045-1052, 2003; and Cragg, M. S, and M. J. Glennie, *Blood*, vol. 103, pp. 2738-2743, 2004). FcRn binding and in vivo clearance/half life determinations can also be performed using methods known in the art (see, e.g., Petkova, S. B. et al., *Int'l. Immunol.*, vol. 18, pp. 1759-1769, 2006).

Antibodies with reduced effector function include those with substitution of one or more Fc region residues 238, 265, 269, 270, 297, 327 and 329 (U.S. Pat. No. 6,737,056). Such Fc mutants include substitutions at two or more of amino acid positions 265, 269, 270, 297 and 327, including the so-called "DANA" Fc mutant with substitutions of residues 265 and 297 with alanine (U.S. Pat. No. 7,332,581).

In certain embodiments, the antibody has an Fc variant with improved or diminished binding to FcRs. (See, e.g., U.S. Pat. No. 6,737,056; WO 2004/056312, and Shields et al., *J. Biol. Chem.*, vol. 9, pp. 6591-6604, 2001).

In certain embodiments, the antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.*, vol. 164, pp. 4178-4184, 2000.

Antibodies with increased half lives and improved binding to the neonatal Fc receptor (FcRn), which is responsible for the transfer of maternal IgGs to the fetus (Guyer et al., *J. Immunol.*, vol. 117, pp. 587-593, 1976 and Kim et al., *J. Immunol.*, vol. 24, p. 249, 1994), are described in US2005/0014934. Those antibodies comprise an Fc region with one or more substitutions therein which improve binding of the Fc region to FcRn. Such Fc variants include/e those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature*, vol. 322, pp. 738-740, 1988; U.S. Pat. Nos. 5,648,260; 5,624,821; and WO 94/29351 for other examples of Fc region variants.

5. Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Cysteine engineered antibodies may be generated as described, e.g., in U.S. Pat. No. 7,521,541.

6. Antibody Derivatives

In certain embodiments, an antibody or antibody fragment provided herein may be modified antibody or antibody fragment that contains additional nonproteinaceous moieties that are known in the art and readily available. The moieties suitable for derivatization of the antibody or antibody fragment include, but are not limited to, water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. The number of polymers attached to the antibody or antibody fragment may vary, and if more than one polymer is attached, they can be the same or different molecules. In general, the number and/or type of polymers used for antibody derivatization can be determined based on considerations including, but not limited to, the particular properties or functions of the antibody or antibody fragment to be improved, whether the derivative will be used in a therapy under defined conditions, etc.

In one embodiment, the antibody or antibody fragment and nonproteinaceous moiety may be linked using selective heating by exposure to radiation. In one embodiment, the nonproteinaceous moiety is a carbon nanotube (Kam et al., *Proc. Natl. Acad. Sci. USA*, vol. 102, pp. 11600-11605, 2005). The radiation may be of any wavelength, and includes, but is not limited to, wavelengths that do not harm ordinary cells, but which heat the nonproteinaceous moiety to a temperature at which cells proximate to the antibody-nonproteinaceous moiety are killed.

The anti-IL-22 antibodies of the invention may be chimeric antibodies. Certain chimeric antibodies are described, e.g., in U.S. Pat. No. 4,816,567; and Morrison et al., *Proc. Natl. Acad. Sci. USA*, vol. 81, pp. 6851-6855, 1984. In one example, the chimeric antibody comprises a non-human variable region (e.g., a variable region derived from a mouse, rat, hamster, rabbit, or non-human primate, such as a monkey) and a human constant region. In a further example, the chimeric antibody is a "class switched" antibody in which the class or subclass of the antibody has been changed relative to the class or subclass of the parent antibody. Chimeric antibodies include antigen-binding fragments thereof.

In some embodiments, the anti-IL-22 antibodies of the invention are multi-specific, e.g. bispecific antibodies. Multi-specific antibodies are monoclonal antibodies that have binding specificities for at least two different sites. In certain embodiments, one of the binding specificities is for IL-22 and the other is for another antigen. In certain embodiments, bispecific antibodies may bind to two different epitopes of IL-22. Bispecific antibodies may also be used to localize cytotoxic agents to cells which express IL-22. Bispecific antibodies can be prepared as full length antibodies or antibody fragments.

Techniques for making multi-specific antibodies include, but are not limited to, recombinant co-expression of two immunoglobulin heavy chain-light chain pairs having different specificities (see Milstein and Cuello, *Nature*, vol. 305, pp. 537-540, 1983), WO 93/08829, and Traunecker et al., *EMBO J.* vol. 10, pp. 3655-3659, 1991), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, vol. 229, pp. 81-83, 1985); using leucine zippers to produce bi-specific antibodies (see, e.g., Kostelny et al., *J. Immunol.*, vol. 148, pp. 1547-1553, 1992); using "diabody" technology for making bispecific antibody fragments (see, e.g., Hollinger et al., *Proc. Natl. Acad. Sci. USA*, vol. 90, pp. 6444-6448, 1993); and using single-chain Fv (scFv) dimers (see, e.g. Gruber et al., *J. Immunol.*, vol. 152, pp. 5368-5374, 1994); and preparing trispecific antibodies as described, e.g., in Tutt et al. *J. Immunol.*, vol. 147, pp. 60-69, 1991.

Engineered antibodies with three or more functional antigen binding sites, including "Octopus antibodies," are also included herein (see, e.g. US 2006/0025576A1).

The antibody or antibody fragment may also include a "Dual Acting Fab" or "DAF" comprising an antigen binding site that binds to IL-22 as well as another, different antigen (see, US 2008/0069820, for example).

C. Immunoconjugates

In another aspect, the invention also provides immunoconjugates including an anti-IL-22 antibody or antibody fragment described herein that is modified by conjugation to one or more therapeutic agents, prophylactic agents, diagnostic agents, detectable labels, chelators and contrast agents. In one embodiment, the immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.*, vol. 53, pp. 3336-3342, 1993; and Lode et al., *Cancer Res.*, vol. 58, pp. 2925-2928, 1998); an anthracycline such as daunomycin or doxorubicin (see Kratz et al., *Current Med. Chem.*, vol. 13, pp. 477-523, 2006; Jeffrey et al., *Bioorganic & Med. Chem. Letters*, vol. 16, pp. 358-362, 2006; Torgov et al., *Bioconj. Chem.*, vol. 16, pp. 717-721, 2005; Nagy et al., *Proc. Natl. Acad. Sci. USA*, vol. 97, pp. 829-834, 2000; Dubowchik et al., *Bioorg. & Med. Chem. Letters*, vol. 12, vol. 1529-1532, 2002; King et al., *J. Med. Chem.*, vol. 45, pp. 4336-4343, 2002; and U.S. Pat. No. 6,630,579); methotrexate; vindesine; a taxane such as docetaxel, paclitaxel, larotaxel, tesetaxel, and ortataxel; a trichothecene; and CC1065.

In one embodiment, the conjugated agent is a therapeutic agent selected from cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In another embodiment, the conjugated agent is an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, the conjugate comprises a radioactive atom including $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may also comprise a radioactive atom for scintigraphic studies, for example tc99m or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or Immunoconjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, vol. 238, p. 1098, 1987. Carbon-14-labeled 1-isothiocyanatobenzyl-3-methyldiethylene triaminepentaacetic acid (MX-DTPA) is an exemplary chelating agent or chelator for conjugation of radionucleotide to the antibody. See WO 1994/011026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.*, vol. 52, pp. 127-131, 1992; U.S. Pat. No. 5,208,020) may be used.

The immunoconjugates may be prepared with cross-linker reagents including, but not limited to, BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

An exemplary embodiment of an ADC comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine. The ADC may have the formula Ab-(L-D)$_p$, where p is 1 to about 20.

In some embodiments, the number of drug moieties that can be conjugated to an antibody is limited by the number of free cysteine residues. In some embodiments, free cysteine residues are introduced into the antibody amino acid sequence by the methods described herein. Exemplary ADCs include, but are not limited to, antibodies that have 1, 2, 3, or 4 engineered cysteine amino acids (Lyon et al., *Methods in Enzym.*, vol. 502, pp. 123-138, 2012). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

Linkers are used to conjugate a moiety to the antibody to form an immunoconjugate such as an ADC. Suitable linkers are described in WO 2017/180842.

Some drug moieties that may be conjugated to the antibodies are described in WO 2017/180842.

Drug moieties also include compounds with nucleolytic activity (e.g., a ribonuclease or a DNA endonuclease).

In certain embodiments, the immunoconjugate may comprise a spin label for nuclear magnetic resonance (NMR) imaging, such as zirconium-89, iodine-123, iodine-131, indium-111, fluorine-19, carbon-13, nitrogen-15, oxygen-17, gadolinium, manganese or iron. Zirconium-89 may be complexed to various metal chelators and conjugated to antibodies, e.g., for PET imaging (WO 2011/056983).

The radioactive or other labels may be incorporated in the immunoconjugate in known ways. For example, the antibody or fragment may be biosynthesized or chemically synthesized using suitable amino acid precursors including, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al., *Biochem. Biophys. Res. Commun.*, vol. 80, pp. 49-57, 1978) can be used to incorporate iodine-123. *"Monoclonal Antibodies in Immunoscintigraphy"* (Chatal, CRC Press 1989) describes certain other methods.

In certain embodiments, the immunoconjugate may comprise an antibody conjugated to a prodrug-activating enzyme. The prodrug-activating enzyme can convert a prodrug (e.g., a peptidyl chemotherapeutic agent, see WO 81/01145) to an active drug, such as an anti-cancer drug. Such immunoconjugates are useful in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as *serratia* protease, thermolysis, subtilisin, carboxypeptidases and cathepsins (such as cathepsins B and L), which are useful for converting peptide-containing prodrugs into free drugs;

D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature*, vol. 312, pp. 604-608, 1984.

D. Pharmaceutical Compositions

In some embodiments, the invention provides pharmaceutical compositions including the anti-IL-22 antibodies, antibody fragments, variants, derivatives or immunoconjugates thereof. The anti-IL-22 antibodies or antibody fragments have anti-inflammatory activity. Further, it is known that IL-22 is involved in cancer initiation or progression. Thus, the anti-IL-22 antibodies, antibody fragments, variants, derivatives or immunoconjugates thereof may be used in pharmaceutical compositions for treating immune-related diseases or proliferative diseases associated with IL-22 expression. The antibodies, fragments, variants, derivatives or immunoconjugates may be used in the pharmaceutical compositions as the sole active agent or in combination with any suitable agent or other conventional treatments.

The antibodies or antibody fragments may be formulated in the pharmaceutical composition to deliver about 0.0001 to 10.0 milligrams, or about 0.001 to 5 milligrams, or about 0.001 to 1 milligrams, or about 0.001 to 0.1 milligrams, or about 0.1 to 1.0 or even about 10 milligrams of an antibody or antibody fragment per dose. Multiple doses can be administered at selected time intervals.

For the treatment or reduction in the severity of an immune disease, the appropriate dosage of a composition of the invention will depend on the type of disease to be treated, the severity and course of the disease, whether the composition is administered for preventive or therapeutic purposes, previous therapy, the patient's clinical history and response to the compound, and the discretion of the attending physician.

For example, depending on the type and severity of a disease, about 1 µg/kg to about 15 mg/kg (e.g., 0.1-20 mg/kg) of the antibody or antibody fragment is an initial candidate dosage for administration to a patient, whether, for example, by one or more separate administrations, or by continuous infusion. A typical daily dosage might range from about 1 µg/kg to about 100 mg/kg or more antibody or antibody fragment, depending on the factors mentioned above. For repeated administrations over several days or longer, depending on the condition, the treatment may be sustained until a desired suppression of disease symptoms occurs. The progress of this therapy can be monitored by conventional techniques and assays.

The pharmaceutical compositions including anti-IL-22 antibody, antibody fragment or immunoconjugate can be formulated according to known methods for preparing pharmaceutical compositions by mixing the antibody or antibody fragment having the desired degree of purity with one or more optional pharmaceutically acceptable carriers (*Remington's Pharmaceutical Sciences,* 16th edition, Osol, A. Ed. (1980)), in the form of lyophilized formulations or aqueous solutions.

Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelators such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

The pharmaceutically acceptable carriers can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may include isotonic agents, for example, sugars or sodium chloride. Prolonged absorption of the injectable compositions can be brought about by the use in the compositions of agents delaying absorption, for example, aluminium monostearate and gelatin.

In some embodiments, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition of, for example, sterilized water or physiological saline, permit the constitution of injectable solutions.

In some embodiments, pharmaceutically acceptable tonicity agents, sometimes known as "stabilizers" are present to adjust or maintain the tonicity of a liquid in the pharmaceutical composition. When used with large, charged biomolecules such as proteins and antibodies, they are often termed "stabilizers" because they can interact with the charged groups of the amino acid side chains, thereby lessening the potential for inter- and intra-molecular interactions. Tonicity agents can be present in any amount of from 0.1% to 25% by weight, or 1 to 5% of the pharmaceutical composition. Exemplary tonicity agents include polyhydric sugar alcohols, for example trihydric or higher sugar alcohols, such as glycerin, erythritol, arabitol, xylitol, sorbitol and mannitol.

Additional pharmaceutically acceptable excipients may be included in the pharmaceutical composition, such as one or more of the following: (1) bulking agents, (2) solubility enhancers, (3) stabilizers, and (4) agents preventing denaturation or adherence to the container wall. The excipients may include polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

The pharmaceutical compositions may include pharmaceutically acceptable non-ionic surfactants or detergents (also known as "wetting agents") to help solubilize the antibodies or antibody fragments as well as to protect the antibodies or antibody fragments against agitation-induced aggregation, which also permits the compositions to be exposed to shear surface stress without causing denaturation of the antibodies or antibody fragments. Non-ionic surfactants may be present in a concentration range of about 0.05 mg/ml to about 1.0 mg/ml, or about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

The antibody or antibody fragment can be formulated into a pharmaceutic composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

In some embodiments, the pharmaceutical compositions comprise a combination of at least one anti-IL-22 antibody or antibody fragment and at least one other therapeutic agent or prophylactic agent to be administered in a combination therapy. The other therapeutic agent or prophylactic agent may be a cytokine inhibitor, growth factor inhibitor, immunosuppressant, anti-inflammatory agent, metabolic inhibitor, enzyme inhibitor, cytotoxic agent, and cytostatic agent, as described in more detail below. In one embodiment, the another therapeutic agent is a standard treatment for arthritis, including, but not limited to, non-steroidal anti-inflammatory agents (NSAIDs); corticosteroids, including prednisolone, prednisone, cortisone, and triamcinolone; and disease modifying anti-rheumatic drugs (DMARDs), such as methotrexate, hydroxychloroquine (Plaquenil) and sulfasalazine, leflunomide (Arava), tumor necrosis factor inhibitors, including etanercept (Enbrel), infliximab (Remicade) (with or without methotrexate), and adalimumab (Humira), anti-CD20 antibody (e.g., Rituxan), soluble interleukin-1 receptor, such as anakinra (Kineret), gold, minocycline (Minocin), penicillamine, and cytotoxic agents, including azathioprine, cyclophosphamide, and cyclosporine. Such combination therapies may advantageously utilize lower dosages of the administered therapeutic agents, thus avoiding possible toxicities or complications associated with the various monotherapies. Moreover, the other therapeutic agent disclosed herein may act on pathways in addition to or that differ from the IL-22/IL-22R/IL-10R2 pathway, and thus are expected to enhance and/or synergize with the effects of the anti-IL-22 antibodies.

In some embodiments, the other therapeutic agents or prophylactic agents used in combination with anti-IL-22 antibodies or fragments may be those therapeutic agents that interfere at different stages in the autoimmune and subsequent inflammatory response. In one embodiment, at least one anti-IL-22 antibody described herein may be co-formulated with, and/or co-administered with, at least one cytokine and/or growth factor antagonist. The antagonists may include soluble receptors, peptide inhibitors, small molecules, ligand fusions, antibodies and binding fragments thereof (that bind cytokines or growth factors or their receptors or other cell surface molecules), and "anti-inflammatory cytokines" and agonists thereof.

Non-limiting examples of these therapeutic agents or prophylactic agents include, but are not limited to, antagonists of at least one interleukin (e.g., IL-1, IL-2, IL-6, IL-7, IL-8, IL-12 (or one of its subunits p35 or p40), IL-13, IL-15, IL-16, IL-17A-F (including heterodimers thereof, for example, IL-17A/IL-17F heterodimer), IL-18, IL-19, IL-20, IL-21, and IL-23 (or one of its subunits p19 or p40)); cytokine (e.g., TNFα, LT, EMAP-II, and GM-CSF); and growth factor (e.g., FGF and PDGF). The therapeutic agents may also include, but not limited to, antagonists of at least one receptor for an interleukin, cytokine, and growth factor. Anti-IL-22 antibodies can also be combined with inhibitors (e.g., antibodies or binding fragments thereof) to cell surface molecules such as CD2, CD3, CD4, CD8, CD20 (e.g. Rittman), CD25, CD28, CD30, CD40, CD45, CD69, CD80 (B7.1), CD86 (B7.2), CD90, or their ligands (e.g., CD154 (gp39, CD40L)), or LFA-1/ICAM-1 and VLA-4NCAM-1 (Yusuf-Makagiansar et al. (2002) Med Res Rev 22(2):146-67)). In certain embodiments, antagonists that can be used in combination with anti-IL-22 antibodies described herein may include antagonists of IL-1, IL-12 (or one of its subunits p35 or p40), TNFα, IL-15, IL-17A-F (including heterodimers thereof, for example, IL-17A/IL-17F heterodimer), IL-18, IL-19, IL-20, IL-21, and IL-23 (or one of its subunits p19 or p40), and their receptors.

In one embodiment, the other therapeutic agent or prophylactic agent is selected from IL-12 antagonists (such as antibodies that bind IL-12 (see e.g., WO 00/56772) or one of its subunits p35 or p40); IL-12 receptor inhibitors (such as antibodies to the IL-12 receptor); and soluble IL-12 receptor and fragments thereof. In one embodiment, the other therapeutic agent is selected from IL-15 antagonists such as antibodies against IL-15 or its receptor, soluble fragments of the IL-15 receptor, and IL-15-binding proteins. In one embodiment, the other therapeutic agent is selected from IL-12 antagonists such as antibodies to IL-18, soluble fragments of the IL-18 receptor, and IL-18 binding proteins (IL-18BP, Mallet et al. (2001) Circ. Res. 28). In one embodiment, the other therapeutic agent is selected from IL-1 antagonists such as Interleukin-1-Converting Enzyme (ICE)

inhibitors (such as Vx740), IL-1 antagonists (e.g., IL-1RA (ANIKINRA, AMGEN)), sIL-1RII (Immunex), and anti-IL-1 receptor antibodies.

In one embodiment, the other therapeutic agent or prophylactic agent is selected from TNF antagonists including antibodies to TNF (e.g., human TNFα), such as D2E7 (human anti-TNFα antibody, U.S. Pat. No. 6,258,562, Humira™, BASF); CDP-571/CDP-870/BAY-10-3356 (humanized anti-TNFα antibodies, Celltech/Pharmacia); cA2 (chimeric anti-TNFα antibody, Remicade™, Centocor); and anti-TNF antibody fragments (e.g., CPD870). Other examples include soluble TNF receptor (e.g., human p55 or p75) fragments and derivatives, such as p55 kdTNFR-IgG (55 kD TNF receptor-IgG fusion protein, Lenercept™) and 75 kdTNFR-IgG (75 kD TNF receptor-IgG fusion protein, Enbrel™ Immunex, see, e.g., Arthritis & Rheumatism (1994) Vol. 37, 5295; J. Invest. Med. (1996) Vol. 44, 235A). Further examples include enzyme antagonists (e.g., TNFα converting enzyme inhibitors (TACE) such as alpha-sulfonyl hydroxamic acid derivative (WO 01/55112) or N-hydroxyformamide inhibitor (GW 3333, -005, or -022)) and TNF-bp/s-TNFR (soluble TNF binding protein, see e.g., Arthritis & Rheumatism (1996) Vol. 39, No. 9 (supplement), 5284; and Am. J. Physiol. Heart Circ. Physiol. (1995) Vol. 268, pp. 37-42). TNF antagonists may be soluble TNF receptor (e.g., human p55 or p75) fragments and derivatives, such as 75 kdTNFR-IgG; and TNFα converting enzyme (TACE) inhibitors.

In one embodiment, the other therapeutic agent or prophylactic agent is selected from IL-13 antagonists, such as soluble IL-13 receptors and/or anti-IL-13 antibodies; and IL-2 antagonists, such as IL-2 fusion proteins (e.g., DAB 486-IL-2 and/or DAB 389-IL-2, Seragen, see e.g., Arthritis & Rheumatism (1993) Vol. 36, 1223) and anti-IL-2R antibodies (e.g., anti-Tac (humanized antibody, Protein Design Labs, see Cancer Res. 1990 Mar. 1; 50(5):1495-502)).

In one embodiment, the other therapeutic agent or prophylactic agent is selected from non-depleting anti-CD4 inhibitors such as IDEC-CE9.1/SB 210396 (anti-CD4 antibody, IDEC/SmithKline). In one embodiment, the other therapeutic agent is selected from antagonists (such as antibodies, soluble receptors, or antagonistic ligands) of costimulatory molecules, such as CD80 (B7.1) and CD86 (B7.2); ICOSL, ICOS, CD28, and CTLA4 (e.g., CTLA4-1 g); P-selectin glycoprotein ligand (PSGL); and anti-inflammatory cytokines and agonists thereof (e.g., antibodies). The anti-inflammatory cytokines may include IL-4 (DNAX/Schering); IL-10 (SCH 52000, recombinant IL-10, DNAX/Schering); IL-13; and TGF.

In one embodiment, the other therapeutic agent or prophylactic agent is selected from an anti-inflammatory drug, an immunosuppressant, a metabolic inhibitor, and an enzymatic inhibitor. Non-limiting examples of the drugs or inhibitors that can be used in combination with the IL-22 antagonists described herein, include, but are not limited to, at least one of: non-steroidal anti-inflammatory drug (NSAID) (such as ibuprofen, Tenidap (see e.g., Arthritis & Rheumatism (1996) Vol. 39, No. 9 (supplement), S280)), Naproxen (see e.g., Neuro Report (1996) Vol. 7, pp. 1209-1213), Meloxicam, Piroxicam, Diclofenac, and Indomethacin); Sulfasalazine (see e.g., Arthritis & Rheumatism (1996) Vol. 39, No. 9 (supplement), S281); corticosteroid (such as prednisolone); cytokine suppressive anti-inflammatory drug (CSAID); and an inhibitor of nucleotide biosynthesis (such as an inhibitor of purine biosynthesis (e.g., folate antagonist such as methotrexate) and an inhibitor of pyrimidine biosynthesis (e.g., a dihydroorotate dehydrogenase (DHODH) inhibitor such as leflunomide (see e.g., Arthritis & Rheumatism, vol. 39, No. 9 (supplement), S131, 1996; Inflammation Research, vol. 45, pp. 103-107, 1996).

Other therapeutic agents or prophylactic agents may be conjugated to the antibody include at least one of: corticosteroid (oral, inhaled and local injection); immunosuppressant (such as cyclosporin and tacrolimus (FK-506)); a mTOR inhibitor (such as sirolimus (rapamycin) or a rapamycin derivative (e.g., ester rapamycin derivative such as CCI-779 (Elit. L. (2002) Current Opinion Investig. Drugs 3(8):1249-53; Huang, S. et al. (2002) Current Opinion Investig. Drugs 3(2):295-304))); a therapeutic agent which interferes with the signaling of proinflammatory cytokines such as TNFα and IL-1 (e.g., IRAK, NIK, IKK, p38 or a MAP kinase inhibitor); a COX2 inhibitor (e.g., celecoxib and variants thereof (MK-966), see e.g., Arthritis & Rheumatism, vol. 39, No. 9 (supplement), S81 1996); a phosphodiesterase inhibitor (such as R973401, see e.g., Arthritis & Rheumatism, vol. 39, No. 9 (supplement), S282 1996); a phospholipase inhibitor (e.g., an inhibitor of cytosolic phospholipase 2 (cPLA2) such as trifluoromethyl ketone analogs (U.S. Pat. No. 6,350,892)); an inhibitor of vascular endothelial cell growth factor (VEGF); an inhibitor of the VEGF receptor; and an inhibitor of angiogenesis.

The pharmaceutical compositions may be suitable for injection to subjects. Such compositions may be sterile aqueous solutions or dispersions including sesame oil, peanut oil or aqueous propylene glycol; and sterile powders for the extemporaneous preparation of sterile injectable solutions or dispersions. The compositions must be sterile and must be fluid to the extent that easy syringeability exists. They must be stable under the conditions of manufacture and storage and must be preserved against the contaminating action of microorganisms, such as bacteria and fungi.

Sterile injectable solutions are prepared by incorporating the antibodies in the required amount in the appropriate solvent with one or more of the other ingredients discussed above, as may be required, followed by filtered sterilization. Generally, dispersions are prepared by incorporating the various sterilized antibody solution into a sterile vehicle which contains the basic dispersion medium and the required other ingredients from those enumerated above. In the case of sterile powders for the preparation of sterile injectable solutions, the exemplary methods of preparation are vacuum-drying and freeze-drying techniques which yield a powder of the active ingredient plus any additional desired ingredient from a previously sterile-filtered solution thereof.

The pharmaceutical composition may be in the form of liposomes and/or nanoparticles for the introduction of antibodies or antibody fragments into host cells. The formation and use of liposomes and/or nanoparticles are known to those of skill in the art. Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations The anti-IL-22 antibody, antibody fragment or immunoconjugate may be encapsulated in microcapsules prepared, for example, by coacervation techniques or by interfacial polymerization. For example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions may be employed. Such techniques are disclosed in Remington's Pharmaceutical Sciences 16th edition, Osol, A. Ed. (1980).

Nanocapsules can generally entrap compounds in a stable and reproducible way. To avoid side effects due to intracellular polymeric overloading, such ultrafine particles (sized around 0.1 µm) are generally designed using polymers able to degrade in vivo. Biodegradable polyalkyl-cyanoacrylate nanoparticles that meet these requirements are contemplated for use in the present invention, and such particles may be easily made.

Sustained-release pharmaceutic composition may be prepared. Suitable examples of sustained-release preparations include semipermeable matrices of solid hydrophobic polymers containing the antibody or antibody fragment, which matrices may be in the form of shaped articles, e.g. films, or microcapsules.

Upon formulation, the pharmaceutical compositions will be administered in a manner compatible with the dosage formulation and in such amount as is therapeutically effective. The compositions are easily administered in a variety of dosage forms, such as the type of injectable solutions described above, but drug release capsules and the like can also be employed.

E. Therapeutic and Prophylactic Methods

In one aspect, the invention provides therapeutic and prophylactic methods using the anti-IL-22 antibodies, antibody fragments, variants, derivatives, immunoconjugates or any of the above pharmaceutical compositions. Such methods include in vitro, ex vivo, and in vivo therapeutic and prophylactic methods. In one embodiment, methods of inhibiting an IL-22-mediated signaling pathway are provided. Methods of stimulating or inhibiting a ThIL-17 cell function are provided. Methods of treating inflammatory and/or autoimmune disorders are also provided. Methods of treating disorders associated with IL-22 signaling are further provided. Methods of treating ThIL-17-mediated disorders are also provided.

In one embodiment, a method of inhibiting an IL-22-mediated signaling pathway in a biological system is provided. The method comprises providing an anti-IL-22 antibody, antibody fragment, variants, derivatives, immunoconjugates or any of the above pharmaceutical compositions to the biological system.

In another embodiment, a method of inhibiting a ThIL-17 cell function is provided. The method comprises exposing a ThIL-17 cell to an anti-IL-22 antibody, antibody fragment, variants, derivatives, immunoconjugates or any of the above pharmaceutical compositions. Exemplary ThIL-17 cell functions include, but are not limited to, stimulation of cell-mediated immunity (delayed-type hypersensitivity); recruitment of innate immune cells, such as myeloid cells (e.g., monocytes and neutrophils) to sites of inflammation; and stimulation of inflammatory cell infiltration into tissues.

The anti-IL-22 antibodies, antibody fragments, variants, derivatives, immunoconjugates or any of the above pharmaceutical compositions may be used to treat immune related diseases, thrombotic diseases (thrombosis and atherothrombosis), and cardiovascular diseases. The immune related diseases include arthritis, autoimmune disease, chronic inflammation, inflammation, inflammatory bowel disease, psoriasis, T-cell mediated diseases. The anti-IL-22 antibodies or antibody fragments can act as antagonists to IL-22 to regulate at least one IL-22-mediated immune response, such as acting on epithelial cells in solid tissue and indirectly modulating downstream immune responses, such as blocking expansion of T cell subsets, including, for example, $T_H17$ T cells. In one embodiment, the antibodies, antibody fragments, variants, derivatives, immunoconjugates or any of the above pharmaceutical compositions are used in a method for regulating an immune response. The method comprises contacting IL-22 with an antibody, antibody fragment, variants, derivatives, immunoconjugates or any of the above pharmaceutical compositions of the invention thereby regulating the immune response. In one embodiment, the immune response comprises cell proliferation, cytolytic activity, cytokine secretion, or chemokine secretion.

Accordingly, the antibodies, antibody fragments, variants, derivatives, immunoconjugates or any of the above pharmaceutical compositions of the invention can be used to directly or indirectly inhibit the activity (e.g., proliferation, differentiation, and/or survival) of an immune or hematopoietic cell (e.g., a cell of myeloid, lymphoid, or erythroid lineage, or precursor cells thereof), and, thus, can be used in a method to treat a variety of immune disorders and hyperproliferative disorders. Non-limiting examples of immune disorders that can be treated include, but are not limited to, autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, HIV, Sjogren's syndrome, vasculitis, multiple sclerosis, autoimmune thyroiditis, dermatitis (including atopic dermatitis and eczematous dermatitis), myasthenia gravis, inflammatory bowel disease (IBD), Crohn's disease, colitis, diabetes mellitus (type I); inflammatory conditions of, e.g., the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis); cardiovascular disorders, e.g., cholesterol metabolic disorders, oxygen free radical injury, ischemia; disorders associated with wound healing; respiratory disorders, e.g., asthma and COPD (e.g., cystic fibrosis); acute inflammatory conditions (e.g., endotoxemia, sepsis and septicaemia, toxic shock syndrome and infectious disease); transplant rejection and allergy. In one embodiment, the IL-22-associated disorder is, an arthritic disorder, e.g., a disorder chosen from one or more of rheumatoid arthritis, juvenile rheumatoid arthritis, osteoarthritis, psoriatic arthritis, or ankylosing spondylitis; a respiratory disorder (e.g., asthma, chronic obstructive pulmonary disease (COPD); or an inflammatory condition of, e.g., the skin (e.g., psoriasis), cardiovascular system (e.g., atherosclerosis), nervous system (e.g., Alzheimer's disease), liver (e.g., hepatitis), kidney (e.g., nephritis), pancreas (e.g., pancreatitis), and gastrointestinal organs, e.g., colitis, Crohn's disease and IBD; acute inflammatory conditions, e.g., endotoxemia, sepsis and septicaemia, toxic shock syndrome and infectious disease; multiple organ failure; respiratory disease (ARD); amyloidosis; nephropathies such as glomerulosclerosis, membranous neuropathy, renal arteriosclerosis, glomerulonephritis, fibroproliferative diseases of the kidney, as well as other kidney disfunctions and renal tumors. Because of IL-22's effects on epithelia, anti-IL-22 antibodies can be used to treat epithelial cancers, e.g., carcinoma, melanoma and others. For a description of a rationale for IL-22 inhibition in these and other diseases see WO 2003/083062 (pages 58-75).

In yet another embodiment, a method of treating an autoimmune disorder is provided. The method comprises administering to a mammal in need of such treatment an effective amount of an anti-IL-22 antibody, antibody fragment, variants, derivatives, immunoconjugates or any of the above pharmaceutical compositions. Autoimmune disorders include, but are not limited to, connective tissue disease, multiple sclerosis, systemic lupus erythematosus, inflammatory arthritis (e.g., rheumatoid arthritis), autoimmune pulmonary inflammation, Guillain-Barre syndrome, autoimmune thyroiditis, insulin-dependent diabetes mellitus, uveitis, myasthenia gravis, graft-versus-host disease, autoimmune inflammatory eye disease, psoriasis, arthritis associated with autoimmunity (e.g., rheumatoid arthritis), autoimmune inflammation of the brain, and inflammatory bowel disease. In one embodiment, the autoimmune disorder is an IL-23-mediated autoimmune disorder.

In an embodiment, methods for the treatment of psoriasis and/or disorders characterized by psoriatic symptoms are provided. Psoriasis is considered an autoimmune disease in which T-cells of the immune system recognize a protein in the skin and attack the area where that protein is found, causing the too-rapid growth of new skin cells and painful, elevated, scaly lesions. These lesions are characterized by hyperproliferation of keratinocytes and the accumulation of activated T-cells in the epidermis of the psoriatic lesions. Although the initial molecular cause of disease is unknown, genetic linkages have been mapped to at least 7 psoriasis susceptibility loci (Psor1 on 6p21.3, Psor2 on 17q, Psor3 on 4q, Psor4 on 1 cent-q21, Psor5 on 3q21, Psor6 on 19p13, and Psor7 on 1p). Some of these loci are associated with other autoimmune/inflammatory diseases, including rheumatoid arthritis, atopic dermatitis, and inflammatory bowel disease (IBD). Current approaches to the treatment of psoriasis include the administration of IL-12 or TNF-α antagonists. See, e.g., Nickoloff et al. (2004) *J. Clin. Invest.*, vol. 113, pp. 1664-1675; Bowcock et al. (2005) *Nat. Rev. Immunol.*, vol. 5, pp. 699-711; Kauffman et al. (2004) *J. Invest. Dermatol.*, vol. 123, pp. 1037-1044. It is known that a distinct IL-23/IL-22 signaling pathway is implicated in the pathogenesis of psoriasis. Accordingly, therapeutics that modulate this signaling pathway may provide an alternative to or may complement other approaches to psoriasis treatment.

In one embodiment, a method of treating psoriasis comprises administering to a patient an effective amount of an anti-IL-22 antibody, antibody fragment, variants, derivatives, immunoconjugates or any of the above pharmaceutical compositions. In various embodiments, the method further comprises administering (either in the same pharmaceutical composition or a separate pharmaceutical composition) at least one additional therapeutic agent. In one such embodiment, the additional therapeutic agent is at least one antagonist of a cytokine selected from IL-19, IL-20, and IL-24. Such antagonists include, but are not limited to, an antibody that binds IL-19, IL-20, IL-24, IL-20Ra, IL-20Rb, or IL-10R2. Any number of such antibodies may be selected in any combination. In another embodiment, the additional therapeutic agent is an agent known to be effective in the treatment of psoriasis. Certain of such therapeutic agents are described, e.g., in Nickoloff et al. (2004) *J. Clin. Invest.* 113:1664-1675; Bowcock et al. (2005) *Nat. Rev. Immunol.* 5:699-711; and Kauffman et al. (2004) *J. Invest. Dermatol.* 123:1037-1044. Such therapeutic agents include, but are not limited to, a therapeutic agent that targets T cells, e.g., efalizumab and/or alefacept; an antagonist of IL-12, e.g., a blocking antibody that binds IL-12 or its receptor; and an antagonist of TNF-α, e.g., a blocking antibody that binds TNF-α or its receptor.

In one embodiment, a method of treating multiple sclerosis is provided. The method comprises administering to a patient an effective amount of an anti-IL-22 antibody, antibody fragment, variants, derivatives, immunoconjugates or any of the above pharmaceutical compositions. Multiple sclerosis is a central nervous system disease that is characterized by inflammation and loss of myelin sheaths—the fatty material that insulates nerves and is needed for proper nerve function.

In one embodiment, the method of treating arthritis comprises administering to a patient an effective amount of an anti-IL-22 antibody, antibody fragment, variants, derivatives, immunoconjugates or any of the above pharmaceutical compositions. Arthritis is a disease characterized by inflammation in the joints. Rheumatoid Arthritis (RA) is the most frequent form of arthritis, involving inflammation of connective tissue and the synovial membrane, a membrane that lines the joint. The inflamed synovial membrane often infiltrates the joint and damages joint cartilage and bone. IL-22 and IL-22R protein and/or transcript is associated with both human diseases. In RA synovial biopsies, IL-22 protein is detected in vimentin$^+$ synovial fibroblasts and some CD68$^+$ macrophages while IL-22R is detected in synovial fibroblasts. Treatment of synovial fibroblasts with IL-22 induces the production of monocyte chemoattractant protein-1, MCP-1, as well as general metabolic activity (Ikeuchi, H., et al., (2005) *Arthritis Rheum.*, vol. 52, pp. 1037-46). Inhibitors of IL-22 ameliorate symptoms of rheumatoid arthritis (WO 2005/000897 A2; U.S. Pat. No. 6,939, 545). Increased secretion of inflammatory cytokines and chemokines, and more importantly, increased disease resulting from immune responses that are dependent on IL-22 may be treated by the methods of this invention. Similarly, the methods of this invention may be used to treat RA or other arthritic diseases in humans.

In one embodiment, the method of treating transplant rejection comprises administering to a patient an effective amount of an anti-IL-22 antibody, antibody fragment, variants, derivatives, immunoconjugates or any of the above pharmaceutical compositions. Transplant rejection is the immunological phenomenon where tissues from a donor are specifically "attacked" by immune cells of the host. The principle "attacking" cells are T cells, whose T cell receptors recognize the donor's MHC molecules as "foreign." This recognition activates the T cells, which proliferate and secrete a variety of cytokines and cytolytic proteins that ultimately destroy the transplant. Mix lymphocyte reaction (MLR) and transplantation models have been described by *Current Protocols in Immunology*, Second Edition, Coligan et al. eds., John Wiley & Sons, 1994; Kasaian et al. (*Immunity* (2002) 16: 559-569); Fulmer et al. (*Am. J. Anat.* (1963) 113: 273-285), and Lenschow et al. (*Science* (1992) 257: 789-792). The methods of this invention may be used to reduce the MLR and treat transplant rejection and related diseases (e.g., graft versus host disease) in humans that are dependent on IL-22.

In one embodiment, the invention provides a method to treat hyperproliferative disorders associated with aberrant activity of IL-22-responsive cells and IL-22R/IL-10R2-responsive cells. The method comprises administering the anti-IL-22 antibodies, antibody fragments, variants, derivatives, immunoconjugates or any of the above pharmaceutical compositions to inhibit or reduce hyperproliferation of IL-22 and/or IL-22R and/or IL-10R2-responsive cells in a subject. IL-22 and IL-22R expression is constitutive on epithelial cells in a number of tissues including, but not limited to, pancreas, lung, skin, gut, liver, kidney (Kotenko, S. V. et al. (2001) *J. Biol. Chem.*, vol. 276, pp. 2725-32; Xie, M. H. et al. (2000) *J. Biol. Chem.*, vol. 275, pp. 31335-9; Wolk, K. et al. (2004) *Immunity*, vol. 21, pp. 241-54). In addition, IL-22 receptor complex is also expressed on the surface of fibroblasts from the diseased joint and normal gut (Ikeuchi, H. et al. (2005) *Arthritis Rheum.*, vol. 52, pp. 1037-46; Andoh, A. et al. (2005) *Gastroenterology*, vol. 129, pp. 969-84). Neoplastic derivatives of these cell types may be hyper responsive to IL-22, modulating these cells ability to survive in the organism. Hence the methods of the invention may be used to inhibit the progression of such neoplasms, e.g. squamous cell carcinomas, basal cell carcinomas, transitional cell papillomas and carcinomas, adenomas, adenocarcinoma, linitis plastica, insulinoma, glucagonoma, gastrinoma, vipoma, cholangiocarcinoma, hepatocellular carcinoma, adenoid cyctic carcinoma, carcinoid tumor of appendix, prolactinoma, oncocytoma, hurthle cell adenoma, renal cell carcinoma, Grawitz tumor, multiple endocrine adenomas, endometroid adenoma, adnexal and skin appendage neoplasms, mucoepidermoid neoplams, cystic, mucinous and serous neoplasms, cystadenoma, pseudomyxoma peritonei, ductal, lobular and medullary neoplasms, acinar cell neoplasms, complex epithelial neoplasms, Warthin's tumor, thymoma, specialized gonadal neoplasms, sex cord-stromal tumor, thecoma, granulosa cell tumor, arrhenoblastoma, sertoli-leydig cell tumor, paraganglioma, pheochromocytoma, *glomus* tumor, malanocytic nevus, malignant melanoma, melanoma, nodular melanoma, dysplastic nevus, lentigo maligna, superficial spreading melanoma, or acral lentiginous melanoma.

In yet another embodiment, a method of inhibiting tumor progression is provided. The method comprises administering to a mammal an effective amount of an anti-IL-22 antibody, antibody fragment, variants, derivatives, immunoconjugates or any of the above pharmaceutical compositions.

In another embodiment, the invention provides a method of decreasing, inhibiting or reducing an acute phase response in a subject. The method includes administering to the subject an anti-IL-22 antibody, antibody fragment, variants, derivatives, immunoconjugates or any of the above pharmaceutical compositions in an amount sufficient to decrease, inhibit or reduce the acute phase response in the subject. In one embodiment, the subject is a mammal, e.g., a human suffering from an IL-22-associated disorder as described herein, including, e.g., respiratory disorders, inflammatory disorders and autoimmune disorders. In one embodiment, the IL-22 binding agent is administered locally, e.g., topically, subcutaneously, or other administrations that are not in the general circulation.

In another embodiment, the invention provides a method of administering the anti-IL-22 antibodies, antibody fragments, variants, derivatives, immunoconjugates or any of the above pharmaceutical compositions simultaneously or sequentially with an antibody against other immune disease associated- or tumor associated-antigens, such as antibodies that bind to CD20, CD11a, CD18, ErbB2, EGFR, ErbB3, ErbB4, or vascular endothelial factor (VEGF). Alternatively, or in addition, two or more antibodies binding the same or two or more different antigens disclosed herein may be coadministered to the patient. In certain embodiments, it may be beneficial to also administer one or more cytokines to a patient. In certain embodiments, an anti-IL-22 antibody, antibody fragment, variants, derivatives, immunoconjugates or any of the above pharmaceutical compositions of the invention is coadministered with a growth inhibitory agent. For example, the growth inhibitory agent may be administered before, after, or contemporaneously with administration of the composition. Suitable dosages for the growth inhibitory agent are those presently used and may be lowered due to the combined action (synergy) of the growth inhibitory agent and the composition.

In each and every method described above, the antibodies, antibody fragments, variants, derivatives, immunoconjugates or any of the above pharmaceutical compositions of the invention can be used alone, as immunoconjugates or in combination with other agents in a therapy. For instance, an antibody, antibody fragment, variants, derivatives, immunoconjugates or any of the above pharmaceutical compositions of the invention may be co-administered with at least one additional therapeutic agent. In certain embodiments, an additional therapeutic agent is an anti-angiogenic agent. In certain embodiments, an additional therapeutic agent is a VEGF antagonist (in some embodiments, an anti-VEGF antibody, for example bevacizumab). In certain embodiments, an additional therapeutic agent is an EGFR antagonist (in some embodiment, erlotinib). In certain embodiments, an additional therapeutic agent is a chemotherapeutic agent and/or a cytostatic agent. In certain embodiments, an additional therapeutic agent is a taxoid (e.g., paclitaxel) and/or a platinum agent (e.g., carboplatinum). In certain embodiments the additional therapeutic agent is an agent that enhances the patient's immunity or immune system.

Such combination therapies noted above encompass combined administration (where two or more therapeutic agents are included in the same or separate formulations), and separate administration, in which case, administration of the antibody, antibody fragment, variants, derivatives, immunoconjugates or any of the above pharmaceutical compositions can occur prior to, simultaneously, and/or following, administration of the additional therapeutic agent and/or adjuvant. Antibodies, antibody fragments, variants, derivatives, immunoconjugates or any of the above pharmaceutical compositions can also be used in combination with radiation therapy.

F. Diagnostic Methods

In some embodiments, the anti-IL-22 antibodies, antibody fragments, variants, derivatives, immunoconjugates or any of the above pharmaceutical compositions provided herein may be used for detecting, quantitatively or qualitatively, the presence of IL-22 in a biological sample. In certain embodiments, a biological sample comprises a cell or tissue, such as breast, pancreas, esophagus, lung and/or brain cells or tissue.

In an exemplary embodiment, antibodies, antibody fragments, variants, derivatives, immunoconjugates or any of the above pharmaceutical compositions of the invention may be labelled with a detectable molecule or substance, such as a fluorescent molecule, a radioactive molecule or any other label known in the art as above described. For example, an antibody of the invention may be labelled with a radioactive molecule. Suitable radioactive molecules include but are not limited to radioactive atoms used for scintigraphic studies such as $^{123}$I, $^{124}$I, $^{111}$In and, $^{186}$Re, $^{188}$Re. Alternatively, antibodies or antibody fragments of the invention may also be labelled with a spin label for nuclear magnetic resonance (NMR) imaging, such as iodine-123, iodine-131, indium-Ill, fluorine-19, carbon-13, nitrogen-15, oxygen-17, gadolinium, manganese or iron. Following administration of the antibody, the distribution of the radiolabeled antibody within the patient is detected. Any suitable known method can be used. Some non-limiting examples include, computed tomography (CT), position emission tomography (PET), magnetic resonance imaging (MRI), fluorescence, chemiluminescence and sonography.

In certain embodiments, the labels include labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In one embodiment, a method of diagnosing psoriasis in a mammal is provided, the method including detecting the level of expression of a gene encoding an IL-22 or IL-22R polypeptide in a test sample of tissue cells obtained from the mammal, wherein a higher expression level in the test sample as compared to a control sample (e.g., a sample of known normal tissue cells of the same cell type) indicates the presence of psoriasis in the mammal from which the test sample was obtained. The detection may be qualitative or quantitative. In one embodiment, the test sample comprises blood or serum. In one embodiment, detecting the level of expression of a gene encoding an IL-22 or IL-22R polypeptide comprises (a) contacting an anti-IL-22 antibody or an anti-IL-22R antibody, antibody fragment, with a test sample obtained from the mammal, and (b) detecting the formation of a complex between the antibody and an IL-22 or IL-22R polypeptide in the test sample. The antibody may be linked to a detectable label. Complex formation can be monitored, for example, by light microscopy, flow cytometry, fluorimetry, or other techniques known in the art. The test sample may be obtained from an individual suspected of having psoriasis.

Antibodies, antibody fragments, variants, derivatives, immunoconjugates or any of the above pharmaceutical compositions of the invention may be used in a method for diagnosing and staging of cancer and diseases associated with IL-22 overexpression. Cancers associated with IL-22 overexpression may include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma, sarcomas, hematological cancers (leukemias), astrocytomas, various types of head and neck cancer and other IL-22 overexpressing hyperproliferative diseases.

Antibodies, antibody fragments, variants, derivatives, immunoconjugates or any of the above pharmaceutical compositions of the invention may be used in a method for diagnosing diseases of the immune system for which IL-22 expression is increased or decreased. In a particular embodiment, the invention provides a method of diagnosing a disease associated with the expression or overexpression of IL-22. Examples of such diseases may include immune related diseases, thrombotic diseases (thrombosis and atherothrombosis), and cardiovascular diseases. The immune related diseases include arthritis, autoimmune disease, chronic inflammation, inflammation, inflammatory bowel disease, psoriasis, and T-cell mediated diseases.

In one embodiment, an anti-IL-22 antibody fragment, variants, derivatives, immunoconjugates or any of the above pharmaceutical compositions for use in a method of diagnosis or detection is provided. In a further aspect, a method of detecting the presence of IL-22 in a biological sample is provided. In a further aspect, a method of quantifying the amount of IL-22 in a biological sample is provided. In certain embodiments, the method comprises contacting the biological sample with an anti-IL-22 antibody, antibody fragment, variants, derivatives, immunoconjugates or any of the above pharmaceutical compositions as described herein under conditions permissive for binding to IL-22, and detecting whether a complex is formed. Such a method may be carried out in vitro or in vivo. In one embodiment, an anti-IL-22 antibody, antibody fragment, variants, derivatives, immunoconjugates or any of the above pharmaceutical compositions is used to select subjects eligible for therapy. In some embodiments, the therapy will include administration of an anti-IL-22 antibody, antibody fragment, variants, derivatives, immunoconjugates or any of the above pharmaceutical compositions to the subject.

In another embodiment, the present invention concerns a diagnostic kit containing an anti-IL-22 antibody, antibody fragment, variants, derivatives, immunoconjugates or any of the above pharmaceutical compositions in suitable packaging. The kit may contain instructions for using the composition to detect an IL-22 or IL-22R polypeptide. In one aspect, the diagnostic kit is a diagnostic kit for psoriasis.

G. Articles of Manufacture and Kits

In another aspect of the invention, an article of manufacture containing the anti-IL-22 antibody, antibody fragment, variants, derivatives, immunoconjugates or any of the above pharmaceutical compositions for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is anti-IL-22 antibody, antibody fragment, variants, derivatives, immunoconjugates or any of the above pharmaceutical compositions of the invention. The label or package insert indicates that the composition is used for treating the condition of choice. Moreover, the article of manufacture may comprise (a) a first container with a composition contained therein, wherein the composition comprises an anti-IL-22 antibody, antibody fragment, variants, derivatives, immunoconjugates or any of the above pharmaceutical compositions; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include more than one of an anti-IL-22 antibody, antibody fragment, variants, derivatives, immunoconjugates or any of the above pharmaceutical compositions.

Finally, the invention also provides kits including at least one anti-IL-22 antibody, antibody fragment, variants, derivatives, immunoconjugates or any of the above pharmaceutical compositions of the invention. The kits may be used in detecting IL-22 expression (increase or decrease), or in therapeutic or diagnostic assays. Kits of the invention can contain an antibody, antibody fragment, variants, derivatives, immunoconjugates or any of the above pharmaceutical compositions coupled to a solid support, e.g., a tissue culture plate or beads (e.g., sepharose beads). Kits can be provided which contain antibodies for detection and quantification of IL-22 in vitro, e.g. in an ELISA or a Western blot. Such antibodies useful for detection may be provided with a label such as a fluorescent or radioactive label.

The kits further contain instructions on the use thereof. In some embodiments, the instructions comprise instructions required by the U.S. Food and Drug Administration for in vitro diagnostic kits. In some embodiments, the kits further comprise instructions for diagnosing the presence or absence of cerebrospinal fluid in a sample based on the presence or absence of IL-22 in said sample. In other embodiments, the kits further comprise one or more enzymes, enzyme inhibitors or enzyme activators. In still other embodiments, the kits further comprise one or more chromatographic compounds. In yet other embodiments, the kits further comprise one or more compounds used to prepare the sample for spectroscopic assay. In further embodiments, the kits further comprise comparative reference material to interpret the presence or absence of IL-22 according to intensity, color spectrum, or other physical attribute of an indicator.

The following examples are illustrative, but not limiting, of the anti-IL-22 antibodies of the present disclosure. Other suitable modifications and adaptations of the variety of conditions and parameters normally encountered in the field, and which are obvious to those skilled in the art, are within the scope of the disclosure.

EXAMPLES

Example 1: Anti-IL-22 Antibodies

Mice were immunized with human IL-22 to generate a functional hybridoma clone 3C3 that expressed a murine monoclonal antibody (3C3 mAb) binding to human IL-22 (hIL-22). The binding affinity of the 3C3 mAb to hIL-22 is approximately 100 pM (measured by SPR analysis). However, 3C3 mAb was not able to bind to mouse IL-22 (mIL-22). The 3C3 mAb is able to block the induction of Stat3 phosphorylation by hIL2 in HepG2 cells. The 3C3 mAb was humanized to produce a humanized antibody hum10.

Hum10 was chosen for Comprehensive Positional Evolution (CPE™) to create a CPE™ library containing hum10 variants. Each position in the six CDRs of hum10 was substituted with at least 15 amino acids to create the antibody variants. The positions of the CDRs in hum10 are shown in FIG. 1 with some exemplary substitutions. There are total of 63 positions in the six CDRs. The CPE™ library contained a total of 1068 antibody variants (472 mutants with mutations in the light chain CDRs and 596 mutants with mutations in the heavy chain CDRs). Each antibody variant was verified by sequencing. The CPE™ variants were transfected into CHO cells in 96 well format and the supernatant was collected at 48 hours post transfection. The expression level of the CPE™ variants in the supernatant was determined by quantitation ELISA using commercial purified human IgG as standard.

The CPE™ library was screened for antibodies that were able to bind to both human IL-22 and mouse IL-22 with high affinity. Specifically, the CPE™ variants were screened by affinity ELISA for mouse IL-22 (mIL-22) binding affinity. The hum10 was included in every affinity ELISA plate as a control. The CPE™ variants with increased binding affinity to mIL-22 compared to hum10 were scored as primary CPE™ hits. The primary CPE™ hits were re-arrayed, re-transfected, and screened again by affinity ELISA and also by titration ELISA using both mIL-22 and human IL-22 (hIL-22) for antibodies that bind to both mIL-22 and hIL-22. The screening identified 10 mutant antibodies shown in Table 1. These 10 mutant antibodies were selected based on ELISA data and sequence diversity, ability to scaled up and purified.

Example 2: Purified Anti-IL-22 Antibodies

The selected anti-IL-22 antibodies were expressed in CHO cells and the expressed antibodies were purified for further testing. To verify the purity of the antibodies, they were loaded in a 10% SDS PAGE gel. The antibodies showed a single band under non-reducing condition (FIG. 4, left half), indicating intact antibodies with paired light chains and heavy chains. Under a reducing condition, the antibodies were separated into light chains and heavy chains, which showed as two bands in each lane (FIG. 4, right half). Lane M showed the molecular weight markers in kDa for each band marked on the gel.

The purified antibodies were also analyzed by size exclusion chromatography analysis on a Superdex200 5/150 GL column with a flow rate: 0.3 ml/min. The washing buffer was 1×PBS buffer. A total of 50 µl antibody was injected into the column. The SEC analysis produced a single peak (FIG. 5A-5C), indicating that the antibodies are in high purity. FIG. 5A shows the purity of CPS02 and FIG. 5B shows the purity of CPS09. A commercially available human IgG standard was used as control and its results are shown in FIG. 5C. The single peak indicated that the purified antibodies were sufficiently pure and did not form aggregates under the test conditions.

Example 3: Specificity of Anti-IL-22 Antibodies

The specificity of the 10 antibodies of Table 1 was assayed with ELISA using both human and mouse IL-22, as well as related antigens (human IL19, human IL20, human IL24, human IL26, INF alpha A, INF-γ, INF-λ1, INF-2 and a non-specific antigen). Plates were coated with 100 µl antigens at a concentration of 1 µg/ml. The plates were exposed to the antibodies at a concentration of 100 ng/ml. The bound antibodies were detected with anti-hIgG-HRP by the ELISA assay.

Figure 6:
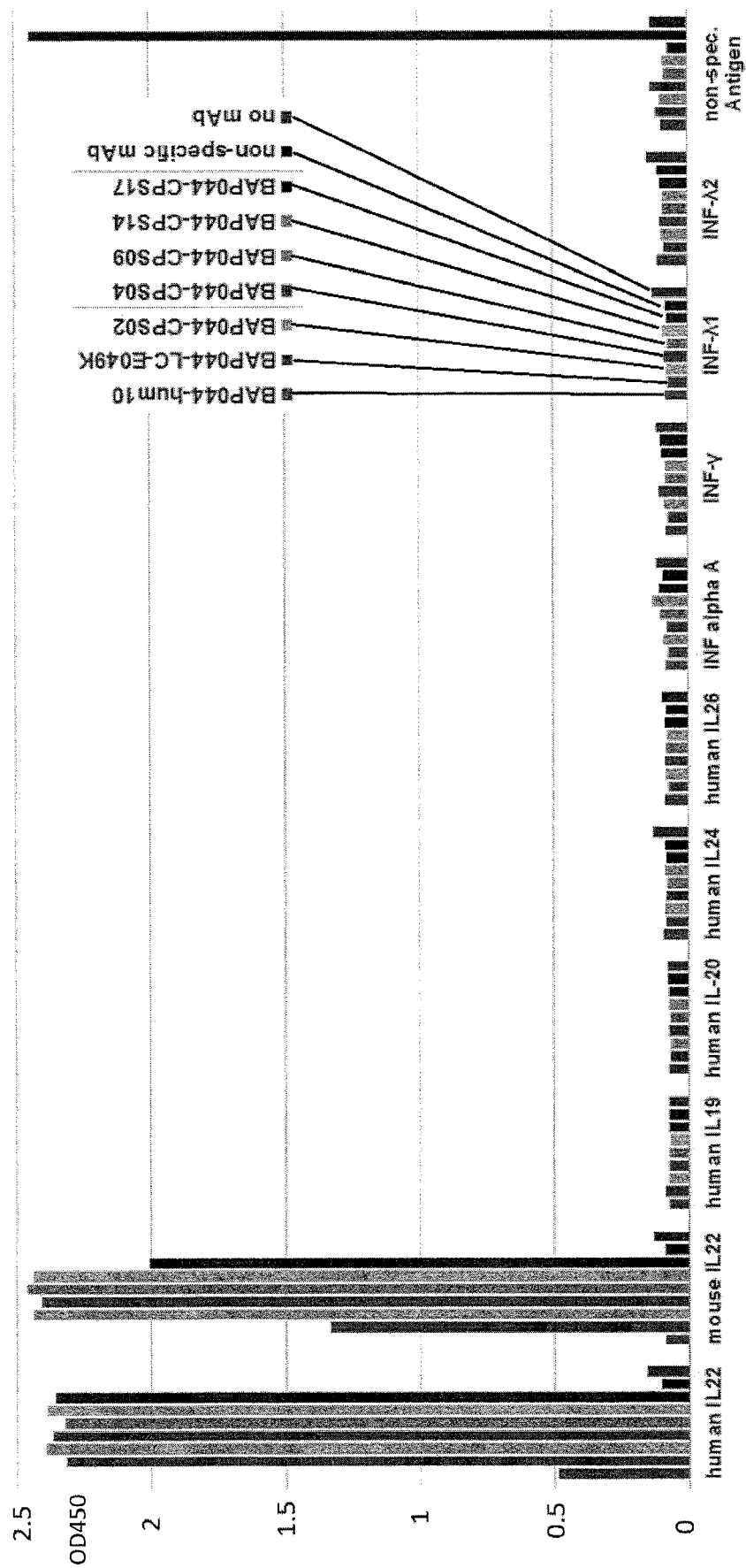
FIG. 6 shows the specificity of the antibodies of the present invention to human and mouse IL-22, as well as other related antigens.

The 10 antibodies of Table 1 where found to be able to bind to human and mouse IL-22 with comparable affinity, whereas they showed very low affinity to the related antigens (FIG. 6). This demonstrates that the 10 antibodies are specific to human and mouse IL-22, with little affinity to other related antigens.

Example 4: Binding Affinity to mIL-22 and hIL-22 of the Anti-IL-22 Antibodies

The affinity of the 10 antibodies of Table 1 was measured by Surface Plasma Resonance (SPR) using a capture assay on a SPR-2 instrument (SierraSensors, Hamburg, Germany). The antigens hIL-22 and mIL-22 were immobilized on chips. The running buffer for the assay contained 10 mM HEPES with a pH of 7.4, 500 mM NaCl, and 0.05% TWEEN® 20. The buffer had a flow rate of 25 µl/min during the assay. The off-rate was measured for 6 minutes. Binding constants were calculated using the curve fitting software Analyzer2 (Sierra Sensors). Sensorgrams were analyzed with the instrument specific software and with BIAevaluation 4.1 software. The binding data were analyzed using the Langmuir 1:1 model (human IL-22) or a model for a heterogeneous ligand (mouse IL-220).

The antibodies were tested at four different concentrations of each antibody: 0.33 nM, 0.67 nM, 3.3 nM, 6.7 nM for hIL-22; 1, 2, 10.20 nM for mIL-22. Antibody CPE-LC-E049K was used as a control. Binding curves were generated and used to calculate the Ka, Kd and $K_D$ of the antibodies which are shown in Table 2.

Example 5: Induction of Phosphorylation of Stat3

30,000 human HepG2 cells were seeded in 96 well plates and serum starved overnight. Three-fold dilutions of anti-IL-22 antibodies and control hum10 antibody at concentrations of 0.11 µg/mL, 0.33 µg/mL, 1 µg/mL, and 3 µg/mL were incubated with 200 ng/ml of hIL-22 or mIL-22 at 37° C. for one hour then added to the serum starved human HepG2 cells. The HepG2 cells were incubated with the antibody-IL-22 mixture at 37° C. for 20 minutes. After incubation, HepG2 cells were washed with PBS and lysed. Half of the cell lysate was used to determine the level of phosphorylated Stat3 using Cell Signaling kit #7300 following the vendor's protocol and the other half of the cell lysate was used to determine the level of total Stat3 by Western blot analysis using a Santa Cruz rabbit polyclonal antibody (Sc-7179) against human Stat3.

The inhibition of Stat3 phosphorylation by the anti-IL-22 antibodies through binding to human IL-22 is shown in FIG. 7A and the inhibition of Stat3 phosphorylation through binding to mouse IL-22 is shown in FIG. 7B. The negative control human IgG antibody showed no inhibition of Stat3 phosphorylation. The selected anti-IL-22 antibodies showed dose dependent inhibition of Stat3 phosphorylation (FIGS. 7A-7B).

Example 6: Inhibition of CXCL1 Production

Different concentrations of the anti-IL-22 antibodies were incubated with HT29 cells that normally produce cytokine CXCL1. The production of CXCL1 by the HT29 cells over time was measured and the results are shown in FIG. 8. The inhibition of CXCL1 production by the antibodies was dose dependent, indicating the role of the antibodies in inhibiting cytokine production.

Example 7: Pharmacokinetics of Anti-IL-22 Antibodies in Mice

Two anti-IL-22 antibodies CPS02 and CPS09 were tested in NOD SCID mice. The antibodies were injected via IV at two dosages: 0.3 mg/kg and 10 mg/kg. Three mice were used for each dose group. Blood samples were retrieved from the mice at 10 min, 1 h, 3 h 7 h, 24 h, 48 h, 96 h, 168 h, 240 h and 336 h after the IV injection. The concentrations of the injected antibodies in the blood samples were measured by solid phase ELISA.

Figure 9A:
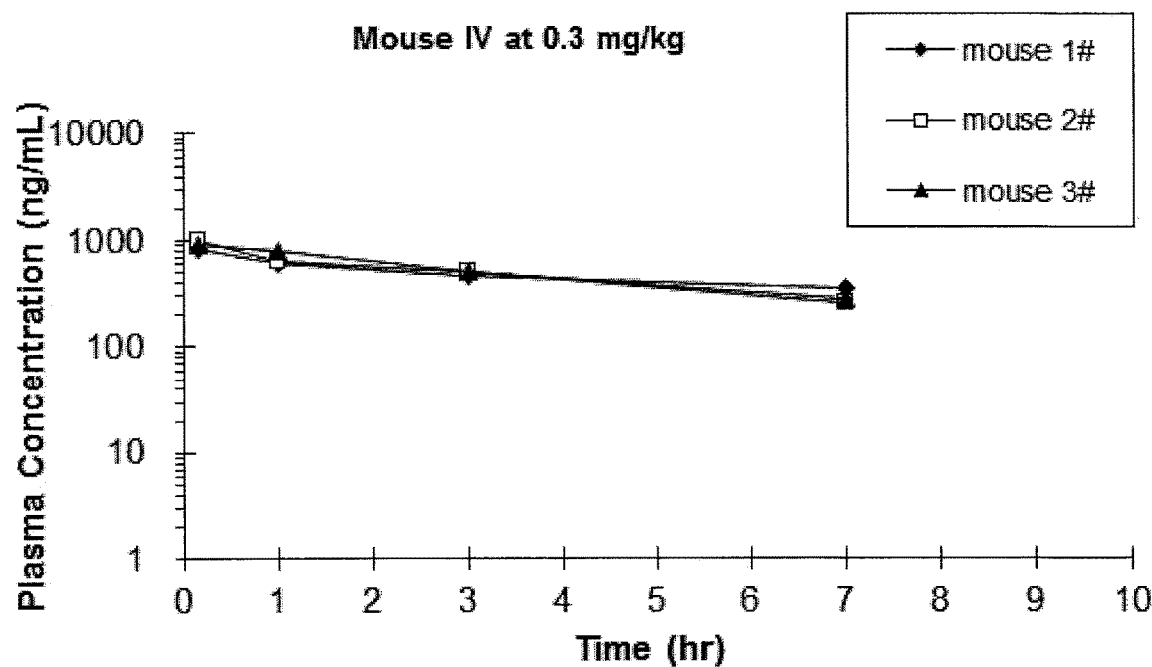
FIGS. 9A-9B show blood plasma concentrations of the antibody CPS02 in mice over time after different injection doses.
Figure 9B:
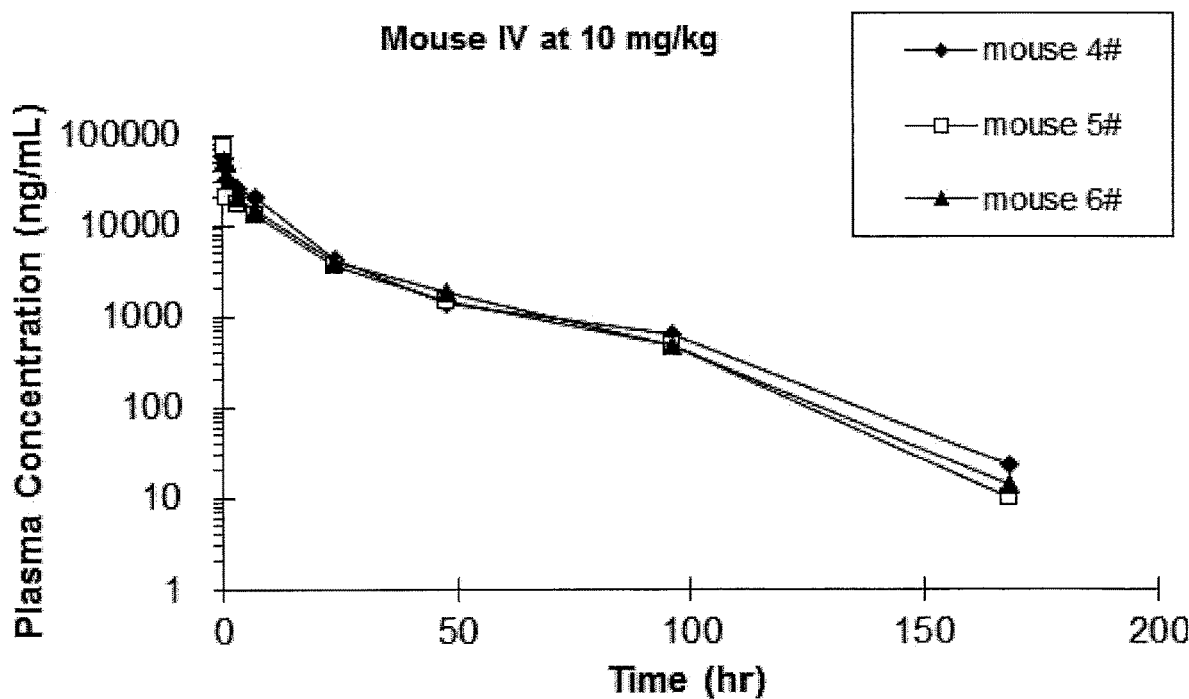
Figure 10A:
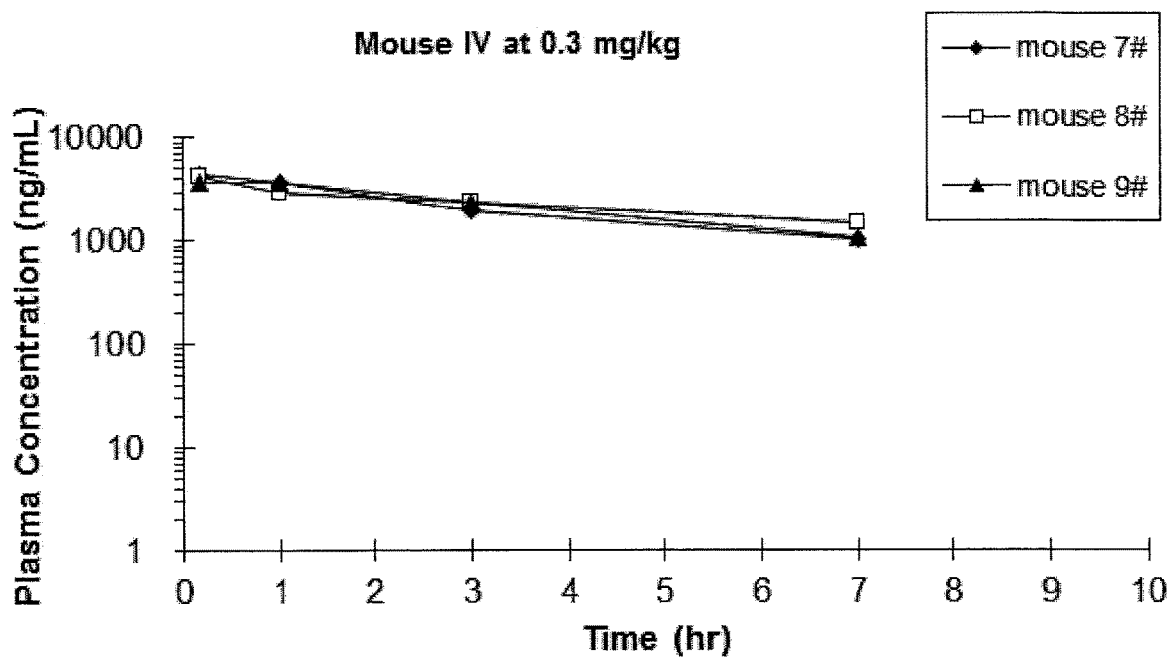
FIGS. 10A-10B show blood plasma concentrations of the antibody CPS09 in mice over time after different injection doses.
Figure 10B:
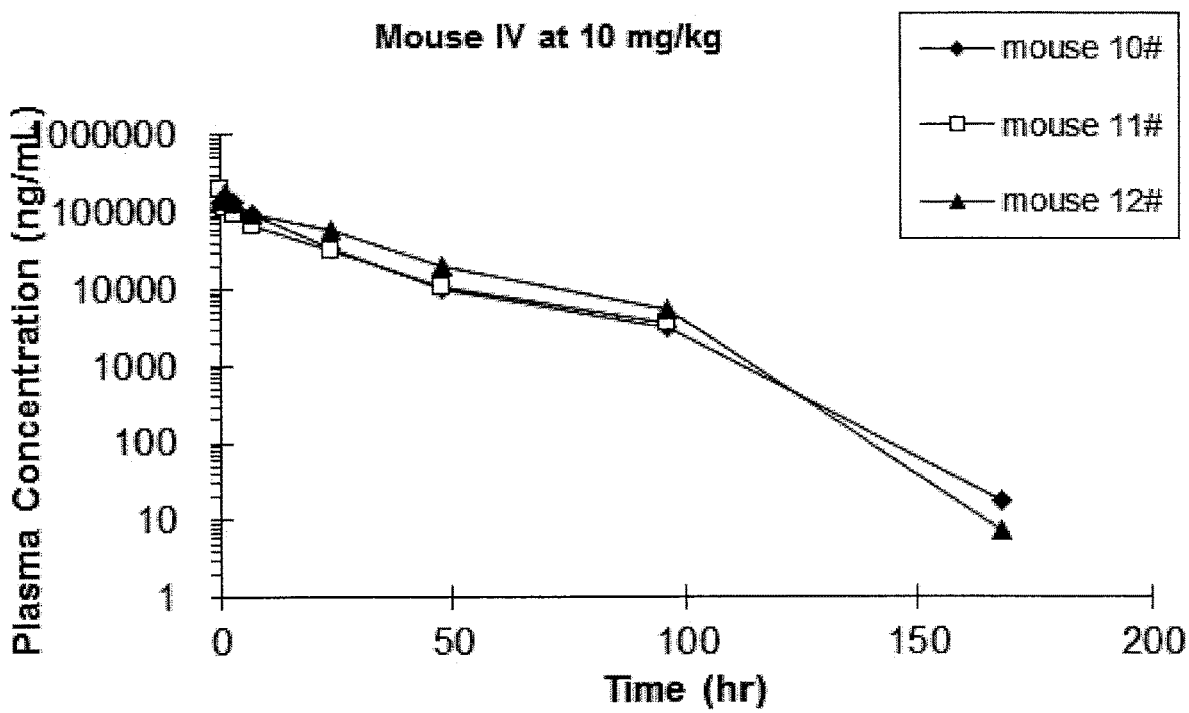

The antibodies had a long half-life in the mice as shown in FIGS. 9A-9B for CPS02 and FIGS. 10A-10B for CPS09. The half-life for CPS02 in mice was about 18 hours after a 10 mg/kg injection. The half-life for CPS09 in mice was about 16 hours after a 10 mg/kg injection.

Example 8: Inhibition of IL-22 Induced Acute Phase Response

5 µg mIL-22 was used to stimulate an acute phase response in mice. The acute phase response was measured by the concentration of serum amyloid (SAA) in the blood of the mice. The anti-IL-22 antibodies were administered at two different dosage levels to inhibit the IL-22 induced acute phase response: 5 µg and 50 µg. Five mice were used for each dose group. The SAA concentrations were measured at 24 hours after injection of IL-22 and/or antibodies and the results are shown in FIG. 11.

When only mIL-22 was injected into the mice, the mice produced high levels of SAA. When only anti-IL-22 antibodies were injected into the mice, the SAA concentrations in the mice were low due to lack of stimulus (mIL-22, right panel of FIG. 11). When both mIL-22 and anti-IL-22 antibodies were injected to the mice, the SAA concentrations in the mice were significantly lower than when only mIL-22 was used, indicating that the anti-IL-22 antibodies effectively inhibited the acute phase response in mice (left panel of FIG. 11).

Example 9: Treatment of Imiquimod-Induced Psoriasis in Mice

Figure 12:
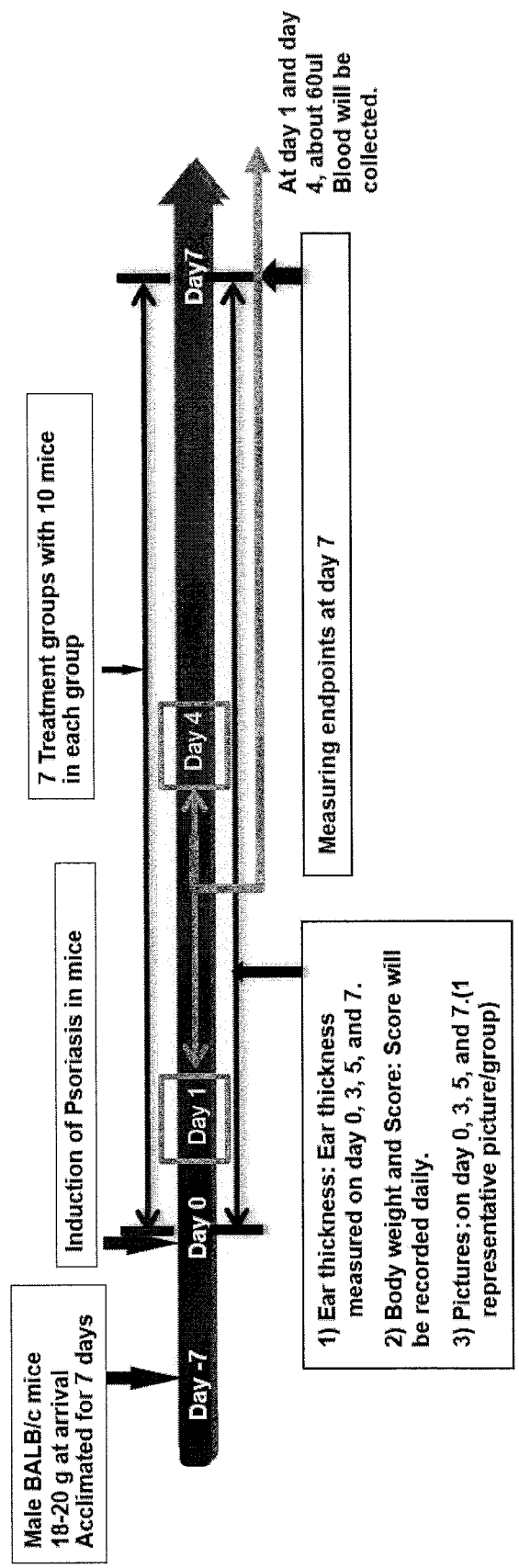
FIG. 12 shows the study design for treating a mouse psoriasis model induced by imiquimod.
Figure 13:
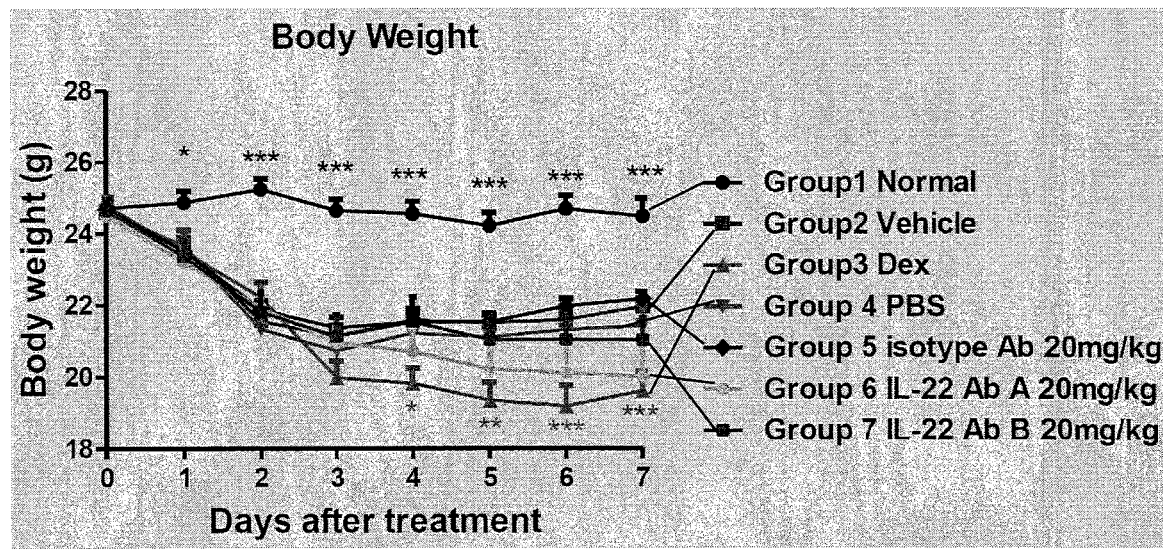
FIG. 13 shows changes of body weight of the treated mice during the treatment period following the study design shown in FIG. 12.
Figure 14:
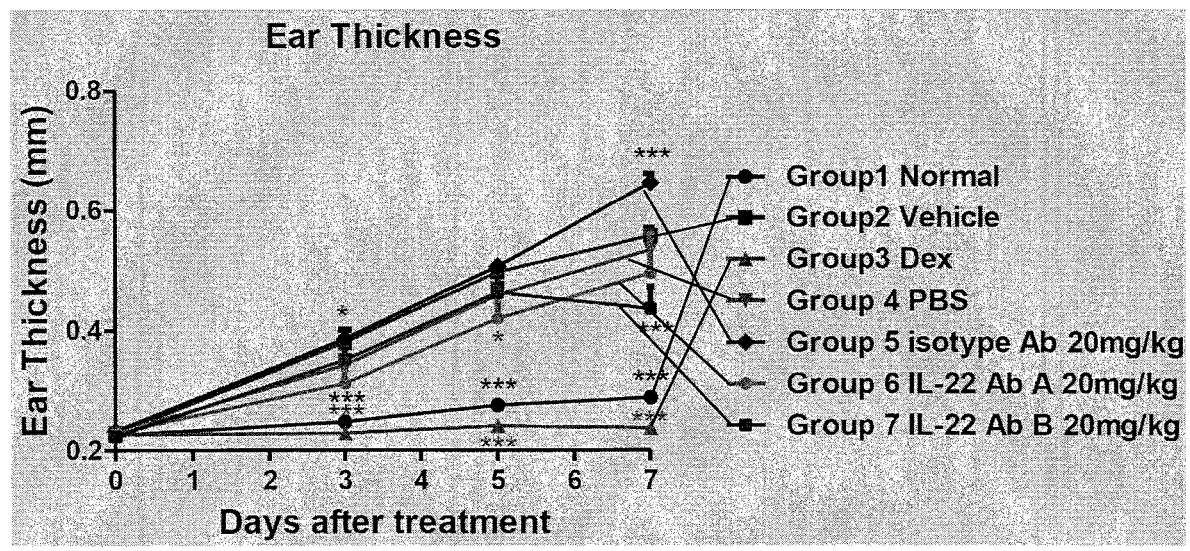
FIG. 14 shows changes of ear thickness of the treated mice during the treatment period following the study design shown in FIG. 12.
Figure 15:
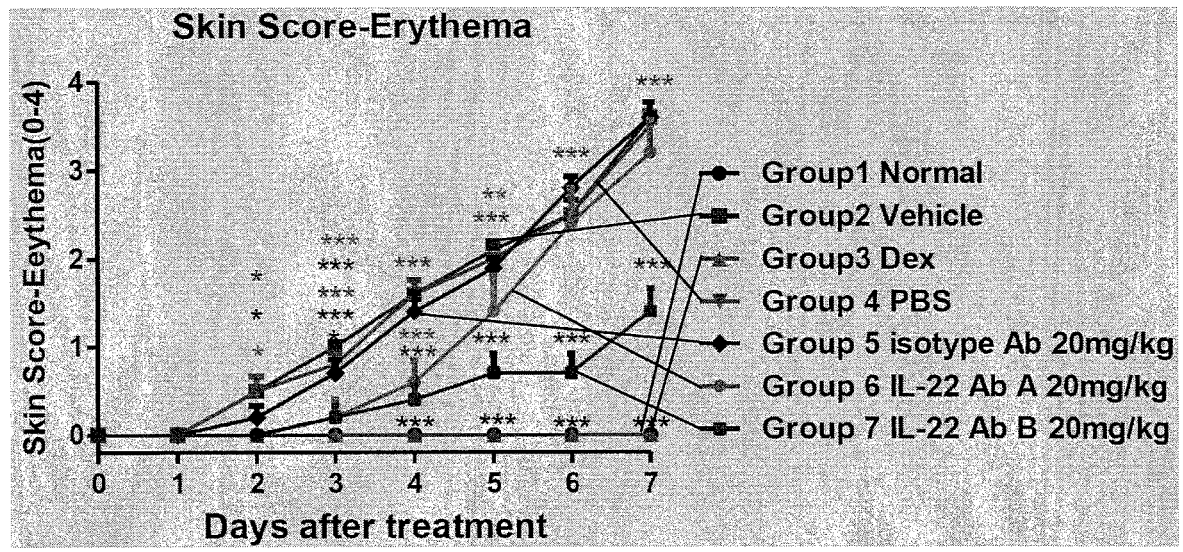
FIG. 15 shows changes of skin erythema score of the treated mice during the treatment period following the study design shown in FIG. 12.
Figure 16:
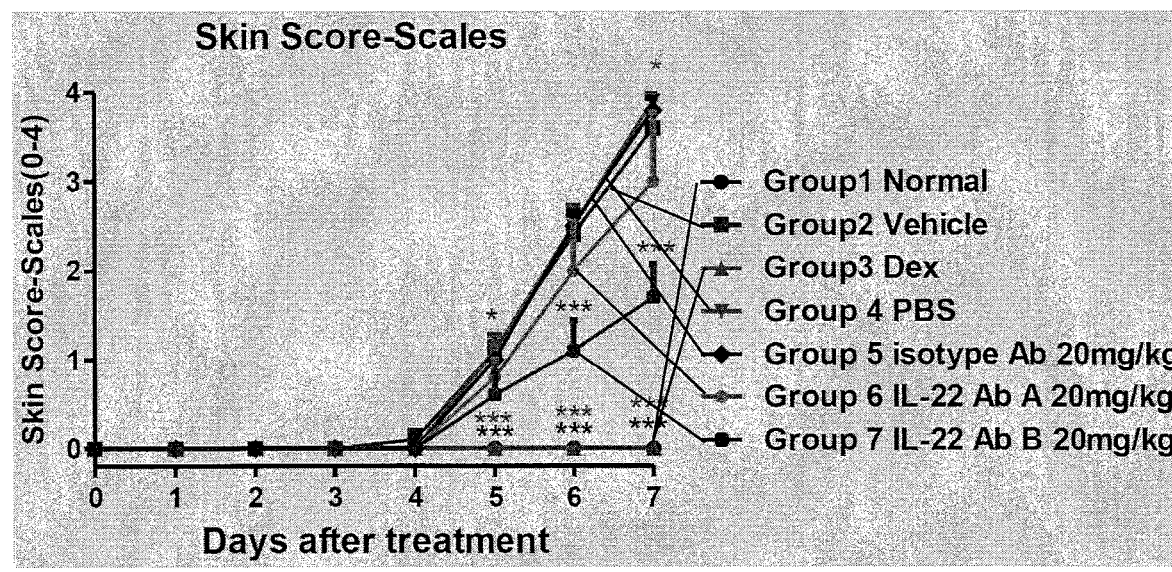
FIG. 16 shows changes of skin scale score of the treated mice during the treatment period following the study design shown in FIG. 12.
Figure 17:
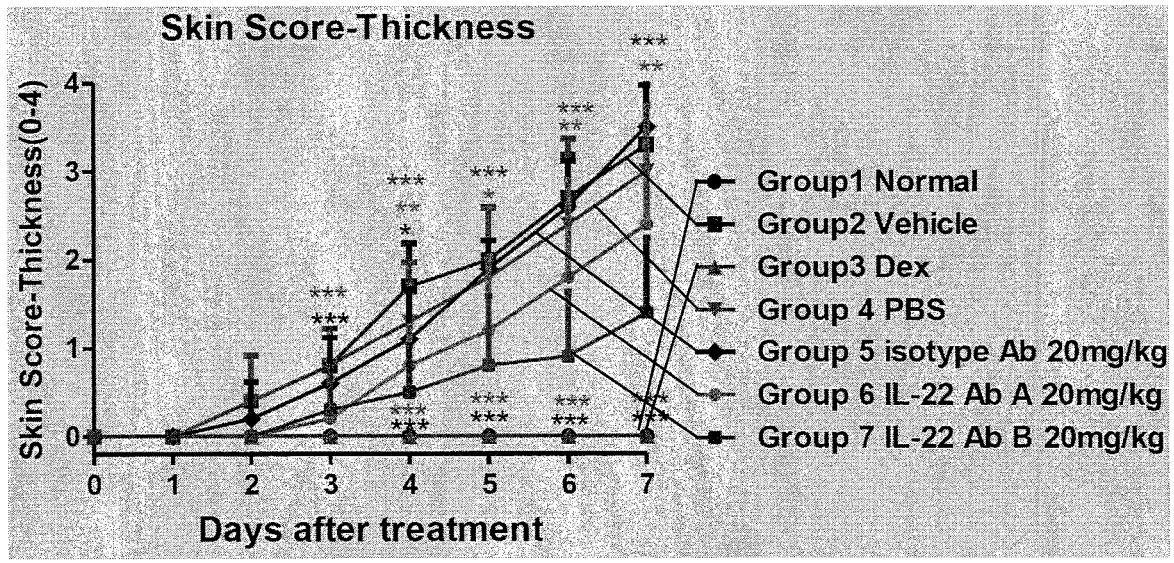
FIG. 17 shows changes of skin thickness score of the treated mice during the treatment period following the study design shown in FIG. 12.
Figure 18:
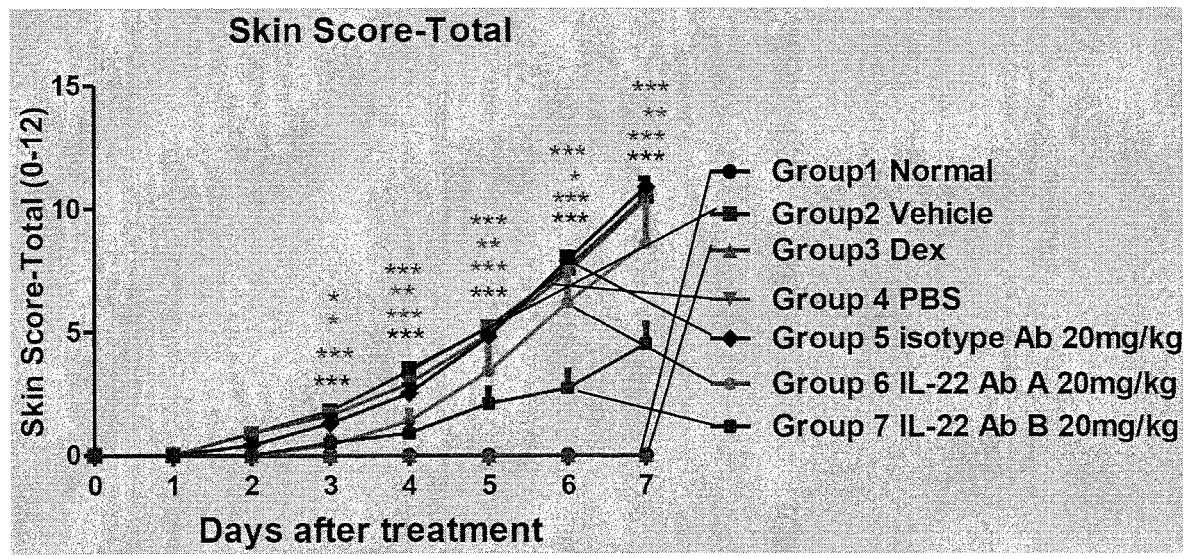
FIG. 18 shows changes of total skin score (overall skin condition) of the treated mice during the treatment period following the study design shown in FIG. 12.

Two anti-IL-22 antibodies of the present invention, CPS02 and CPS09, were used for the treatment of imiquimod (IMQ) induced psoriasis in mice (FIG. 12). The mice were male BALB/c mice, which were an albino, laboratory-bred strain of the house mouse. A total of 70 mice, at a body weight of 18-20 g, were acclimated for 7 days before induction of psoriasis.

The 70 mice were randomized into 7 groups (10 mice in each group). One group (group 1) was used as a negative control to which no imiquimod was administered to the mice, which was instead replaced with Vaseline. Thus, this negative control group did not have induced psoriasis. The other 6 groups (groups 2-7) were dosed topically with imiquimod at a dosage of 82.5 mg/mouse (5% cream) once daily (qd) for 8 consecutive days from day 0 to day 7 (20 mg for the left ear, 62.5 mg for the shaved back) to induce psoriasis. The back skin was shaved to expose an area of 2×3 cm². For the Vaseline control group, the Vaseline was also applied at 82.5 mg/mouse once daily (qd) for 8 consecutive days (20 mg for left ear, 62.5 mg for the shaved back) from day 0 to day 7.

Psoriasis treatments were administered only to the mice in groups 3-7, and thus groups 1-2 were untreated, as shown in Table 5. Group 2 was a group of psoriasis-induced mice that were untreated to serve as a control group. Groups 3-7 were treated with various treatment regimens as set forth in Table 5. The treatment period completely overlapped with the imiquimod application period (day 0 to day 7). For group 2, the mice received both imiquimod and dexamethasone on each day of the 8-day period (day 0 to day 7). For the groups that received intravenous (I.V.) injection, the imiquimod was applied within one hour after the I.V. injection on days 0 and 3.

TABLE 5

Treatment of Psoriasis in Mice

| Group | Topical induction | Treatment | Treatment Frequency/duration |
|---|---|---|---|
| 1 | Vaseline-Topical | — | — |
| 2 | IMQ-Topical | — | — |
| 3 | IMQ-Topical | Dexamethasone 80 mg/mice | Topical, BID, for 8 days |
| 4 | IMQ-Topical | PBS | I.V. single injection on day 0 and day 3 |
| 5 | IMQ-Topical | Isotype control Ab at 20 mg/kg | I.V. single injection on day 0 and day 3 |
| 6 | IMQ-Topical | anti-IL22 antibody A at 20 mg/kg on day 0 and 10 mg/kg on day 3 | I.V. single injection on day 0 and day 3 |
| 7 | IMQ-Topical | anti-IL22 antibody B at 20 mg/kg | I.V. single injection on day 0 and day 3 |

Group 3 was treated with the steroid dexamethasone, which is a current therapeutic treatment used for psoriasis. The dexamethasone was topically applied twice a day (BID) for 8 days. Group 4 was treated with phosphate-buffered saline (PBS), which served as a negative control. Group 5 was treated with an isotype control antibody that also served as a negative control. Groups 6-7 were treated with the anti-IL22 antibodies CPS02 (A) and CPS09 (B), respectively. The treatments for Groups 4-7 were administered by a single intravenous (I.V.) injection on each of days 0 and 3. 3 mice in group 6 died on day 0 and 2 died on day 1. On day 3, the I.V. injection dosage for this group was decreased to 10 mg/kg.

During the 8 day treatment period, the ear thickness was measured on days 0, 3, 5 and 7. The body weight and various skin scores were recorded daily. Pictures of the psoriasis sites were taken on days 0, 3, 5 and 7. On days 1 and 4, about 60 µl blood was collected via retro-orbital bleeding over 24 hours and placed in BD Microtainer® tubes coated with dipotassium ethylenediaminetetraacetic acid ($K_2EDTA$). Plasma was then collected (to get at least 20 µl plasma) and stored at −80° C. These samples were further analyzed and the results are presented in FIG. 12.

Skin scores for erythema, scales and thickness were measured daily according to an established grading system. The erythema, scales and thickness were scored independently on a scale of from 0 to 4: 0 means none, 1 means slight, 2 means moderate, 3 means marked, and 4 means very marked. The cumulative (total) skin score was also calculated.

At the conclusion of the treatment (day 7), the following end points were collected:
  Spleen index (spleen weight/body weight)
  Blood collected and the serum isolated and stored at −80° C.
  Affected skin from the back and the left ear collected (1) for each mouse, with 1 slide for back skin and 1 slide for left ear, (2) 1 representative picture/group
  Real-time PCR for back skin samples was performed. Total mRNA was extracted from affected back skin and subject to real-time PCR for determination expression of IL-23, IL-22, CCL3, CXCL3, NPG, IL-17A, S100A7 and Loricrin (β-actin as control).

The effects of the treatments were analyzed statistically using two-way analysis of variance (ANOVA, Bonferroni post-tests) or one-way ANOVA analysis. For comparisons between the treatment groups and the control group, the p value is denoted in FIGS. 13-18 as (*) if less than 0.05, () if less than 0.01, or (*) if less than 0.001.

It was observed that the anti-IL22 antibodies CPS02 (A) and CPS09 (B) caused less reduction in body weight of the treated mice, in comparison to mice treated with dexamethasone. In fact, the anti-IL22 antibody CSP09 (B) resulted in a reduction in body weight similar to the PBS buffer negative control. This is a clear indication that the anti-IL22 antibodies of the present invention reduced at least one harmful side effect when compared with the known treatment by dexamethasone. See FIG. 13.

The symptoms of psoriasis are measured by observing skin thickness, erythema and scales. A lesser skin thickness is an indication of a more successful treatment. Ear skin thickness was less for mice treated with the anti-IL22 antibodies CSP02 (A) and CSP09 (B) than for mice treated with the negative controls, isotype matched antibody, PBS and vehicle treatment. The earn thickness of the mice treated by dexamethasone was similar to that of mice that were not subjected to the imiquimod induction. See FIG. 14.

The skin erythema scores for the mice treated with the anti-IL22 antibodies CSP02 (A) and CSP09 (B) were also lower than the skin erythema scores observed in the mice treated with the negative controls, isotype matched antibody, PBS and vehicle treatment. Again, the skin erythema score for the mice treated by dexamethasone was similar to that of mice that were not subjected to the imiquimod induction. See FIG. 15.

The skin scale scores for the mice treated with the anti-IL22 antibodies CSP02 (A) and CSP09 (B) were also lower than the skin scale scores for mice treated with the negative controls, isotype matched antibody, PBS and vehicle treatment. Again, the skin scales score for the mice treated with dexamethasone was similar to the skin scale scores of mice that were not subjected to the imiquimod induction. See FIG. 16.

The skin thicknesses for the mice treated with the anti-IL22 antibodies CSP02 (A) and CSP09 (B) were also lower than the skin thicknesses for mice treated with the negative controls, isotype matched antibody, PBS and vehicle treatment. Again, the skin thickness of the mice treated by dexamethasone was similar to the skin thickness of mice that were not subjected to the imiquimod induction. See FIG. 17.

Finally, the overall condition of the skin was evaluated as a total skin score for the treated mice. The total skin score for the mice treated with the anti-IL22 antibodies CSP02 (A) and CSP09 (B) were also lower than the total skin score for mice treated with the negative controls, isotype matched antibody, PBS and vehicle treatment. The mice treated with the anti-IL22 antibody CSP09 (B) had a particularly good total skin score. Again, the total skin score of the mice treated with dexamethasone was similar to the total skin score of mice that were not subjected to the imiquimod induction. See FIG. 18.

In summary, the anti-IL22 antibodies were effective for treating psoriasis in the mouse model as demonstrated by improvements in each of the psoriasis symptoms of skin thickness, erythema and scales. At the same time, the conditionally active anti-IL22 antibodies exhibited a reduced side effect in comparison with the known treatment for psoriasis. The anti-IL22 antibody CSP09 (b) was especially effective in treating psoriasis and exhibited only a minimal side effect.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

All documents mentioned herein are hereby incorporated by reference in their entirety and at least to provide the disclosure for which they were specifically relied upon or cited as referring to. The applicant(s) do not intend to dedicate any disclosed embodiments to the public, and to the extent any disclosed modifications or alterations may not literally fall within the scope of the claims, they are considered to be part hereof under the doctrine of equivalents.

```

What is claimed is:

1. An anti-IL-22 antibody or antigen binding fragment thereof comprising:
a light chain variable region including a light chain CDR1 (LCDR1) having an amino acid sequence selected from SASSSVSX$_1$MH (SEQ ID NO:1), a light chain CDR2 (LCDR2) having an amino acid sequence selected from X$_2$TX$_3$KLX$_4$S (SEQ ID NO:2), and a light chain CDR3 (LCDR3) having an amino acid sequence of QQWSSNPYIT (SEQ ID NO:3); and
a heavy chain variable region including a heavy chain CDR1 (HCDR1) having an amino acid sequence selected from GYIFX$_5$SYWIH (SEQ ID NO:4), a heavy chain CDR2 (HCDR2) having an amino acid sequence selected from RIYPGTGX$_6$TYYNX$_7$KFKG (SEQ ID NO:5), and a heavy chain CDR3 (HCDR3) having an amino acid sequence selected from SYX$_8$X$_9$SVX$_{10}$Y (SEQ ID NO:6),
wherein X$_1$ is Y or K, X$_2$ is E or K, X$_3$ is S or R, X$_4$ is A or L, X$_5$ is T or R, X$_6$ is N or R, X$_7$ is E or R, X$_8$ is D or M, X$_9$ is S or Y, and X$_{10}$ is A or G, with the proviso that X$_1$ to X$_{10}$ cannot be Y, E, S, A, T, N, E, D, S, and A, respectively, at the same time; and up to three of X$_1$ to X$_4$ can be other than Y, E, S, and A, respectively, at the same time, and up to five of X$_5$ to X$_{10}$ can be other than T, N, E, D, S, and A, respectively, at the same time.

2. The anti-IL-22 antibody or antigen binding fragment thereof of claim 1, wherein the light chain variable region has an amino acid sequence selected from SEQ ID NOS: 7-12, and the heavy chain variable region has an amino acid sequence selected from SEQ ID NOS: 13-18.

3. The anti-IL-22 antibody or antigen binding fragment thereof of claim 2, wherein the antibody or antigen binding fragment thereof is selected from:
an antibody or antigen binding fragment thereof comprising the light chain variable region having the amino acid sequence of SEQ ID NO: 7 and the heavy chain variable region having the amino acid sequence of SEQ ID NO: 13;
an antibody or antigen binding fragment thereof comprising the light chain variable region having the amino acid sequence of SEQ ID NO: 10 and the heavy chain variable region having the amino acid sequence of SEQ ID NO: 13;
an antibody or antigen binding fragment thereof comprising the light chain variable region having the amino acid sequence of SEQ ID NO: 11 and the heavy chain variable region having the amino acid sequence of SEQ ID NO: 14;

an antibody or antigen binding fragment thereof comprising the light chain variable region having the amino acid sequence of SEQ ID NO: 8 and the heavy chain variable region having the amino acid sequence of SEQ ID NO: 15;

an antibody or antigen binding fragment thereof comprising the light chain variable region having the amino acid sequence of SEQ ID NO: 9 and the heavy chain variable region having the amino acid sequence of SEQ ID NO: 15;

an antibody or antigen binding fragment thereof comprising the light chain variable region having the amino acid sequence of SEQ ID NO: 10 and the heavy chain variable region having the amino acid sequence of SEQ ID NO: 15;

an antibody or antigen binding fragment thereof comprising the light chain variable region having the amino acid sequence of SEQ ID NO: 8 and the heavy chain variable region having the of amino acid sequence of SEQ ID NO: 16;

an antibody or antigen binding fragment thereof comprising the light chain variable region having the amino acid sequence of SEQ ID NO: 7 and the heavy chain variable region having the amino acid sequence of SEQ ID NO: 17;

an antibody or antigen binding fragment thereof comprising the light chain variable region having the amino acid sequence of SEQ ID NO: 8 and the heavy chain variable region having the amino acid sequence of SEQ ID NO: 17; and an antibody or antigen binding fragment thereof comprising the light chain variable region having the amino acid sequence of SEQ ID NO: 12 and the heavy chain variable region having the amino acid sequence of SEQ ID NO: 18.

4. The anti-IL-22 antibody or antigen binding fragment thereof of claim 1, wherein the anti-IL-22 antibody or antigen binding fragment thereof is humanized.

5. The anti-IL-22 antibody or antigen binding fragment thereof of claim 1, wherein the anti-IL-22 antibody or antigen binding fragment thereof comprises a modified Fc region.

6. The anti-IL-22 antibody or antigen binding fragment thereof of claim 1, wherein the antibody or antigen binding fragment thereof binds to human IL-22 and a mammalian non-human IL-22.

7. The anti-IL-22 antibody or antigen binding fragment thereof of claim 6, wherein the mammalian non-human IL-22 is mouse IL-22.

8. The anti-IL-22 antibody or antigen binding fragment thereof of claim 6, wherein the antibody or antigen binding fragment thereof binds to the human IL-22 and the mammalian non-human IL-22 with affinities within plus or minus 20% of each other.

9. The anti-IL-22 antibody or antigen binding fragment thereof of claim 1, wherein the antibody or antigen binding fragment thereof inhibits phosphorylation of Stat3.

10. The anti-IL-22 antibody or antigen binding fragment thereof of claim 1, wherein the antibody or antigen binding fragment thereof inhibits IL-22-induced cytokine production.

11. The anti-IL-22 antibody or antigen binding fragment thereof of claim 1, wherein the antibody or antigen binding fragment thereof inhibits an immune response selected from the group consisting of cell proliferation, cytolytic activity, cytokine secretion, and chemokine secretion.

12. The anti-IL-22 antibody or antigen binding fragment thereof of claim 11, wherein the anti-IL-22 antibody or antigen binding fragment thereof inhibits an immune response in a non-human mammal.

13. The anti-IL-22 antibody or antigen binding fragment thereof of claim 12, wherein the non-human mammal is a mouse.

14. A pharmaceutical composition comprising:
the antibody or antigen binding fragment thereof of claim 1; and
a pharmaceutically acceptable carrier.

15. A kit for diagnosis or treatment, said kit comprising:
the pharmaceutical composition of claim 14; and instructions for using the pharmaceutical composition for diagnosis or treatment.

16. A method of treating an immune disorder selected from the group consisting of rheumatoid arthritis, juvenile rheumatoid arthritis, osteoarthritis, psoriatic arthritis, or ankylosing spondylitis; asthma, chronic obstructive pulmonary disease; psoriasis, atherosclerosis, hepatitis, nephritis, pancreatitis, endotoxemia, sepsis, septicaemia, amyloidosis, glomerulosclerosis, membranous neuropathy, renal arteriosclerosis, glomerulonephritis and fibroproliferative diseases of the kidney comprising a step of administering the pharmaceutical composition of claim 14, to a subject.

17. A kit for diagnosis or treatment, said kit comprising:
the antibody or antigen binding fragment thereof of claim 1; and
instructions for using the antibody or antigen binding fragment thereof, for diagnosis or treatment.

18. A method of treating an immune disorder selected from the group consisting of rheumatoid arthritis, juvenile rheumatoid arthritis, osteoarthritis, psoriatic arthritis, or ankylosing spondylitis; asthma, chronic obstructive pulmonary disease; psoriasis, atherosclerosis, hepatitis, nephritis, pancreatitis, endotoxemia, sepsis, septicaemia, amyloidosis, glomerulosclerosis, membranous neuropathy, renal arteriosclerosis, glomerulonephritis and fibroproliferative diseases of the kidney comprising a step of administering the antibody or antigen binding fragment thereof of claim 1 to a subject.

19. A modified anti-IL-22 antibody or antigen binding fragment thereof comprising the anti-IL-22 antibody or antigen binding fragment thereof of claim 1 and at least one moiety selected from oligosaccharides, non-proteinaceous moieties, a therapeutic agent, and a diagnostic agent.

20. The modified anti-IL-22 antibody or antigen binding fragment thereof of claim 19, wherein the at least one moiety is an oligosaccharide.

21. The modified anti-IL-22 antibody or antigen binding fragment thereof of claim 19, wherein the at least one moiety is at least one non-proteinaceous moiety selected from soluble polymers.

22. The modified anti-IL-22 antibody or antigen binding fragment thereof of claim 19, wherein the at least one moiety is selected from a therapeutic agent and a diagnostic agent.

23. The modified anti-IL-22 antibody or antigen binding fragment thereof of claim 22, wherein the therapeutic agent or diagnostic agent is conjugated to the anti-IL-22 antibody or antigen binding fragment thereof and is selected from a chemotherapeutic agent, a radioactive atom, a detectable label, a prodrug activating enzyme, a cytostatic agent and a cytotoxic agent.

24. The modified anti-IL-22 antibody or antigen binding fragment thereof of claim 22, wherein the antibody or antigen binding fragment thereof and the therapeutic agent or diagnostic agent are covalently bonded to a linker molecule.

25. A pharmaceutical composition comprising the modified anti-IL22 antibody or antigen binding fragment thereof of claim 19.

26. A kit for diagnosis or treatment, said kit comprising: the modified anti-IL-22 antibody or antigen binding fragment thereof of claim 19; and instructions for using the modified the antibody or antigen binding fragment thereof for diagnosis or treatment.

27. A method of treating an immune disorder selected from the group consisting of rheumatoid arthritis, juvenile rheumatoid arthritis, osteoarthritis, psoriatic arthritis, or ankylosing spondylitis; asthma, chronic obstructive pulmonary disease; psoriasis, atherosclerosis, hepatitis, nephritis, pancreatitis, endotoxemia, sepsis, septicaemia, amyloidosis, glomerulosclerosis, membranous neuropathy, renal arteriosclerosis, glomerulonephritis and fibroproliferative diseases of the kidney comprising a step of administering the modified anti-IL-22 antibody or antigen binding fragment thereof of claim 19, to a subject.

28. An anti-IL22 antibody or antigen binding fragment thereof comprising:
   a light chain variable region having an amino acid sequence that has at least 90% sequence identity to one of the amino acid sequences of SEQ ID NOS: 7-12, wherein the light chain variable region has three complementarity determining regions that are identical to complementarity determining regions of a light chain variable region having an amino acid sequence selected from SEQ ID NOS: 7-12; and
   a heavy chain variable region having an amino acid sequence that has at least 90% sequence identity to one of the amino acid sequences of SEQ ID NOS: 13-18, wherein the heavy chain variable region has three complementarity determining regions that are identical to complementarity determining regions of a heavy chain variable region having an amino acid sequence selected from SEQ ID NOS: 13-18.

29. The anti-IL22 antibody or antigen binding fragment thereof of claim 28, wherein the anti-IL22 antibody or antigen binding fragment is selected from the group consisting of:
   an antibody or antigen binding fragment comprising a light chain variable region having an amino acid sequence that has at least 95% sequence identity to one of the amino acid sequences of SEQ ID NOS: 7-12 and a heavy chain variable region having an amino acid sequence that has at least 95% sequence identity to one of the amino acid sequences of SEQ ID NO: 13-18,
   an antibody or antigen binding fragment comprising a light chain variable region having an amino acid sequence that has at least 98% sequence identity to one of the amino acid sequences of SEQ ID NOS: 7-12 and a heavy chain variable region having an amino acid sequence that has at least 98% sequence identity to one of the amino acid sequences of SEQ ID NO: 13-18, and
   an antibody or antigen binding fragment comprising a light chain variable region having an amino acid sequence that has at least 99% sequence identity to one of the amino acid sequences of SEQ ID NOS: 7-12 and a heavy chain variable region having an amino acid sequence that has at least 99% sequence identity to one of the amino acid sequences of SEQ ID NO: 13-18.

* * * * *

                      SEQUENCE LISTING

<160> NUMBER OF SEQ ID NOS: 20

<210> SEQ ID NO 1
<211> LENGTH: 10
<212> TYPE: PRT
<213> ORGANISM: Artificial
<220> FEATURE:
<223> OTHER INFORMATION: Synthetic sequence LC-CDR1
<220> FEATURE:
<221> NAME/KEY: X
<222> LOCATION: (8)..(8)
<223> OTHER INFORMATION: X may be Y or K

<400> SEQUENCE: 1

Ser Ala Ser Ser Ser Val Ser Xaa Met His
1               5                   10

<210> SEQ ID NO 2
<211> LENGTH: 7
<212> TYPE: PRT
<213> ORGANISM: Artificial
<220> FEATURE:
<223> OTHER INFORMATION: Synthetic sequence LC-CDR2
<220> FEATURE:
<221> NAME/KEY: X
<222> LOCATION: (1)..(1)
<223> OTHER INFORMATION: X may be E or K
<220> FEATURE:
<221> NAME/KEY: X
<222> LOCATION: (3)..(3)
<223> OTHER INFORMATION: X may be S or R
<220> FEATURE:
<221> NAME/KEY: X
<222> LOCATION: (6)..(6)
<223> OTHER INFORMATION: X may be A or L

<400> SEQUENCE: 2

Xaa Thr Xaa Lys Leu Xaa Ser
1               5

<210> SEQ ID NO 3
<211> LENGTH: 10
<212> TYPE: PRT
<213> ORGANISM: Artificial
<220> FEATURE:
<223> OTHER INFORMATION: Synthetic sequence of LC-CDR3

<400> SEQUENCE: 3
```

```
Gln Gln Trp Ser Ser Asn Pro Tyr Ile Thr
1               5                   10
```

<210> SEQ ID NO 4
<211> LENGTH: 10
<212> TYPE: PRT
<213> ORGANISM: Artificial
<220> FEATURE:
<223> OTHER INFORMATION: Synthetic sequence HC-CDR1
<220> FEATURE:
<221> NAME/KEY: X
<222> LOCATION: (5)..(5)
<223> OTHER INFORMATION: X may be T or R

<400> SEQUENCE: 4

```
Gly Tyr Ile Phe Xaa Ser Tyr Trp Ile His
1               5                   10
```

<210> SEQ ID NO 5
<211> LENGTH: 17
<212> TYPE: PRT
<213> ORGANISM: Artificial
<220> FEATURE:
<223> OTHER INFORMATION: Synthetic sequence HC-CDR2
<220> FEATURE:
<221> NAME/KEY: X
<222> LOCATION: (8)..(8)
<223> OTHER INFORMATION: X may be N or R
<220> FEATURE:
<221> NAME/KEY: X
<222> LOCATION: (13)..(13)
<223> OTHER INFORMATION: X may be E or R

<400> SEQUENCE: 5

```
Arg Ile Tyr Pro Gly Thr Gly Xaa Thr Tyr Tyr Asn Xaa Lys Phe Lys
1               5                   10                  15

Gly
```

<210> SEQ ID NO 6
<211> LENGTH: 8
<212> TYPE: PRT
<213> ORGANISM: Artificial sequence
<220> FEATURE:
<223> OTHER INFORMATION: Synthetic sequence HC-CDR3
<220> FEATURE:
<221> NAME/KEY: X
<222> LOCATION: (3)..(3)
<223> OTHER INFORMATION: X may be D or M
<220> FEATURE:
<221> NAME/KEY: X
<222> LOCATION: (4)..(4)
<223> OTHER INFORMATION: X may be S or Y
<220> FEATURE:
<221> NAME/KEY: X
<222> LOCATION: (7)..(7)
<223> OTHER INFORMATION: X may be A or G

<400> SEQUENCE: 6

```
Ser Tyr Xaa Xaa Ser Val Xaa Tyr
1               5
```

<210> SEQ ID NO 7
<211> LENGTH: 108
<212> TYPE: PRT
<213> ORGANISM: ARTIFICIAL
<220> FEATURE:
<223> OTHER INFORMATION: Aynthetic sequence LC-CPS-03

<400> SEQUENCE: 7

```
Ala Ile Gln Leu Thr Gln Ser Pro Ser Ser Leu Ser Ala Ser Val Gly
```

```
                1               5                   10                  15
Asp Arg Val Thr Ile Thr Cys Ser Ala Ser Ser Ser Val Ser Tyr Met
                20                  25                  30

His Trp Tyr Leu Gln Lys Pro Gly Gln Ser Pro Gln Leu Leu Ile Tyr
                35                  40                  45

Lys Thr Ser Lys Leu Ala Ser Gly Val Pro Ser Arg Phe Ser Gly Ser
                50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Tyr Ile
                85                  90                  95

Thr Phe Gly Gln Gly Thr Lys Val Glu Ile Lys Arg
                100                 105
```

<210> SEQ ID NO 8
<211> LENGTH: 108
<212> TYPE: PRT
<213> ORGANISM: Artificial
<220> FEATURE:
<223> OTHER INFORMATION: Synthetic sequence LC-CPS-04

<400> SEQUENCE: 8

```
Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

His Trp Tyr Leu Gln Lys Pro Gly Gln Ser Pro Gln Leu Leu Ile Tyr
                35                  40                  45

Glu Thr Arg Lys Leu Ala Ser Gly Val Pro Ser Arg Phe Ser Gly Ser
                50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Tyr Ile
                85                  90                  95

Thr Phe Gly Gln Gly Thr Lys Val Glu Ile Lys Arg
                100                 105
```

<210> SEQ ID NO 9
<211> LENGTH: 108
<212> TYPE: PRT
<213> ORGANISM: Artificial
<220> FEATURE:
<223> OTHER INFORMATION: Synthetic sequence LC-CPS-05

<400> SEQUENCE: 9

```
Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

His Trp Tyr Leu Gln Lys Pro Gly Gln Ser Pro Gln Leu Leu Ile Tyr
                35                  40                  45

Glu Thr Ser Lys Leu Leu Ser Gly Val Pro Ser Arg Phe Ser Gly Ser
                50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Tyr Ile
                85                  90                  95
```

```
Thr Phe Gly Gln Gly Thr Lys Val Glu Ile Lys Arg
            100                 105
```

<210> SEQ ID NO 10
<211> LENGTH: 108
<212> TYPE: PRT
<213> ORGANISM: Artificial
<220> FEATURE:
<223> OTHER INFORMATION: Synthetic sequence LC-CPS-06

<400> SEQUENCE: 10

```
Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Leu Gln Lys Pro Gly Gln Ser Pro Gln Leu Leu Ile Tyr
        35                  40                  45

Lys Thr Arg Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Tyr Ile
                85                  90                  95

Thr Phe Gly Gln Gly Thr Lys Val Glu Ile Lys Arg
            100                 105
```

<210> SEQ ID NO 11
<211> LENGTH: 108
<212> TYPE: PRT
<213> ORGANISM: Artificial
<220> FEATURE:
<223> OTHER INFORMATION: Synthetic sequence LC-CPS-07

<400> SEQUENCE: 11

```
Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Leu Gln Lys Pro Gly Gln Ser Pro Gln Leu Leu Ile Tyr
        35                  40                  45

Lys Thr Ser Lys Leu Leu Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Tyr Ile
                85                  90                  95

Thr Phe Gly Gln Gly Thr Lys Val Glu Ile Lys Arg
            100                 105
```

<210> SEQ ID NO 12
<211> LENGTH: 108
<212> TYPE: PRT
<213> ORGANISM: Artificial
<220> FEATURE:
<223> OTHER INFORMATION: Synthetoc sequence LC-CPS-11

<400> SEQUENCE: 12

```
Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Lys Met
```

```
            20                  25                  30
His Trp Tyr Leu Gln Lys Pro Gly Gln Ser Pro Gln Leu Leu Ile Tyr
        35                  40                  45

Glu Thr Arg Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Tyr Ile
                85                  90                  95

Thr Phe Gly Gln Gly Thr Lys Val Glu Ile Lys Arg
            100                 105
```

<210> SEQ ID NO 13
<211> LENGTH: 117
<212> TYPE: PRT
<213> ORGANISM: Artificial
<220> FEATURE:
<223> OTHER INFORMATION: Synthetic sequence HC-CPS-08

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Arg Ser Tyr
            20                  25                  30

Trp Ile His Trp Ile Arg Gln Pro Pro Gly Lys Gly Leu Glu Trp Ile
        35                  40                  45

Gly Arg Ile Tyr Pro Gly Thr Gly Arg Thr Tyr Tyr Asn Glu Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Tyr Asp Ser Ser Val Ala Tyr Trp Gly Gln Gly Thr Leu
            100                 105                 110

Val Thr Val Ser Ser
        115
```

<210> SEQ ID NO 14
<211> LENGTH: 117
<212> TYPE: PRT
<213> ORGANISM: Artificial
<220> FEATURE:
<223> OTHER INFORMATION: Synthetic sequence HC-CPS-09

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Arg Ser Tyr
            20                  25                  30

Trp Ile His Trp Ile Arg Gln Pro Pro Gly Lys Gly Leu Glu Trp Ile
        35                  40                  45

Gly Arg Ile Tyr Pro Gly Thr Gly Asn Thr Tyr Tyr Asn Arg Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

Ala Arg Ser Tyr Asp Ser Ser Val Ala Tyr Trp Gly Gln Gly Thr Leu
            100                 105                 110

Val Thr Val Ser Ser
        115

<210> SEQ ID NO 15
<211> LENGTH: 117
<212> TYPE: PRT
<213> ORGANISM: Artificial
<220> FEATURE:
<223> OTHER INFORMATION: Synthetic sequence HC-CPS-25

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Arg Ser Tyr
            20                  25                  30

Trp Ile His Trp Ile Arg Gln Pro Pro Gly Lys Gly Leu Glu Trp Ile
        35                  40                  45

Gly Arg Ile Tyr Pro Gly Thr Gly Arg Thr Tyr Tyr Asn Glu Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Tyr Asp Tyr Ser Val Ala Tyr Trp Gly Gln Gly Thr Leu
            100                 105                 110

Val Thr Val Ser Ser
        115

<210> SEQ ID NO 16
<211> LENGTH: 117
<212> TYPE: PRT
<213> ORGANISM: Artificial
<220> FEATURE:
<223> OTHER INFORMATION: Synthetic sequence HC-CPS-31

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Trp Ile His Trp Ile Arg Gln Pro Pro Gly Lys Gly Leu Glu Trp Ile
        35                  40                  45

Gly Arg Ile Tyr Pro Gly Thr Gly Arg Thr Tyr Tyr Asn Arg Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Tyr Asp Tyr Ser Val Ala Tyr Trp Gly Gln Gly Thr Leu
            100                 105                 110

Val Thr Val Ser Ser
        115

<210> SEQ ID NO 17
<211> LENGTH: 117
<212> TYPE: PRT
<213> ORGANISM: Artificial

```
<220> FEATURE:
<223> OTHER INFORMATION: Synthetic sequence HC-CPS-49

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Arg Ser Tyr
            20                  25                  30

Trp Ile His Trp Ile Arg Gln Pro Pro Gly Lys Gly Leu Glu Trp Ile
        35                  40                  45

Gly Arg Ile Tyr Pro Gly Thr Gly Asn Thr Tyr Tyr Asn Arg Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Tyr Met Tyr Ser Val Ala Tyr Trp Gly Gln Gly Thr Leu
            100                 105                 110

Val Thr Val Ser Ser
        115

<210> SEQ ID NO 18
<211> LENGTH: 117
<212> TYPE: PRT
<213> ORGANISM: Artificial
<220> FEATURE:
<223> OTHER INFORMATION: Synthetic sequence HC-CPS-50

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Arg Ser Tyr
            20                  25                  30

Trp Ile His Trp Ile Arg Gln Pro Pro Gly Lys Gly Leu Glu Trp Ile
        35                  40                  45

Gly Arg Ile Tyr Pro Gly Thr Gly Asn Thr Tyr Tyr Asn Arg Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Tyr Met Ser Ser Val Gly Tyr Trp Gly Gln Gly Thr Leu
            100                 105                 110

Val Thr Val Ser Ser
        115

<210> SEQ ID NO 19
<211> LENGTH: 108
<212> TYPE: PRT
<213> ORGANISM: Artificial
<220> FEATURE:
<223> OTHER INFORMATION: Synthetic sequence hum10-LC

<400> SEQUENCE: 19

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30
```

```
His Trp Tyr Leu Gln Lys Pro Gly Gln Ser Pro Gln Leu Leu Ile Tyr
            35                  40                  45

Glu Thr Ser Lys Leu Ala Ser Gly Val Pro Ser Arg Phe Ser Gly Ser
 50                  55                  60

Gly Ser Gly Thr Asp Phe Thr Phe Thr Ile Ser Ser Leu Glu Ala Glu
 65              70                  75                  80

Asp Ala Ala Thr Tyr Tyr Cys Gln Gln Trp Ser Ser Asn Pro Tyr Ile
                 85                  90                  95

Thr Phe Gly Gln Gly Thr Lys Val Glu Ile Lys Arg
             100                 105

<210> SEQ ID NO 20
<211> LENGTH: 117
<212> TYPE: PRT
<213> ORGANISM: Artificial
<220> FEATURE:
<223> OTHER INFORMATION: Synthetic sequence hum10-HC

<400> SEQUENCE: 20

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ile Phe Thr Ser Tyr
                 20                  25                  30

Trp Ile His Trp Ile Arg Gln Pro Pro Gly Lys Gly Leu Glu Trp Ile
             35                  40                  45

Gly Arg Ile Tyr Pro Gly Thr Gly Asn Thr Tyr Tyr Asn Glu Lys Phe
 50                  55                  60

Lys Gly Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser Tyr Asp Ser Ser Cys Ala Tyr Trp Gly Gln Gly Thr Leu
                100                 105                 110

Val Thr Val Ser Ser
            115
```